United States Patent [19]
Loskutoff et al.

[11] Patent Number: 6,103,876
[45] Date of Patent: *Aug. 15, 2000

[54] DIAGNOSTIC ASSAY FOR INHIBITOR OF TISSUE-TYPE AND UROKINASE-TYPE PLASMINOGEN ACTIVATORS AND GENE CODING FOR THE INHIBITOR

[75] Inventors: David J. Loskutoff, Solana Beach, Calif.; Tor Ny, Umea, Sweden; Michael Sawdey, La Jolla, Calif.

[73] Assignee: The Scripps Research Institute, La Jolla, Calif.

[ * ] Notice: This patent is subject to a terminal disclaimer.

[21] Appl. No.: 08/855,407

[22] Filed: May 13, 1997

Related U.S. Application Data

[63] Continuation of application No. 08/248,348, May 24, 1994, Pat. No. 5,629,160, which is a continuation of application No. 07/877,271, Apr. 29, 1992, Pat. No. 5,314,994, which is a continuation of application No. 07/573,485, Aug. 27, 1990, abandoned, which is a division of application No. 06/897,990, Aug. 19, 1986, Pat. No. 4,952,512, which is a continuation-in-part of application No. 06/623,357, Jun. 22, 1984, Pat. No. 4,791,068.

[51] Int. Cl.$^7$ .......................... C07K 16/00; C07K 16/18; C07K 16/38

[52] U.S. Cl. ...................... 530/387.1; 530/387.2; 530/388.1; 530/389.1; 530/388.25; 530/389.3

[58] Field of Search ................. 530/350, 387.1, 530/387.2, 388.15, 388.2, 388.25, 388.26, 389.1, 389.3

[56] References Cited

PUBLICATIONS

Eaton, D. et al., JBC, 259 (10):6241–47, May 1984.

*Primary Examiner*—Marianne P. Allen
*Attorney, Agent, or Firm*—Thomas Fitting; Emily Holmes

[57] ABSTRACT

A biological reagent and diagnostic system for the detection and quantitation of endothelial plasminogen activator inhibitor (PAI) are disclosed, as are substantially pure, recombinant human endothelial PAI, its biologically pure gene and a vector for cloning the gene and expressing a gene product.

11 Claims, 24 Drawing Sheets

ANALYSIS OF PURIFIED INHIBITOR BY SDS-PAGE 1    2    3

IMMUNOPRECIPITATION OF INHIBITOR FROM ³H-CM

```
         -4              -4  +1
       Gly Gly Ser Ala Val His His Pro Pro Ser Tyr Val Ala His Leu
    1  GAA GGG TCT GCT GTG CAC CAT CCC CCA TCC TAC GTG GCC CAC CTG

Ala Ser Asp Phe Gly Val Arg Val Phe Gln Gln Val Ala Gln Ala  26
       GCC TCA GAC TTC GGG GTG AGG GTG TTT CAG CAG GTG GCG CAG GCC

Ser Lys Asp Arg Asn Val Val Phe Ser Pro Tyr Gly Val Ala Ser
   91  TCC AAG GAC CGC AAC GTG GTT TTC TCA CCC TAT GGG GTG GCC TCG

Val Leu Ala Met Leu Gln Leu Thr Thr Gly Gly Glu Thr Gln Gln  56
       GTG TTG GCC ATG CTC CAG CTG ACA ACA GGA GGA GAA ACC CAG CAG

Gln Ile Gln Ala Ala Met Gly Phe Lys Ile Asp Asp Lys Gly Met
  181  CAG ATT CAA GCA GCT ATG GGA TTC AAG ATT GAT GAC AAG GGC ATG

Ala Pro Ala Leu Arg His Leu Tyr Lys Glu Leu Met Gly Pro Trp  86
       GCC CCC GCC CTC CGG CAT CTG TAC AAG GAG CTC ATG GGG CCA TGG

Asn Lys Asp Glu Ile Ser Thr Thr Asp Ala Ile Phe Val Gln Arg
  271  AAC AAG GAT GAG ATC AGC ACC ACA GAC GCG ATC TTC GTC CAG CGG

Asp Leu Lys Leu Val Gln Gly Phe Met Pro His Phe Phe Arg Leu  116
       GAT CTG AAG CTG GTC CAG GGC TTC ATG CCC CAC TTC TTC AGG CTG

Phe Arg Ser Thr Val Lys Gln Val Asp Phe Ser Glu Val Glu Arg
  361  TTC CGG AGC ACG GTC AAG CAA GTG GAC TTT TCA GAG GTG GAG AGA

Ala Arg Phe Ile Ile Asn Asp Trp Val Lys Thr His Thr Lys Gly  146
       GCC AGA TTC ATC ATC AAT GAC TGG GTG AAG ACA CAC ACA AAA GGT

Met Ile Ser Asn Leu Leu Gly Lys Gly Ala Val Asp Gln Leu Thr
  451  ATG ATC AGC AAC TTG CTT GGG AAA GGA GCC GTG GAC CAG CTG ACA

Arg Leu Val Leu Val Asn Ala Leu Tyr Phe Asn Gly Gln Trp Lys  176
       CGG CTG GTG CTG GTG AAT GCC CTC TAC TTC AAC GGC CAG TGG AAG

Thr Pro Phe Pro Asp Ser Ser Thr His Arg Arg Leu Phe His Lys
  541  ACT CCC TTC CCC GAC TCC AGC ACC CAC CGC CGC CTC TTC CAC AAA

Ser Asp Gly Ser Thr Val Ser Val Pro Met Met Ala Gln Thr Asn  206
       TCA GAC GGC AGC ACT GTC TCT GTG CCC ATG ATG GCT CAG ACC AAC

Lys Phe Asn Tyr Thr Glu Phe Thr Thr Pro Asp Gly His Tyr Tyr
  631  AAG TTC AAC TAT ACT GAG TTC ACC ACG CCC GAT GGC CAT TAC TAC

Asp Ile Leu Glu Leu Pro Tyr His Gly Asp Thr Leu Ser Met Phe  236
       GAC ATC CTG GAA CTG CCC TAC CAC GGG GAC ACC CTC AGC ATG TTC

Ile Ala Ala Pro Tyr Glu Lys Glu Val Pro Leu Ser Ala Leu Thr
  721  ATT GCT GCC CCT TAT GAA AAA GAG GTG CCT CTC TCT GCC CTC ACC

Asn Ile Leu Ser Ala Gln Leu Ile Ser His Trp Lys Gly Asn Met  266
       AAC ATT CTG AGT GCC CAG CTC ATC AGC CAC TGG AAA GGC AAC ATG
```

FIG. 22A

```
        Thr Arg Leu Pro Arg Leu Leu Val Leu Pro Lys Phe Ser Leu Glu
    811 ACC AGG CTG CCC CGC CTC CTG GTT CTG CCC AAG TTC TCC CTG GAG

Thr Glu Val Asp Leu Arg Lys Pro Leu Glu Asn Leu Gly Met Thr 296
        ACT GAA GTC GAC CTC AGG AAG CCC CTA GAG AAC CTG GGA ATG ACC

Asp Met Phe Arg Gln Phe Gln Ala Asp Phe Thr Ser Leu Ser Asp
    901 GAC ATG TTC AGA CAG TTT CAG GCT GAC TTC ACG AGT CTT TCA GAC

Gln Glu Pro Leu His Val Ala Gln Ala Leu Gln Lys Val Lys Ile 326
        CAA GAG CCT CTC CAC GTC GCG CAG GCG CTG CAG AAA GTG AAG ATC

Glu Val Asn Glu Ser Gly Thr Val Ala Ser Ser Ser Thr Ala Val
    991 GAG GTG AAC GAG AGT GGC ACG GTG GCC TCC TCA TCC ACA GCT GTC

Ile Val Ser Ala Arg Met Ala Pro Glu Glu Ile Ile Met Asp Arg 356
        ATA GTC TCA GCC CGC ATG GCC CCC GAG GAG ATC ATC ATG GAC AGA

Pro Phe Leu Phe Val Val Arg His Asn Pro Thr Gly Thr Val Leu
   1081 CCC TTC CTC TTT GTG GTC CGG CAC AAC CCC ACA GGA ACA GTC CTT

Phe Met Gly Gln Val Met Glu Pro
        TTC ATG GGC CAA GTG ATG GAA CCC TGA CCC TGG GGA AAG ACG CCT

1171 TCATCTGGGACAAAACTGGAGATGCATCGGGAAAGAAGAAACTCCGAAGAAAAGAATTT
        TAGTGTTAATGACTCTTTCTGAAGGAAGAGAAGACATTTGCCTTTTGTTAAAAGATGGTAA
   1291 ACCAGATCTGTCTCCAAGACCTTGGCCTCTCCTTGGAGGACCTTTAGGTCAAACTCCCT
        AGTCTCCACCTGAGACCCTGGGAGAGAAGTTTGAAGCACAACTCCCTTAAGGTCTCCAAAC
   1411 CAGACGGTGACGCCTGCGGGACCATCTGGGGCACCTGCTTCCACCCGTCTCTCTGCCCA
        CTCGGGTCTGCAGACCTGGTTCCCACTGAGGCCCTTTGCAGGACGGAACTACGGGGCTTAC
   1531 AGGAGCTTTTGTGTGCCTGGTAGAAACTATTTCTGTTCCAGTCACATTGCCATCACTCT
        TGTACTGCCTGCCACCGCGGAGGAGGCTGGTGACAGGCCAAAGGCCAGTGGAAGAAACACC
   1651 CTTTCATCTCAGAGTCCACTGTGGCACTGGCCACCCCTCCCCAGTACAGGGTGCTGCA
        GGTGGCAGAGTGAATGTCCCCCATCATGTGGCCCAACTCTCCTGGCCTGGCCATCTCCCTC
   1771 CCCAGAAACAGTGTGCATGGGTTATTTTGGAGTGTAGGTGACTTGTTTACTCATTGAAG
        CAGATTTCTGCTTCCTTTTATTTTTATAGGAATAGAGGAAGAAAGGTCAGATGCGTGCCCA
   1891 GCTCTTCACCCCCCAATCTCTTGGTGGGGAGGGGTGTACCTAAATATTTATCATATCCT
        TGCCCTTGAGTGCTTGTTAGAGAGAAAGAGAACTACTAAGGAAAATAATATTATTTAAACT
   2011 CGCTCCTAGTGTTTCTTTGTGGTCTGTGTCACCGTATCTCAGGAAGTCCAGCCACTTGA
        CTGGCACACACCCCTCCGGACATCCAGCGTGACGGAGCCCACACTGCCACCTTGTGGCCGC
   2131 CTGAGACCCTCGCGCCCCCGCGCCCCCGCGCCCCTCTTTTTCCCCTTGATGGAAATT
        GACCATACAATTTCATCCTCCTTCAGGGGATCAAAAGGACGGAGTGGGGGGACAGAGACTC
   2251 AGATGAGGACAGAGTGGTTTCCAATGTGTTCAATAGATTTAGGAGCAGAAATGCAAGGG
        GCTGCATGACCTACCAGGACAGAACTTTCCCCAATTACAGGGTGACTCACAGCCGCATTGG
   2371 TGACTCACTTCAATGTGTCATTTCCGGCTGCTGTGTGTGAGCAGTGGACACGTGAGGGG
        GGGGTGGGTGAGAGAGACAGGCAGCTCGGATTCAACTACCTTAGATAATATTTCTGAAAAC
   2491 CTACCAGCCAGAGGGTAGGGCACAAAGATGGATGTAATGCACTTTGGGAGGCCAAGGCA
        GGAGGATTGCTTGAGCCCAGGAGTTCAAGACCAGCCTGGGCAACATACCAAGACCCCGTC
   2611 TCTTTAAAAATATATATATTTTAAATATACTTAAATATATATTTCTAATATCTTTAAAT
        ATATATATATATTTTAAAGACCAATTTATGGGAGAATTGCACACAGATGTGAAATGAATGT
   2731 AATCTAATAGAAGCCTAATCAGCCCACCATGTTCTCCACTGAAAAATCCTCTTTCTTTG
        GGGTTTTCTTTCTTTCTTTTTTGATTTTGCACTGGACGGTGACGTCAGCCATGTACAGGA
   2851 TCCACAGGGGTGGTGTCAAATGCTATTGAAATTGTGTTGAATTGTATGCTTTTTCACTT
        TTGATAAATAAACATGTAAAAATGTTTCAAAAAAA
```

FIG. 22B

| | | | | | | | | | | | |
|---|---|---|---|---|---|---|---|---|---|---|---|
| β PAI | P | L | H | V | A | Q | L | K | V | K | I E V N E S G T |
| α₁AT | P | L | K | L | S | K | A | V | H | V | A V L T I D E K G T |
| AT III | D | L | Y | V | S | D | A | F | H | K | A F L E V N E E G S |

| | | | | | | | | | |
|---|---|---|---|---|---|---|---|---|---|
| β PAI | V | A | S | S | T | A | V | I | V S A R M A P E E |
| α₁AT | E | A | A | G | A | M | F | L | E A I P M S I P P |
| AT III | E | A | A | A | S | T | A | V | V I A G R S L N P N |

$\overline{\phantom{XXXX}}$  
$P_1\ P_1'$

FIG. 24

DIAGNOSTIC ASSAY FOR INHIBITOR OF TISSUE-TYPE AND UROKINASE-TYPE PLASMINOGEN ACTIVATORS AND GENE CODING FOR THE INHIBITOR

CROSS REFERENCE TO RELATED APPLICATION

This is a continuation of application Ser. No. 08/248,348, filed May 24, 1994 and now U.S. Pat. No. 5,629,160, which is a continuation of application Ser. No. 07/877,271, filed Apr. 29, 1992 and now U.S. Pat. No. 5,314,994, which was a continuation of application Ser. No. 07/573,485 filed Aug. 27, 1990, now abandoned, which was a division of application Ser. No. 06/897,990, filed Aug. 19, 1986 and now U.S. Pat. No. 4,952,512, which was a continuation-in-part of application Ser. No. 06/623,357 filed Jun. 22, 1984, now U.S. Pat. No. 4,791,068.

This invention was made with the support of the United States Government through National Institutes of Health grants EL-22289, HL-16411 and HL-33985. The United States Government has certain rights in the invention.

TECHNICAL FIELD

The present invention relates to a biochemical reagent system including a receptor and an indicating means that recognizes and selectively binds to a plasminogen activator inhibitor, and more particularly relates to biochemical reagent and diagnostic systems for the detection and quantitation of beta-migrating endothelial cell plasminogen activator inhibitor in blood and other biological samples, as well as to the human beta-migrating, endothelial cell plasminogen activator inhibitor in substantially pure form, and its gene.

BACKGROUND OF THE INVENTION

Endothelial cells line the luminal surface of the vascular bed and are thought to play an active role in the specific proteolytic breakdown of locally deposited fibrin, Todd, *J. Pathol. Bacteriol.*, 78, 281 (1959); Astrup, in *Progress in Chemical Fibrinolysis and Thrombolysis*, Davidson et al. eds., vol. 3, pp. 1–57, Raven Press, New York (1978). The potential of endothelium to initiate and control this process is emphasized by its capacity to synthesize and release plasminogen activators (PAs), Loskutoff et al., *Proc. Natl. Acad. Sci.* (*USA*), 74, 3903 (1977); Shepro et al., *Thromb. Res.*, 18, 609 (1980); Moscatelli et al., *Cell*, 20, 343 (1980); Laug, *Thromb. Haemostasis*, 45, 219 (1981); Booyse et al., *Thromb. Res.*, 24, 495 (1981), including both tissue-type and urokinase-type molecules, Levin et al., *J. Cell Biol.*, 94, 631 (1982); Loskutoff et al., *Blood*, 62, 62 (1983). Endothelial cells can also produce inhibitors of fibrinolysis, Loskutoff et al., *Proc. Natl. Acad. Sci.* (*USA*), 74, 3903 (1977); Levin et al., *Thromb. Res.*, 15, 869 (1979); Loskutoff et al., *J. Biol. Chem.*, 256, 4142 (1981); Dosne et al., *Thromb. Res.*, 12, 377 (1978); Emeis et al., *Biochem. Biophys. Res. Commun.*, 110, 392 (1983); Loskutoff et al., *Proc. Natl. Acad. Sci.* (*USA*), 80, 2956 (1983); Levin, *Proc. Natl. Acad. Sci.* (*USA*), 80, 6804 (1983).

Although these inhibitors probably serve important regulatory roles in controlling the fibrinolytic system of the vascular wall, little is known about their specificity, mode of action, or biochemical nature. The conclusion that these inhibitors are actually synthesized by endothelial cells is obscured somewhat by recent reports that cultured cells can bind and internalize protease inhibitors from serum-containing culture medium, Cohen, *J. Clin. Invest.*, 52, 2793 (1973); Pastan et al., *Cell*, 12, 609 (1977); Rohrlich et al., *J. Cell Physiol.*, 109, 1 (1981); McPherson et al., *J. Biol. Chem.*, 256, 11330 (1981).

The possibility of producing relatively unlimited amounts of tissue-type plasminogen activator (t-PA) by recombinant DNA technology as described in British patent application GB 2,119,804 A, published Nov. 23, 1983, has generated much interest, both clinically and commercially. The conversion of the relatively inactive molecule into an extremely efficient thrombolytic agent by fibrin itself, suggests that t-PA can exist as an active enzyme only when localized to the fibrin-platelet thrombus itself. Thus, t-PA is considered to be a much more specific thrombolytic agent than urokinase-type plasminogen activator and streptokinase.

The interactions between t-PA and fibrin have raised the argument that natural inhibitors of t-PA are not necessary to regulate this system; i.e., regulation is achieved through the formation/dissolution of fibrin, and, thus, do not exist. It is clear that the existence of such inhibitors in human blood would complicate attempts to design a specific, efficient, and safe thrombolytic program based upon natural and genetically engineered t-PA. At the very least, calculations such as those of dose, treatment time and efficacy of treatment would be difficult to predict and/or monitor. This problem would be especially acute if inhibitor levels varied from individual to individual.

The existence of specific inhibitors of t-PA in plasma is a matter of some dispute, Collen, *Thromb. Haemostas.*, 43, 77 (1980). In fact, it has been reported, Korninger et al., *Thromb. Haemostas.*, 46, 662 (1981), that the activity of t-PA added to plasma had an in vitro half-life of 90 minutes as compared to an in vivo half-life of 2 minutes, Korninger et al., *Thromb. Haemostas*, 46, 658 (1981). Based upon these observations, those authors concluded that t-PA inhibition by plasma was physiologically unimportant.

That conclusion has recently been challenged in Kruithof et al., *Prog. in Fibrinolysis*, 6, 362 (1983). In Chmielewska et al., *Thromb. Res.*, 31, 427 (1983), direct evidence was recently reported for the existence of a rapid inhibitor of t-PA in plasma. In all cases, this anti-t-PA activity was detected in the plasma of patients with or at risk to develop thrombotic problems; i.e., the very individuals most likely to receive t-PA therapy. This finding may account for the failure of Korninger et al., *Thromb. Haemostas.*, 46, 662 (1981), to detect such an activity since they only examined the plasma of "normal" individuals. These reports on t-PA inhibitors represent little more than qualitative descriptions of an "activity" detected in the blood of some individuals.

Recently, an antifibrinolytic agent in cultured bovine endothelial cells was detected, Loskutoff et al., *Proc. Natl. Acad. Sci.* (*USA*), 80, 2956 (1983). This inhibitor is a major endothelial cell product and is an inhibitor of plasiminogen activator since it can neutralize the activity of both fibrin-independent (urokinase-type) and fibrin-dependent (tissue-type) plasminogen activators (PAs). The observation that human platelets contain an immunologically similar inhibitor, Erickson et al., *Haemostasis*, 14 (1), 65 (1984) and *J. Clin. Invest.* 74, 1465 (1984), that is released by them in response to physiologically relevant stimuli, e.g., thrombin, and in parallel with other platelet proteins, e.g., Platelet Factor 4, emphasizes the potential importance of this inhibitor in human biology. Antiserum to the plasminogen activator inhibitor (PAT) from bovine aortic endothelial cells (BAEs) has been employed to show that the human endothelial PAI as well as that from plasma, serum and platelets are related, i.e., immunologically similar. Erickson et al., *Proc. Natl. Acad. Sci. USA,* 82, 8710 (1985).

The inhibitor found by Loskutoff et al., *Proc. Natl. Acad. Sci. (USA),* 80, 2956 (1983), was purified from bovine aortic endothelial cell conditioned media by a combination of concanavalin A affinity chromatography and preparative sodium dodecyl sulfate-polyacrylamide gel electrophoresis (SDS-PAGE), and was shown to be a single chain glycoprotein of a molecular weight of 50,000 daltons, having an isoelectric point of 4.5–5 [van Mourik et al., *J. Biol. Chem.* 259, 14914 (1984)].

Recent evidence indicates that there are three immunologically distinct plasminogen activator inhibitors (PAIs). The first is that discussed above that is derived primarily from endothelial cells. The second, reported by Astedt et al., *Thromb. Haemostasis,* 53, 122 (1985) was isolated from placenta. The third, reported by Scott et al., *J. Biol. Chem.,* 260 7029 (1985) is protease nexin.

The endothelial cell type PAI differs, in addition to immunologically, from placental PAI and protease nexin in that it inhibits both single chain and two chain tissue-type plasminogen activator (t-PA) as well as urokinase-type plasminogen activator (u-PA), while protease nexin and the placental PAI exhibit substantially no t-PA inhibition at physiological concentrations. Those latter two inhibitors do inhibit u-PA activity at physiological concentrations. Still further, endothelial PAI exhibits beta-mobility when analyzed by agarose zone electrophoresis while the other two PAIs do not. In addition the endothelial cell PAI is stable to low pH values (e.g. pH 3) and SDS (0.1%), while the other two inhibitors are rapidly inactivated by either of these treatments. [van Mourik et al., *J. Biol. Chem.,* 259, 14914 (1984)].

The results discussed hereinafter illustrate that the endothelial cell type PAT exhibiting beta-mobility is also present in human placental extracts as is the placenta PAI reported by Astedt et al., *Thromb. Haemostasis,* 53., 122 (1985). Since two types of PAI are obtainable, from placenta, the human PAI hereinbefore referred to as of endothelial cell origin will usually be referred to as beta-PAT or endothelial PAI, or endothelial cell type PAT while the PAI first isolated from placenta is referred to as placental-type PAI or placental PAI.

SUMMARY OF THE INVENTION

The present invention contemplates a biochemical reagent system and methods of preparing and using same, diagnostics utilizing the reagent system, a method for detecting PAI, a substantially cure recombinant proteinaceous molecule that is immunologically similar to human endothelial cell type plasminogen activator inhibitor and has the binding and inhibiting activities of human beta-migrating, endothelial cell plasminogen activator inhibitor, and its gene.

The biochemical reagent system comprises (a) a receptor such as an antibody raised in an animal host to endothelial cell plasminogen activator inhibitor; i.e., an anti-plasminogen activator inhibitor, and (b) an indicating means. In one aspect of the invention, the biochemical reagent system is comprised of (a) a receptor that can be a polyclonal antibody raised in an animal host and (b) an indicating means, The indicating means and receptor can be a single molecule or can be composed of a plurality of individual molecules. The receptor binds to endothelial cell (beta-migrating) plasminogen activator inhibitor that itself binds to and inhibits tissue-type or urokinase-type plasminogen activators. The indicating means labels the receptor, and in so doing indicates the presence of the inhibitor in a sample to be assayed such as serum of patients having thrombotic disease. The receptor of the reagent system of the present invention selectively binds to endothelial cell plasminogen activator inhibitor bound to either tissue-type (t-PA) or to urokinase-type (u-PA) plasminogen activators.

In another aspect of the present invention, a method of forming a polyclonal receptor for use in a biochemical reagent system is contemplated. The method comprises the steps of: (a) administering to an animal host endothelial cell type plasminogen activator inhibitor (PAI) in an amount sufficient to induce the production of antibodies to the inhibitor, the antibodies being a receptor for the inhibitor; (b) collecting antisera containing the antibodies from the immunized host; and (c) recovering the receptor from the antisera.

Yet another aspect of the present invention relates to a method of forming a biochemical reagent system. The method comprises the steps of forming the polyclonal receptor described above as stems (a)–(c) with an additional step (d) of combining the receptor with an indicating means.

Both of the above methods can also include the step of administering to the host after step (a) and a sufficient period of incubation (maintenance) of the host, e.g., 1–2 weeks, but before step (b), a second injection of the same inhibitor to boost the production of antibody.

The present invention also contemplates polyclonal receptors produced by the above-described method.

In a further aspect of the present invention, a solid phase assay method of detecting the presence and quantity of endothelial cell type plasminogen activator inhibitor in a sample to be assayed is contemplated. The method comprises the steps of: (a) providing a solid matrix on which to assay the sample; (b) affixing on the solid matrix a binding reagent that binds to (complexes with) the inhibitor to form a solid phase support, the binding reagent being a plasminogen activator selected from the group consisting of t-PA and u-PA or the above-described polyclonal receptor; (c) admixing an aliquot of a liquid sample to be assayed with the solid phase support to form a solid-liquid phase admixture; (d) maintaining the admixture for a predetermined time sufficient for the binding reagent to bind to (complex with) any of the plasminogen activator inhibitor present in the sample; (e) separating the solid and liquid phases; and (f) determining the presence of inhibitor that bound to (complexed with) the binding reagent.

In preferred practice, the quantity of inhibitor bound to the binding reagent is determined by (i) admixing an aqueous liquid solution of second binding reagent that binds to the inhibitor bound on the solid support with the solid phase obtained after step (e) above to form a second solid-liquid phase admixture, the second binding reagent complexing with the inhibitor; (ii) maintaining the second solid-liquid admixture for a predetermined time sufficient for the second binding reagent to bind (form a complex) with the inhibitor (typically about 2 to about 4 hours); (iii) separating the solid and liquid phases of the second solid-liquid phase admixture; and (iv) determining the quantity of the second binding reagent that bound to the inhibitor, and thereby determining the quantity of inhibitor.

The present invention further includes a mammalian diagnostic system such as a kit. The kit includes at least one package containing as an active ingredient the biochemical reagent system of this invention and t-PA or u-PA. The biochemical reagent system comprises a polyclonal receptor in dry, solution, or dispersion form, that, when admixed with an indicating means and a sample to be assayed, binds selectively to endothelial plasminogen activator inhibitor (PAI) present in the sample and indicates the presence and amount of the inhibitor. Indicating groups that can be contained in the system include a radioactive element, a biologically active enzyme, or an NMR-active element.

The diagnostic system can also include a solid matrix that can be a microtiter strip such as that containing twelve wells in a row. The t-PA or u-PA present is preferably bound to the solid matrix.

The diagnostic system can further include a standard against which to compare the assay results, as well as various buffers in dry or liquid form, for, inter alia, washing the wells, diluting the sample or diluting the labeled reagent.

The use of a biochemical reagent system of this invention includes the detection and quantitation of a specific plasminogen activator inhibitor that is bound to (complexed with) a plasminogen activator such as tissue-type or urokinase-type plasminogen activator. An especially preferred use of such a reagent system relates to the detection of plasminogen activator inhibitor in an in vitro protocol.

Still another aspect of the present invention is a substantially pure, recombinant proteinaceous molecule, antibodies to which immunoreact with human endothelial cell type plasminogen activator inhibitor. More preferably, that recombinant molecule also binds to and inhibits the activities of at least t-PA, and most preferably binds to and inhibits the activities of both t-PA and u-PA. The recombinant molecule is immunologically different from protease nexin and placental PAI. In one embodiment, the recombinant molecule is substantially free of polypeptide-linked glycosyl groups, while in another embodiment the inhibitor contains polypeptide-linked glycosyl groups. In one non-glycosylated embodiment, the recombinant molecule exhibits an apparent relative molecule mass ($M_r$) of about 180 kildoaltons (kda) in SDS-PAGE analysis as a fusion polypeptide, while in another non-glycosylated embodiment the $M_r$ is about 40 kda.

It is seen from the above discussion that the recombinant molecule need not have the full biological activity of the naturally occurring (native) human endothelial cell type PAI. While it is preferred that the molecule have biological activity of its native homolog and bind to as well as inhibit at least t-PA, the recombinant molecule is also useful because of its immunological similarity to the native protein and thus its ability to induce secretion of receptor molecules that cross-react with the native protein, as is discussed hereinafter.

Another aspect of the present invention is a biologically pure DNA molecule containing about 1140 to about 3000 nucleotides and including a nucleotide sequence that consists essentially of a nucleotide sequence, from left to right and in the direction from 5'-terminus to 3'-terminus, corresponding to the sequence represented by the formula in FIG. 22 from nucleotide position 13 to about 1153, and in a consistent reading frame coding for human endothelial cell type plasminogen activator inhibitor. I another embodiment, the DNA molecule sequenc corresponds to that from position 1 to about position 1960. In still another embodiment, the DNA molecule sequence corresponds to that from position 1 to about position 1153. Yet another embodiment the DNA sequence corresponds to the entire DNA sequence shown in FIG. 22.

A non-chromosomal vector for cloning DNA in a replication/expression medium comprising a replicon compatible with the medium and containing a before-described DNA molecule in such a manner that the vector can propagate the DNA molecule. The vector preferably further includes a transcriptional promoter that is operatively linked to the contained DNA molecule adjacent to the 5'-terminus of the DNA molecule, and compatible with the replication/expression medium for expressing a product coded for by the DNA molecule that includes a recombinant, human endothelial cell type plasminogen activator inhibitor. More preferably, the vector still further includes a translation initiating codon and a translation terminating codon, both of which are operationally linked to the contained DNA molecule adjacent to the 5'-terminus and the 3'-terminus thereof, respectively, and compatible with the replication/expression medium for expressing a product coded for by the DNA molecule.

A solid phase assay method of detecting the presence and quantity of endothelial cell type human plasminogen activator inhibitor in a sample to be assayed constitutes yet another aspect of this invention. Here, a solid phase support is provided comprising a solid matrix to which the substantially pure, recombinant proteinaceous molecule (described before) is affixed. An aliquot of a liquid sample to be assayed is admixed with a predetermined amount of a binding reagent that binds to (complexes with) both the recombinant molecule of the solid support and the inhibitor to be assayed. That admixture is maintained under biological assay conditions and for a predetermined period of time sufficient for the binding reagent to bind to any of the inhibitor present in the sample. That admixture is admixed with the solid support to form a solid-liquid phase admixture. That admixture is maintained under biological assay conditions for a predetermined period of time sufficient for any binding reagent of the admixture not bound to inhibitor molecules of the sample to bind to the recombinant inhibitor of the solid support. The solid and liquid phases are thereafter separated, and the amount of binding reagent bound to the recombinant inhibitor of the solid support is determined. In one embodiment, the binding reagent is a receptor molecule that immunoreacts with both the recombinant proteinaceous molecule and human endothelial cell type PAI. In another embodiment, the binding reagent is t-PA or u-PA.

The present invention provides several benefits and advantages.

One benefit of the present invention is that the biochemical reagent system and diagnostic system of the invention are highly specific. Biological samples frequently contain numerous fibrinolytic inhibitors. It is difficult to distinguish among them by existing assays since those assays, in general, measure the capacity of a sample to decrease the activity of plasminogen activators or plasmin. In contrast, a preferred diagnostic system of the present invention detects only inhibitor bound to particular plasminogen activators, and furthermore, detects only those recognized by the specific antiserum utilized.

Another benefit of the present invention is that the reagent system of the invention is quantitative, providing in one embodiment, a measure of the quantity of functionally active inhibitor bound to PAs, and not inhibitor activity. Therefore, the reagent system may not be as influenced by changes in salt or pH, for example, as are enzymatic assays. It is the functionally active form that is likely to change in various diseases.

The inhibitor, as released by endothelial cells and platelets, exists in two forms, one active, and one inactive. The inactive form can be activated by treatment with denaturants, such as SDS and guanidine. Thus, an advantage of the reagent and diagnostic systems of the present invention is that they can be used to measure the relative amount of both active and inactive inhibitor in various samples.

Still another benefit of the present invention is that it provides a means for assaying the total amount of endothelial cell type plasminogen inhibitor present, whether active or inactive.

Another advantage of the present invention is that a diagnostic system of the invention can employ tissue-type plasminogen activator (t-PA) or urokinase-type plasminogen activator (u-PA) bound to wells of microtiter plates, and thus readily lends itself to screening large numbers of samples in a rapid and reproducible manner.

Other advantages and benefits of the present invention will become readily apparent to those skilled in the art from the following description of the invention, the drawings and the appended claims.

BRIEF DESCRIPTION OF THE DRAWINGS

In the drawings forming a portion of the disclosure of this invention:

FIG. 22 illustrates the complete nucleotide sequence of the cDNA insert of λ 3. The nucleotide sequence of the coding strand and the corresponding predicted amino acid sequence are shown. The numbers in the left margin refer to the positions of the nucleotides, and those on the right to the positions of the amino acid residues. The valine designated as number 1 is the amino-terminus of the encoded beta-PAI protein, and the amino acid residue sequence corresponding to the mature protein is numbered 1–379. The amino acid residue sequence that corresponds to a portion of the signal peptide is represented by the minus numbers in the opposite direction.

FIG. 24 provides portions of inferred amino acid residue sequences for comparison of beta-PAI, alpha-antitrypsin (alpha$_1$AT), and antithrombin III (AT III). The sequences of beta-PAI, alpha$_1$AT, and AT III around their reactive centers were aligned according to the "Fast Protein Homology Program" [Lipman et al. (1985) Science, 227, 1435–1441], using the single letter amino acid residue designations. The reactive site peptide bonds are indicated by the vertical line, and the terminology of the P$_1$-P$_1$' reactive site residues is adopted from Travis and Salvesen, (1983) Ann. Rev. Biochem. 52, 655–709. The reactive site methionines are underlined, and amino acid residues in alpha$_1$-AT and AT III homologous to those in beta-PAI are boxed.

DETAILED DESCRIPTION OF THE INVENTION

Definitions

Figure 1:
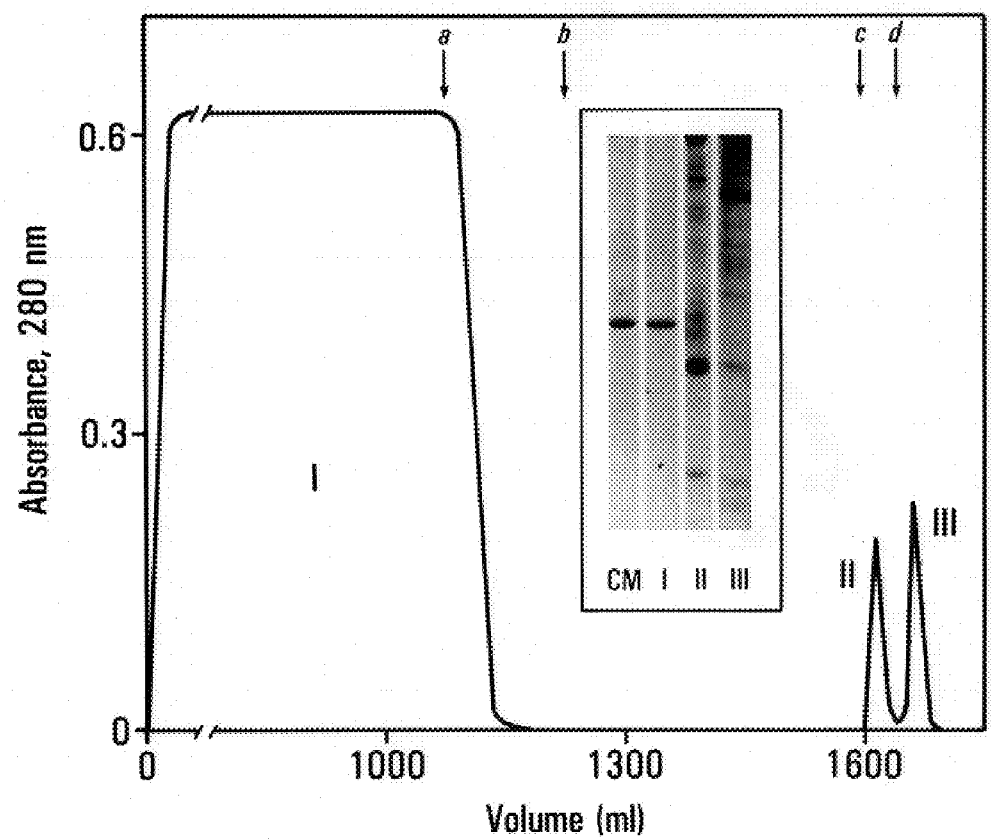
FIG. 1 is a graph illustrating the fractionation of conditioned media (CM) by affinity chromatography on concanavalin A-Sepharose. One liter of CM from confluent bovine aortic endothelial cells (BAEs) was passed over a 10 milliliter (ml) concanavalin A-Sepharose column as described in detail hereinafter. The column was washed sequentially with (a) 1 molar (M) NaCl, (b) 0.001M sodium phosphate, (c) 0.01M sodium phosphate containing 0.5M alpha-methyl-D-mannoside, and (d) 0.01M sodium phosphate containing 0.5M alpha-methyl-D-mannoside and 1M NaCl. The inset shows the protein profile of the starting material (CM), as well as the pooled run-through (I), alpha-methyl mannoside low (II) and high (III) salt fractions, all revealed after sodium dodecyl sulfate-polyacrylamide gel electrophoresis (SDS-PAGE) and staining with Coomassie Brilliant Blue (BioRad, Richmond, Calif.).

The term "plasminogen activator inhibitor" (PAI) as used herein is meant to indicate a protein that inhibits or checks the action of a plasminogen activator. The PAI useful herein can be from a number of sources such as bovine aortic endothelial cells (BAEs), human sources such as endothelial cells, placental extracts, platelets, plasma and serum, a transformed or neoplastic cell line (e.g. HG 1080), or that proteinaceous molecule prepared by recombinant techniques such as a fusion polypeptide as described herein. It is preferred that the PAI utilized at least bind to and inhibit the activity of tissue-type plasminogen activator, and thus the endothelial or beta-PAI described herein is the PAI of particular interest and choice as compared to the so-called placental PAI or protease nexin that primarily inhibit u-PA. More preferably, the useful inhibitor binds to and inhibits both t-PA and u-PA, as is also discussed herein.

"Plasminogen activator" is a protein that activates plasminogen, particularly in plasma, and converts it into plasmin in the fibrinolytic system of blood, cells, tissues and bodily fluids. Plasminogen activators useful in the present invention include tissue-type plasminogen activator (t-PA) and urokinase-type plasminogen activator (u-PA). As used herein, "urokinase-type" is meant to indicate urokinase and its homologous proteins as found in mammals other than humans.

The phrase "immunologically different" is used herein to mean that antibodies raised to one molecule do not immunoreact (cross-react) with another molecule. For example, antibodies raised to the recombinant proteinaceous molecule discussed hereinafter do not cross-react with either protease nexin or placental plasminogen activator inhibitor.

Conversely, the phrase "immunologically similar" is used herein to describe a molecule that is capable of inducing the secretion of antibodies that cross-react with another molecule, and thus, the two molecules are immunologically similar. For example, antibodies raised to the recombinant proteinaceous molecule discussed hereinafter cross-react with human and bovine endothelial cell type plasminogen activator inhibitors, and as a consequence, the three molecules are immunologically similar.

The phrase "proteinaceous molecule" is utilized herein to denote a relatively large polypeptide that has a relative apparent molecular mass of at least about 40,000 daltons. That phrase is meant to include both the recombinant molecule discussed hereinafter as a fusion between a portion of a beta-galactosidase protein derived from a vector and also the molecule translated from a denominated genomic sequence such as a sequence of FIG. 22.

The term "binding reagent" is used herein to mean a biologically active molecule that binds to or complexes with another molecule. A binding reagent can therefore be a receptor and its ligand such as an antibody or antigen that immunoreacts with its respective ligand (antigen) or receptor (antibody). Beta-PAI along with t-PA or u-PA also constitute binding reagents for each other, as do S. aureus Cowan strain protein A and an antibody Fc portion. Specific binding reagents and the moieties to which they bind are exemplified further hereinafter. However, receptors are utilized in this section to exemplify most of the terms defined that relate to binding reagents.

The term "receptor" as used herein is meant to indicate a biologically active molecule that binds to an antigen ligand. A receptor molecule or receptor of the present invention is an antibody, a substantially intact antibody in substantially purified form, such as is found in ascites fluid or serum of an immunized animal, or an idiotype-containing polypeptide portion of an antibody such as Fab and F(ab')$_2$ antibody portions as are described hereinafter.

Biological activity of a receptor molecule, or other binding reagent, is evidenced by the binding of the receptor to its antigenic ligand upon their admixture in an aqueous medium and maintenance under biological assay conditions for a predetermined time period of from minutes to hours such as about 10 minutes to about 16–20 hours that is sufficient to form an immunoreactant (complex).

Biological assay conditions are those that maintain the biological activity of the ligand and receptor molecules, or other binding and bound entities. Such assay conditions include a temperature range of about 4° C. to about 45° C. and physiological pH values and ionic strengths. Preferably, the receptors and other binding reagents also bind to the antigenic ligand within a pH value range of about 5 to about 9, and at ionic strengths such as that of distilled water to that of about one molar sodium chloride. Methods for optimizing such conditions are well known in the art.

Idiotype-containing polypeptide portions (antibody combining sites) of antibodies are those portions of antibody molecules that include the idiotype and bind to the ligand, and include the Fab, Fab' and F(ab')$_2$ portions of the antibodies. Fab and F(ab')$_2$ portions of antibodies are well known in the art, and are prepared by the reaction of papain and pepsin, respectively, on substantially intact antibodies by methods that are well known. See for example, U.S. Pat. No. 4,342,566 to Theofilopolous and Dixon. Fab' portions of antibodies are also well known and are prepared by the reduction of F(ab')$_2$ disulfide bonds as by mercaptoethanol followed by alkylation of the reduced cysteine residues so produced with a reagent such as iodoacetamide. Intact antibodies are preferred receptors, and are utilized as illustrative of the receptor molecules of this invention.

Antibodies and receptor molecules are discussed herein as being "raised" to a particular immunogen. While idiotype-containing antibody portions are products of man's action on antibodies, and are thus not "raised" as such, the term "raised" is used in conjunction with such receptors for convenience of expression.

The receptors utilized as illustrative in the present invention are polyclonal receptors. A "polyclonal receptor" (Pab) is a receptor produced by clones of different antibody-producing (-secreting) cells that produce (secrete) antibodies to a plurality of epitopes of the immunizing molecule. Monoclonal receptors as are secreted by clones of a hybridoma cell that secretes but one kind of antibody molecule are also contemplated. The hybridoma cell is fused from an antibody-producing (secreting) cell and a myeloma or other self-perpetuating cell line. Such receptors as whole antibodies were first described by Kohler and Milstein, *Nature*, 256, 495–497 (1975), which desciption is incorporated herein by reference.

Non-human, warm blooded animals usable in the present invention as hosts in which the polyclonal receptors are raised can include poultry (such as a chicken or a pigeon), a member of the ratitae bird group (such as an emu, ostrich, cassowary or moa) or a mammal (such as a dog, cat, monkey, goat, pig, cow, horse, rabbit, guinea pig, rat, hamster or mouse). Preferably, the host animal is a rabbit.

Receptors, and other binding reagents, are utilized along with an indicator labeling means or "indicating group" or a "label". The indicating group or label is utilized in conjunction with the receptor as a means for signalling (determining) that a specific inhibitor has bound to the receptor.

The terms "indicator labeling means", "indicating group" or "label" are used herein to include single atoms and molecules that are linked to the receptor or used separately, and whether those atoms or molecules are used alone or in conjunction with additional reagents. Such indicating groups or labels are themselves well-known in immunochemistry and constitute a part of this invention only insofar as they are utilized with otherwise novel receptors, methods and/or systems.

The signal-providing label utilized is typically linked to another molecule or part of a molecule, as discussed hereinafter. As such, the label is operationally linked to that other molecule or molecule part such as a receptor so that the binding of the molecule to which the label is linked is not substantially impaired by the label and the desired signalling provided by the label is not substantially impaired.

The indicator labeling means can be a reactive fluorescent labeling agent that chemically binds to antibodies or antigens without denaturing them to form a fluorochrome (dye) that is a useful immunofluorescent tracer. Suitable reactive fluorescent labeling agents are fluorochromes such as fluorescein isocyanate (FIC), flourescein isothiocyanate (FITC), dimethylamino-naphthalene-S-sulphonyl chloride (DANSC), tetramethylrhodamine isothiocyanate (TRITC), lissamine rhodamine B200 sulphonyl chloride (RB 200 SC) and the like. A description of immunofluorescence analysis techniques is found in DeLuca, "Immunoflourescence Analysis," in *Antibody As A Tool*, Marchalonis et al. eds., John Wiley & Sons Ltd., p. 189–231 (1982), which is incorporated herein by reference.

The indicator labeling means can be linked directly to a receptor of this invention, to a useful antigen or binding reagent such as t-PA or u-PA, or can comprise a separate molecule. It is particularly preferred that the indicator means be a separate molecule such as antibodies that bind to a receptor of this invention. *Staphylococcus aureus* Cowan strain protein A, sometimes referred to herein as protein A, can also be used as a separate molecule indicator or labeling means where an intact or substantially intact antibody receptor of this invention is utilized. In such uses, the protein A itself contains a label such as a radioactive element or a fluorochrome dye, as is discussed hereinafter.

The indicating group can also be a biologically active enzyme, such as horseradish peroxidase (HRP) or glucose oxidase, or the like. Where the principal indicating group is an enzyme such as HRP or glucose oxidase, additional reagents are required to visualize the fact that a receptor-ligand complex has formed. Such additional reagents for HRP include hydrogen peroxide and an oxidation dye precursor such as diaminobenzidine. An additional reagent useful with glucose oxidase is 2,2'azino-di-(3-ethylbenzthiazoline-6-sulfonic acid) (ABTS).

Radioactive elements provide another class of label, and are used herein as exemplary of useful labels. An exemplary radiolabeling agent that can be utilized in the invention is a radioactive element that produces gamma ray emissions. Elements which themselves emit gamma rays, such as $^{124}$I, $^{125}$i, $^{128}$I, $^{131}$I, $^{132}$I, and $^{51}$Cr represent one class of gamma ray emission-producing radioactive element indicating groups. Particularly preferred is $^{125}$I. Another class of useful indicating groups are those elements such as $^{11}$C, $^{18}$F, $^{15}$O, and $^{13}$N that themselves emit positrons. The positrons so emitted produce gamma rays upon encounters with electrons present in the analysis medium. Also useful is a beta ray emitter, such as $^{111}$indium.

Radioactive monoclonal receptors can be made by culturing an appropriate hybridoma in a medium containing radioactive amino acids, as is well known. Both monoclonal and polyclonal receptors can be prepared by isolating the receptors and then labeling them with one of the above radioactive elements. Radiolabeling of: proteins is well known in the art and will not be discussed further herein.

The following abbreviations and symbols are used herein.

bp—base pair(s)

kb—1000 bp kda—kilodalton(s)

$M_r$—apparent relative molecular mass

DNA—deoxyribonucleic acid cDNA—complementary DNA

RBS—ribosome binding site (Shine-Dalgarno sequence)

RNA—ribonucleic acid replicon—the unit that controls individual acts of replication; it has an origin at which replication is initiated and it may have a terminus at which replication stops.

The term "corresponds" in its various grammatical forms is used herein in relation to nucleotide codon sequences to mean the nucleotide codon sequence described containing only conservative codon substitutions that encode for particular amino acid residues along the protein sequence.

The term "conservative codon substitution" as used above is meant to denote that one codon has been replaced by another leading to translation of a protein in which an amino acid residue has been replaced by another, biologically similar residue. Examples of conservative substitutions at the amino acid residue (translation or expression) level include the substitution of one hydrophobic residue such as Ile, Val, Leu or Met for another, or the substitution of one polar residue for another such as between Arg and Lys, between Glu and Asp or between Gin and Asn, and the like.

In some instances, the replacement of an ionic residue by an oppositely charged ionic residue such as Asp by Lys has been termed conservative in the art in that those ionic groups are thought to merely provide solubility assistance. In general, however, replacement of an ionic residue by another ionic residue of opposite charge is considered herein to be "radical replacement", as are replacements between nonionic and ionic residues, and bulky residues such as Phe, Tyr or Trp and less bulky residues such as Gly, Ile and Val.

The terms "nonionic" and "ionic" residues are used herein in their usual sense to designate those amino acid residues that normally either bear no charge or normally bear a charge, respectively, at physiological pH values. Exemplary nonionic residues include Thr and Gln, while exemplary ionic residues include Arg and Asp.

At the nucleotide level, the term "corresponds" is also meant to denote that the third nucleotide of a codon can be replaced by another nucleotide so that the codon containing the substitution encodes for the same amino acid residue as did the unsubstituted codon. Such redundancy of different codons being translated to the same amino acid residue is well known in the art.

The term "substantially pure" as used herein refers to a biological substance substantially free from all heterogeneous or extraneous matter.

When used in a context describing or depicting nucleotide sequences, the purine or pyrimidine bases forming the nucleotide sequence are depicted as follows:

A—deoxyadenyl
G—deoxyguanyl
C—deoxycytosyl
T—deaxythymidyl

In describing a nucleotide sequence each three-letter triplet constituted by the bases identified above represents a tri-nucleotide of DNA (a codon) having a 5'-end on the left and a 3'-end on the right.

The amino acid residues and amino acid residue sequences of the proteins described herein are depicted by their three-letter or single-letter symbols that are identified and correlated in the Table of Correspondence below:

Table of Correspondence
SYMBOLS FOR AMINO ACIDS

|  | Three-Letter | Single-Letter |
| --- | --- | --- |
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Amino acid residues of proteins and polypeptides are in their natural, L, configurations.

I. GENERAL DISCUSSION

The present invention is directed to a biochemical reagent system-and to methods of preparing and using same, as well as to diagnostics utilizing the reagent system. The reagent system comprises (a) a receptor raised in an animal host to endothelial cell type plasminogen activator inhibitor or to a substantially pure, recombinant molecule described hereinafter, and (b) an indicating means.

The present invention also contemplates methods of forming a polyclonal receptor and a biochemical reagent system of the invention.

The method of forming a polyclonal receptor for use in a biochemical reagent system of the present invention comprises administering to an animal host, preferably a mammal (e.g., a rabbit, goat or horse) an endothelial (beta-) plasminogen activator inhibitor (PAI) or substantially pure, recombinant molecule described herein in an amount sufficient to induce the production of antibodies to the inhibitor. The resulting antibodies constitute receptor molecules for the inhibitor. Antisera containing the antibodies are then collected from the immunized host and the receptor so produced is recovered.

The biochemical reagent system of the invention is formed by combining the receptor molecules formed as described above with an indicating means. Suitable indicating means are those previously described hereinbefore. It is particularly preferred that the indicating means be a separate molecule.

A further embodiment of the invention is a solid phase assay method for directly detecting the presence, and if desired, quantity of endothelial cell type plasminogen activator inhibitor in a sample to be assayed. One aspect of the method comprises the steps of: (a) providing a solid matrix on which to assay a sample; (b) affixing on the solid matrix a binding reagent that binds (complexes with) to the inhibitor to form a solid phase support; (c) admixing an aliquot of a liquid sample to be assayed with the solid phase support to form a solid-liquid phase admixture; (d) maintaining the admixture under biological assay conditions for a predetermined time (typically about 2 to 4 hours) sufficient for the binding reagent to bind to (complex with) endothelial cell type plasminogen activator inhibitor present in the sample; (e) separating the solid and liquid phases; and (f) determining the presence of inhibitor that bound to (complexed with) the binding reagent.

The presence of the inhibitor that complexed with the binding reagent can be determined in a number of ways that depend upon the type of assay direct or indirect/competitive (hereinafter), used. In one preferred embodiment for a direct assay, that determination is made by the steps of (i) admixing an aqueous liquid solution of second binding reagent that binds to the inhibitor of the sample bound on the solid support with the solid phase obtained after step (e) above to form a second solid-liquid phase admixture, the second binding reagent complexing with the inhibitor; (ii) maintaining the second solid-liquid admixture under biological assay conditions for a predetermined time sufficient for the second binding reagent to bind (form a complex) with the inhibitor (typically about 2 to about 4 hours); (iii) separating the solid and liquid phases of the second solid-liquid phase admixture; and (iv) determining the quantity of the second binding reagent that bound to the inhibitor, and thereby determining the quantity of inhibitor.

The amount of second binding agent that binds to or complexes with the inhibitor is typically determined by an indicating means, as described hereinbefore. The indicating means can be linked to the second binding reagent so that the second binding agent and indicating means are one molecule. More preferably, the second binding reagent and indicating means are separate molecules.

Thus, where the indicating means is linked to the second binding reagent, the above method for determining the presence of inhibitor complexed with the first-named binding reagent can be carried out using the steps of (i) admixing an aqueous, liquid solution of second binding reagent containing a linked indicating means with the solid phase obtained after step (e) above to form a second solid-liquid phase admixture, the second binding reagent binding to (complexing with) the inhibitor, and the indicating means providing a means of determining the quantity of the second binding reagent that bound to the inhibitor; (ii) maintaining the admixtures under biological assay conditions for a predetermined time sufficient for the second binding reagent to bind to (complex with) the inhibitor; (iii) separating the solid and liquid phases of the second solid-liquid phase admixture; and (iv) determining the quantity of second binding reagent that bound to the inhibitor.

The indicating means is a separate molecule in particularly preferred practice. In such situations, the bound (complexed) inhibitor can be determined by the steps of (i) admixing a liquid solution of second binding reagent with the solid phase obtained after step (e) above to form a second solid-liquid phase admixture, the second binding reagent binding to (complexing with) the inhibitor; (ii) maintaining the admixture so formed under biological assay conditions for a predetermined period of time sufficient for the second binding reagent to bind to (complex with) the inhibitor; (iii) separating the solid and liquid phases of the second solid-liquid phase admixture; (iv) admixing a separate molecule indicator labeling means (as discussed hereinbefore) to form a third solid-liquid phase admixture; (v) maintaining the third solid-liquid phase admixture under biological assay conditions for a predetermined period of time sufficient for the second binding reagent and indicator labeling means to bind (typically about 2 to about 4 hours); (vi) separating the solid and liquid phases of the third solid-liquid phase admixture; and (vii) determining the amount of separate molecule indicator labeling means that bound to the second binding reagent.

Details for the above embodiment are given hereinafter wherein the first binding reagent is t-PA or u-PA, the second binding reagent is rabbit anti-inhibitor antibody and the separate molecule indicator means is a goat anti-rabbit IgG antibody.

In yet another method, the amount of inhibitor reacted or complexed with the first binding reagent can be determined without the use of a second binding reagent. In this embodiment, the indicator labeling means is linked directly to the inhibitor, and the amount of inhibitor is determined by that label.

For example, the proteins present in a sample to be assayed can be radiolabelled with 125-iodine following one of the procedures described hereinafter. After separation of the solid and liquid phases of step (e), hereinbefore, the radiolabelled, but unbound, proteins are removed from the admixture thereby leaving radiolabelled, bound inhibitor on the solid support. The presence and amount of that bound, radiolabelled inhibitor can then be determined using a gamma counter. A similar result can be obtained using a reactive fluorescent molecule as the indicator labeling means such as fluoroscein isocyanate to react with the components of the assayed sample in place of the radioactive element.

Preferred first and second binding reagents include tissue-type and urokinase-type plasminogen activators or the before described receptor of the invention. If the first binding reagent utilized is tissue-type or urokinase-type plasminogen activator, then the second binding reagent is the receptor.

Alternatively, if the first binding reagent utilized is the receptor, then the second binding reagent is one of the above plasminogen activators. Thus, the first binding reagent is (a) a plasminogen activator selected from the group consisting of t-PA and u-PA, or (b) a receptor of this invention that binds to the inhibitor, and the second binding reagent is (a) a plasminogen activator selected from the group consisting of t-PA and u-PA, or (b) a receptor of this invention. However, the first and second binding reagents are different. Thus, the second binding reagent can also be refered to as the other of (a) and (b) not used as the first binding reagent.

The separate molecule indicator labeling means is preferably used where the second binding reagent is an intact or substantially intact antibody receptor of this invention that binds to the inhibitor. As such, the separate molecule indicator labeling means is preferably an antibody such as goat anti-rabbit IgG or protein A having a linked indicating group such as a radioisotope, enzyme or fluorochrome dye.

A competitive assay is utilized in another aspect of the invention. Here, a solid support is provided that comprises a solid matrix having the substantially pure recombinant, proteinaceous molecule (described hereinafter) affixed thereto. An aliquot of a liquid sample to be assayed for natural (native) endothelial cell type PAI is admixed with a predetermined amount of binding reagent that binds to both (1) the recombinant inhibitor affixed to the matrix as part of the solid support and (2) the inhibitor to be assayed. Exemplary of such binding reagents are the aforementioned receptor molecules and also t-PA and u-PA. The admixture so formed is maintained under biological assay conditions for a predetermined period of time sufficient for the binding reagent to bind to any inhibitor present in the sample to form a complex.

That admixture is then admixed with the before-described solid support to form a solid-liquid phase admixture. The solid-liquid phase admixture is maintained under biological assay conditions for a predetermined period of time sufficient for any binding reagent of the admixture not bound to inhibitor molecules of the sample to bind to the recombinant inhibitor molecules of the solid support.

The solid and liquid phases are then separated, as by decantation and rinsing. The liquid phase and its contents can be retained and assayed as by SDS-PAGE or reverse fibrin autography to provide a direct determination of the presence of beta-PAI. More preferably, an indirect determination is made in which the presence (amount) of human endothelial PAI in the sample is determined by assaying the amount of binding reagent complexed with the solid phase recombinant human endothelial PAI, and comparing that amount with known standards to arrive at a qualitative, and if desired, quantitative determination by difference.

The determination of the amount of binding reagent bound to the solid phase is carried out using the general methods discussed before, except that the second binding reagent is a different molecule from those utilized above. Thus, where the first binding reagent is t-PA or u-PA, the second binding reagent typically is a label-linked antibody raised to either appropriate protein. Where the first binding reagent is a receptor, the second binding reagent typically is a label-linked antibody raised in a host animal different from that in which the first binding reagent receptor molecules were raised, such as goat anti-rabbit antibodies where rabbit anti-beta-PAI antibodies are the first binding reagent. Label-linked protein A is also useful in this indirect, competition assay. It is noted that label-linked receptor molecules can also be used as the first binding reagent, thereby eliminating the need for use of second binding reagent.

The before-described solid phase assay methods are particularly preferred. However, it is to be understood that liquid phase (homogeneous) assays are also contemplated. Such systems are well known in the art and need not be described in detail.

Briefly, however, liquid systems can also utilize a receptor, u-PA or t-PA as the first binding agents of the assay. The indicating means for such systems typically is an antibody that is linked to a signalling enzyme in such a way that binding of the antibody to its substrate in the complex formed inhibits the activity of the linked enzyme, thereby indicating the presence of a complex ingredient to which the antibody binds. Exemplary labeling means for such assays are illustrated in U.S. Pat. No. 3,817,837, No. 3,996,345. A plasminogen activator such as t-PA can also be utilized as a labeled first binding agent when linked to an enzyme whose activity is inhibitable by the formation of a t-PA/human beta-PAI complex. Such a labeling system is thus in some ways analogous to the enzyme-hapten systems described in U.S. Pat. No. 3a,875,011.

The present invention further contemplates a diagnostic system, that can be in the form of a kit, for detecting the presence and quantity of beta-migrating, human plasminogen activator inhibitor in a sample. The kit includes at least one package containing (1) as an active ingredient, an effective amount of the biochemical reagent system of the invention in dry, solution, or dispersion form, and (2) t-PA or u-PA.

The diagnostic system can also include a solid matrix that can be a microtiter strip or plate having a plurality of wells. The t-PA or urokinase present is preferably bound to the solid matrix.

Suitable solid matrices useful in the diagnostic system and methods described hereinbefore include 96 well microtiter plates sold under the designation Falcon Microtest III Flexible Assay Plates (Falcon Plastics, Oxnard, Calif.) and microtiter strips sold under the designation Immulon I and II (Dynatech, Alexandria, Va.). The microtiter strip or plate is made of a clear plastic material, preferably polyvinyl chloride or polystyrene. Alternative solid matrices for use in the diagnostic system and methods include polystyrene beads, about 1 micron to about 5 millimeters in diameter, available from Abbott Laboratories, North Chicago, Ill.; polystyrene tubes, sticks or paddles of any convenient size; and polystyrene latex whose polystyrene particles are of a size of about 1 micron and can be centrifugally separated from the latex.

The solid matrix can also be made of a variety of materials such as cross-linked dextran, e.g. Sephadex G-25, -50, -100, -200 and the like available from Pharmacia Fine Chemicals of Piscataway, N.J., agarose and cross-linked agarose, e.g. Sepharose 6B, CL6B, 4B, CL4B and the like also available from Pharmacia Fine Chemicals.

The agarose or Sepharose matrices are typically activated for linking using cyanogen bromide. The activated matrix is then washed with one molar glycine and linked to the biochemical reagent system of the invention, t-PA or u-PA without drying of the activated matrix (solid support). The matrix-linked reagent system, t-PA or u-PA is then washed and is ready for use. Further details of use of these solid matrices are provided in Section III, A2.

The diagnostic system can further include a standard against which to compare the assay results and various buffers in dry or liquid form.

An indicating means such as those described hereinbefore is preferably supplied along with the receptor in the biochemical reagent system of the invention, and can be packaged therewith when linked to the receptor or more preferably is packaged separately when a separate molecule indicating means is used. Additional reagents such as hydrogen peroxide and diaminobenzidine can also be included in the system when an indicating group such as HRP is utilized. Such materials are readily available in commerce, as are many indicating groups, and may not be supplied along with the diagnostic system. In addition, some reagents such as hydrogen peroxide can decompose on standing, or are otherwise short-lived like some radioactive elements, and are better supplied by the end-user.

The data from several studies, discussed hereinafter, were performed to assess the nature of the plasminogen activator inhibitor and the ability of the biochemical reagent diagnostic systems of the present invention to detect and quantify plasminogen activator inhibitor bound to plasminogen activator in human serum.

The diagnostic system of the invention is based upon the ability endothelial cell type PAI to bind to t-PA or u-PA immobilized on plastic microtiter wells. After washing, the extent of binding is quantified by admixing and maintaining (incubating) the complex first with rabbit antiserum to the inhibitor and then with $^{125}$I-goat anti-rabbit IgG. Using a diagnostic system and assay method of the present invention, it was found that the reaction between t-PA and the inhibitor was rapid (greater than 78 percent binding within 1 hour), time-and concentration-dependent, and sensitive over a broad range of inhibitor concentrations [1–100 nanograms per milliliter (ng/ml)]. Exogenously added t-PA and u-PA were found to compete with the immobilized t-PA for the inhibitor with a 50 percent reduction in binding obtained with 12 ng/ml of t-PA and 6 ng/ml of u-PA.

It is to be understood that the results discussed hereinafter are illustrative of embodiments utilizing the biochemical reagent and diagnostic systems of the present invention and the present invention is not intended to be so limited.

A biologically pure DNA molecule that codes for human endothelial cell type PAI or a fusion polypeptide containing that PAI, i.e., a proteinaceous molecule that is immunologically similar to that PAI, constitutes a further aspect of the invention. That DNA molecule contains about 1140 to about 3000 nucleotides or nucleotide base pairs (bp) and includes a nucleotide sequence that consists essentially of the nucleotide sequence corresponding to a nucleotide sequence represented by the formula of FIG. 22, from left to right and in the direction from 5'-terminus to 30 3'-terminus (51-end to 3'-end). The reading frame of a nucleotide sequence of the invention must, of course, be consistent with that of human endothelial cell type PAI or a fusion polypeptide containing endothelial cell type PAI. Thus, the reading frame must not shift, but must be the same as that in which the nucleotide residue at position 13 shown in FIG. 22 is the first nucleotide residue of a triplet codon.

A suitable DNA molecule includes a nucleotide sequence that corresponds to the depicted sequence from nucleotide position 13 to about position 1153. Other suitable DNA molecules include DNA sequences corresponding to the depicted sequences from nucleotide position 1 to about nucleotide position 1153, from nucleotide position 1 to about nucleotide position 1960, as well as the entire sequence shown in FIG. 22 from nucleotide position 1 to about nucleotide position 2995.

A nucleotide sequence of this invention consists essentially of one of the before-described sequences. Thus, a nucleotide sequence of the invention excludes additional nucleotides that affect the basic and novel characteristics of a nucleotide sequence that codes for human endothelial PAI.

A nucleotide sequence of the invention can include one or more transcriptional promoter sequences operationally linked to the sequence adjacent to the 5'-terminus thereof.

Where translation of the DNA and protein expression are desired, the DNA also includes a translation initiating codon (ATG) and a translation terminating codon (TAA or TAG or TGA), each operationally linked adjacent to the 5'-terminus and 3'-terminus, respectively, of the sequence, with the translation initiating codon being located between the promoter sequence and the 5'-terminus.

A DNA sequence that codes for all or a portion of another molecule can also be included in the DNA molecule so that the translated (expressed) proteinaceous molecule is a fusion polypeptide that includes an amino acid residue sequence of all or a portion of that other molecule fused (linked by a peptide bond) to the expressed, human endothelial PAI. An exemplary fusion polypeptide is the proteinaceous molecule discussed hereinafter that contains a portion of the beta-galactosidase molecule fused to the amino-terminus of human endothelial cell PAI. That molecule also includes four amino acid residues of the PAI leader peptide fused by peptide bonds between the beta-galactosidase portion and the PAI sequence.

All of the above nucleotide sequences can be present so long as an enumerated DNA molecule remains replicable, where only replication is desired. Where replication and translation (proteinaceous molecule expression) are desired, those nucleotide sequences are present so long as the DNA molecule remains replicable and the proteinaceous molecule containing the amino acid residue sequence of human, endothelial cell PAI expressed exhibits immunological cross-reactivity (discussed hereinafter) with the naturally occurring bovine and human endothelial PAI described herein. The expressed proteinaceous molecule also preferably binds to t-PA and exhibits inhibition of at least t-PA in a reverse fibrin autography assay as discussed herein. Most preferably, that expressed molecule also binds to and exhibits inhibition of u-PA activity in the reverse fibrin autography assay.

Since a nucleotide sequence of the invention contains a nucleotide sequence that corresponds to a sequence whose formula is represented in FIG. 22, conservative codon substitutions as well as conservative nucleotide substitutions are contemplated, as those phrases are defined herein.

A nucleotide sequence of the invention can be single-stranded as is shown in FIG. 22. Most preferably, however, a DNA sequence is linked by hydrogen bonds to a second DNA molecule, the second DNA molecule having a nucleotide sequence that is complementary and in antiparallel orientation to the first-named DNA. Thus, most preferably, a DNA of the invention is double-stranded and contains a before-described DNA sequence corresponding to all or an enumerated portion of the sequence shown in FIG. 22 along with a complementary sequence.

A non-chromosomal vector for propagation and expression of a desired DNA nucleotide sequence as defined hereinabove in a replication/expression medium, e.g., a unicellular organism or the like such as E. coli, S. cerevisiae or mammalian cells such as COS cells, is also contemplated. That vector comprises a replicon that is compatible with the replication/expression medium and contains therein the DNA molecule to be replicated in a manner such that the vector can propagate the DNA molecule.

In addition, the non-chromosomal vector also includes those sequence components that are utilized for transcription and translation. To that end, a transcriptional promoter can be operationally linked to the DNA molecule present adjacent to the 5'-terminus thereof, as already noted. The transcriptional promoter can be endogenous to the vector or exogenous to the vector. A transcriptional promoter endogenous to the vector such as the lac Z promoter-operator utilized herein is preferred. A translational terminator can also be operationally linked adjacent to the 3'-terminus of the DNA molecule in some instances, although the nucleotide sequence represented by the formula of FIG. 22 contains such a terminator sequence.

A before-defined DNA of FIG. 22 molecule lacks an initiation codon (ATG) adjacent to the 5'-terminus of the sequence that begins translation in a replication/expression medium. Such a codon can be ligated to a defined DNA molecule in frame, as discussed hereinbefore, or can be a portion of the vector nucleotide sequence as exemplified herein.

Human endothelial PAI is an excreted protein, and thus as expressed naturally, contains a so-called polypeptide leader or signal sequence that assists in migration of the protein through the plasma membrane, and that is excised in a post-translational event. Only a portion of the encoded polypeptide leader sequence of human endothelial PAI is included in a before-defined DNA molecule sequence. The examplary DNA molecule illustrated herein is expressed within the cytoplasm of replication/expression medium such as E. coli, as compared to the periplasmic space of the cells. Expression into the cytoplasm of E. coli is usual for that replication/expression medium.

The before-discussed transcription promoter, translation initiating and translation terminating codons and sequence coding for a polypeptide leader sequence, where used, are normally parts of the non-chromosomal vector as compared to a DNA molecule of the invention. For use in expression of the proteinaceous molecule, the vector normally also includes a ribosome binding site (Shine-Delgardo sequence) adjacent to the 5'-terminus of the DNA molecule and located upstream from the initiation codon, as is well known. The vector's promoter such as the lacZ promoter utilized herein typically contain a ribosome binding site.

Thus, the nucleotide sequence of the vector, aside from those nucleotides needed for the replication and general vector function include, in frame and from 5'-terminus to 3'-terminus, a ribosome binding site operationally linked adjacent to the 5'-terminus of a transcription promoter; that promoter operationally linked to the 5'-terminus of the translation initiating codon; that codon operationally linked to the 5'-terminus of: (a) a leader sequence for expression in eukaryotes, or (b) a sequence of a portion of another molecule that is expressed as a fusion polypeptide with the desired human endothelial PAI, or (c) a DNA molecule of this invention; where (a) or (b) is present, that sequence is operationally linked to the 5-terminus of a DNA molecule of this invention. The DNA molecule of this invention, however linked adjacent to its 5'-terminus, is linked adjacent to its 3'-terminus to a translation terminating codon. As is apparent from examination of FIG. 22, additional nucleotides can also be present operationally linked to the 3'-terminus of the terminating codon so long as those additional nucleotides do not interfere with transcription and/or translation, as those events are desired, or can interfere with the immunological similarity of an expressed proteinaceous molecule to human or bovine endothelial PAI. Most preferably, any additional nucleotides also do not interfere with the biological activity toward plasminogen activators exhibited by an expressed proteinaceous molecule.

It is to be understood that all of the DNA sequences of the vector must be compatible with the replication/expression medium utilized for replicating the DNA, and more preferably expressing a product coded for (encoded by) a DNA molecule of this invention. A vector of the invention is at least capable of replicating (propagating) a DNA molecule of the invention. More preferably, the vector is capable of not only replicating a DNA molecule, but is also capable of expressing or translating the genomic information of that DNA into a recombinant proteinaceous molecule that is immunologically similar to human endothelial PAI, as defined herein.

A non-chromosomal vector of this invention need not be limited to those vectors useful for replicating and translation (expression) in *E. coli* as host replication/expression medium. Substantially any vector useful for replicating (propagating) a DNA sequence can be utilized for replicating the DNA, e.g. in mammation or eukaryotic cells.

A wide range of such vectors is commercially available as are appropriate host replication media. Exemplary vectors, both plasmids and bacteriophages and hosts are available from the American Type Culture Collection of Rockville, Md., and are listed in its *CATALOGUE OF BACTERIA, PHAGES AND rDNA VECTORS*, sixteenth ed., 1985. In addition, plasmids, cosmids and cloning vectors are listed as being available in catalogues from Boehringer Mannheim Biochemicals of Indianapolis, Ind.; Bethesda Research Laboratories, Inc. of Gaethersberg, Md., and New England Biolabs, Inc. of Beverly, Mass.

Another aspect of the invention is a substantially pure, recombinant proteinaceous molecule that is immunologically similar to human endothelial cell type plasminogen activator inhibitor; that is, antibodies raised to the recombinant molecule immunoreact with native human endothelial cell type plasminogen activator inhibitor. As already noted, the recombinant molecule need only have the amino acid residue sequence of the native molecule to be useful in inducing the secretion of cross-reactive antibodies that are useful in assays. As such, this molecule can be translated from a replication/expression medium containing a vector having an appropriate translational start and preferably stop codons, as already described. The above-described immunological similarity can be demonstrated by inducing antibodies in rabbits following the procedure described hereinafter in section III A 3 for bovine endothelial PAI.

The substantially pure recombinant proteinaceous molecule also preferably possesses some, if not all, of the biological activity of human, endothelial cell type PAI. Such a molecule constitutes another embodiment of this aspect of the invention.

Thus, substantially pure, recombinant human endothelial cell type PAI is also contemplated herein. The recombinant molecule binds to and inhibits the activity of human t-PA as determined by reverse fibrin autography as described herein. The molecule also preferably binds to and inhibits the activity of u-PA.

The recombinant molecule is immunologically different from protease nexin and human placental PAI. An immunological difference between molecules can be assessed in a number of manners and from an antigenic or immunogenic viewpoint. Most easily, however, the immunological difference between the three molecules is shown by a specific binding study using polyclonal antibodies that bind to the recombinant molecule. Those antibodies are substantially free from specific binding with either protease nexin or with human placental PAI.

The recombinant human endothelial cell type PAI is immunologically related and similar to bovine endothelial cell type PAI and naturally occurring human endothelial cell type PAI as is evidenced by the fact that polyclonal antibodies raised to the bovine PAI specifically immunoreact with both the recombinant and naturally occurring PAIs. In addition, polyclonal antibodies or other receptors raised to naturally occurring human endothelial PAI immunoreact with bovine and the expressed recombinant PAI molecules. Similarly, polyclonal antibodies or other receptors raised to the recombinant molecule immunologically bind specifically to both naturally occurring bovine and human endothelial cell type PAI molecules. Thus, the expressed, recombinant human endothelial cell type PAI exhibits immunological cross-reactivity with naturally occurring bovine and human endothelial PAI molecules.

The substantially pure recombinant human endothelial cell type PAI is substantially free from extraneous proteins and polypeptides as can be ascertained by SDS-PAGE analysis followed by staining with Coomassie Brilliant blue dye. The desired purity can be achieved, for example, by use of an affinity column or other sorbant containing affixed polyclonal antibodies to bovine endothelial PAI as the sorbing moiety, followed by standard elution and protein purification techniques.

In a particular embodiment, the recombinant human endothelial cell type PAI is substantially free from polypeptide-linked glycosyl groups as is the exemplary fusion polypeptide described herein. Such molecules are typically expressed using a procaryotic replication/expression medium such as *E. coli*.

The recombinant human endothelial cell type PAI can also contain polypeptide-linked glycosyl groups. The glycosylated molecule is typically expressed from eukaryotic cells as replication/expression medium such as mammalian Chinese hamster ovary (CHO) cells or COS cells using for example an SV40-derived or other vector, as is well known.

An eukaryotic replication/expression medium and appropriate vector such as CHO cells and an SV40-derived vector or a yeast replication/expression medium such as *S. cerevisiae* and appropriate vector such as a vector derived from pTDT1 are also particularly useful where the expressed recombinant molecule is desired to be excreted into the culture medium. A nucleic acid sequence that encodes a leader or signal peptide sequence is used for expression of the recombinant molecule into the culture medium.

As discussed previously, other genetic signals can be included in the constructs to facilitate secretion of PAI out of the cell and into the culture medium. This improves the purification procedure. In both prokaryotic and eukaryotic systems a "leader peptide" at the amino-terminus of the protein acts as a signal for secretion. This leader peptide is cleaved off by host cellular protease to form the mature protein.

To generate such a protein containing a leader sequence, "fusion" polypeptides are constructed in which the nucleotide coding region for the leader peptide of a known secreted protein is ligated in the same reading frame to the 5'-terminus of the coding region of the PAI to be expressed and secreted. Because the cleavage signals are resident on the leader peptide and the cleavage dependent protease is in the host, normal secretion results.

This fusion protein strategy has been applied successfully in both yeast and in CHO cells. For example, Filho et al., *Biotechnology* 4:311, 1986 describe a construct for yeast expression in which the leader peptide from yeast alpha factor including the protease cleavage signal is fused to the eukaryotic protein mouse alpha-amylase, is driven by the alpha factor promoter and results in secretion into the medium of mature protein. Other similar constructs using the alpha factor gene promoter have been reported to express foreign proteins in yeast [Bitter et al., *Proc. Natl. Acad. Sci. USA.*, 81:5530 (1984); Brake et al., *Proc. Natl. Acad. Sci. USA.*, 81:4642, (1984); and Singh et al., *Nucleic Acid Res.* 12:8927 (1984)].

In mammalian cell expression systems, the leader peptide from Herpes Simplex Virus glycoprotein D has been fused to portions of the envelope glycoprotein from HTLV III. The fusion polypeptide was secreted in CHO cells (Lasky et al., *Science*, 233:209 (1980).

Methods to increase production have been reported in which the copy number of the transfected plasmid is maintained at a high number per cell. This is accomplished by including a selectable marker such as a dihydrofolate reductase (dhfr) on the expression plasmid and culturing the transformed cells that are deficient in dhfr in the presence of medium that requires high levels of dhfr for growth [Simonsen et al., *Proc. Natl. Acad. Sci. USA*, 80:2495 (1983)]. Similarly, an SV40 based vector such as pKSV-10 that contains an SV40 origin of replication can be maintained in COS cells at a high copy number because the COS cells also contain a defective SV40 viral genome that preferentially stimulates the expression vector's SV40 origin to replicate autonomously in the host cell's cytoplasm [Gluzman, *Cell*, 23:175 (1981)].

In addition, as already noted, the recombinant protein can be expressed in several forms. In one embodiment, it is expressed as a protein whose amino acid residue sequence is that represented by the inferred formula shown in FIG. 22 from about amino acid residue position 1 (DNA nucleotide numbers 13–15) through amino acid residue position 379 (DNA nucleotide numbers 1154–1157). When so expressed and substantially free of polypeptide-linked glycosyl groups, the recombinant protein exhibits an apparent relative molecular mass ($M_r$) of about 40,000 daltons [40 kilodaltons (kda)] as determined by SDS-PAGE analysis. In another embodiment, the PAI is expressed as part of a fusion polypeptide having an $M_r$ of about 180 kda by SDS-PAGE analysis, and containing a portion of the beta-galactosidase molecule operationally linked by a peptide bond to the amino-terminal amino acid residue whose formula is shown at amino acid residue position −4 (nucleotide positions 1–3) in FIG. 22. Both of those exemplary molecules exhibited biological activity similar to that of human endothelial cell plasminogen activator inhibitor in that they were capable of binding to and inhibiting the activity of u-PA in reverse fibrin autography, as is discussed hereinafter and illustrated in FIG. 21. The recombinant protein can also be expressed with an amino-terminal leader polypeptide sequence, as already described.

As is apparent from the previous discussion, the substantially pure, recombinant human endothelial cell type PAI is useful in solid phase competitive assay systems when affixed to a solid matrix as a part of a solid support. That recombinant PAI is also useful as an immunogen used to raise antibodies for use as receptor molecules in other assay systems. This latter use is similar to the use of the substantially pure recombinant proteinaceous molecule that need not have biological activity.

When so used, and particularly when used affixed to a solid matrix as part of a solid support in an assay, it is not of great import that the protein or fusion polypeptide be substantially free of bacterial lipopolysaccharide (LPS) or other bacterial cellular products as are known to often contaminate proteinanceous materials prepared by recombinant techniques. However, where substantial freedom from LPS is desired, as where the material is utilized as an immunogen, well known techniques can be utilized to prepare the PAI substantially free of bacterial LPS and other bacterial cellular debris. See for example, Issekutz (1983), *J. Imm. Methods*, 61, 271–281 and Sofer, *BIO/TEC-NOLOGY*, December 1984, 1035–1038 and the citations therein. The replication/expression medium can also be adjusted as by use of the yeast *S. cerevisiae* or mammalian cells as discussed before as the expression medium along with a suitable vector as is known.

II. RESULTS

A. Purification of the Bovine Endothelial Cell (BAE) Inhibitor

It had previously been shown that CM (as described in Section III A 1 and 2, hereinafter, and in the following papers) from BAEs contained both tissue-type (t-PA) and urokinase-type (u-PA) plasminogen activators, Levin et al., *J. Cell Biol.*, 94, 631 (1982), as well as an inhibitor of fibrinolysis, Loskutoff et al., *Proc. Natl. Acad. Sci.* (*USA*), 80, 2956 (1983). Fractionation of this M by affinity chromatography on concanavalin A-Sepharose revealed that the u-PA and t-PA; could be separated from each other, Loskutoff et al., *Blood*, 62, 62 (1983), and suggested that this approach also would be useful for the purification of the inhibitor.

One liter of CM was applied to a concanavalin A-Sepharose column and the column was processed as described in Section III hereinafter. The peak fractions were pooled, fractionated by SDS-PAGE, and analyzed for protein by staining with Coomassie Brilliant Blue, and for the presence of fibrinolytic activators and inhibitors by reverse fibrin autography. As shown in FIG. 1, more than 85 percent of the protein applied to the column was recovered in the run-through effluent (pool I). This fraction contained both albumin and u-PA, but no inhibitor. Some inhibitor was detected in Pool III, the fraction containing the majority of recovered t-PA activity, Loskutoff et al., *Blood*, 62, 62 (1983) but represented less than 20 percent of the total inhibitor as judged by the relative size of the lysis-resistance zones, Erickson et al., *Anal. Biochem.*, 137, 454 (1984). The majority of detectable inhibitor activity was recovered in the concanavalin A, pool II fraction, as shown in the inset in FIG. 2, a fraction containing only 5 percent of the total protein. It appeared to comigrate with one of the major stained proteins.

Figure 2:
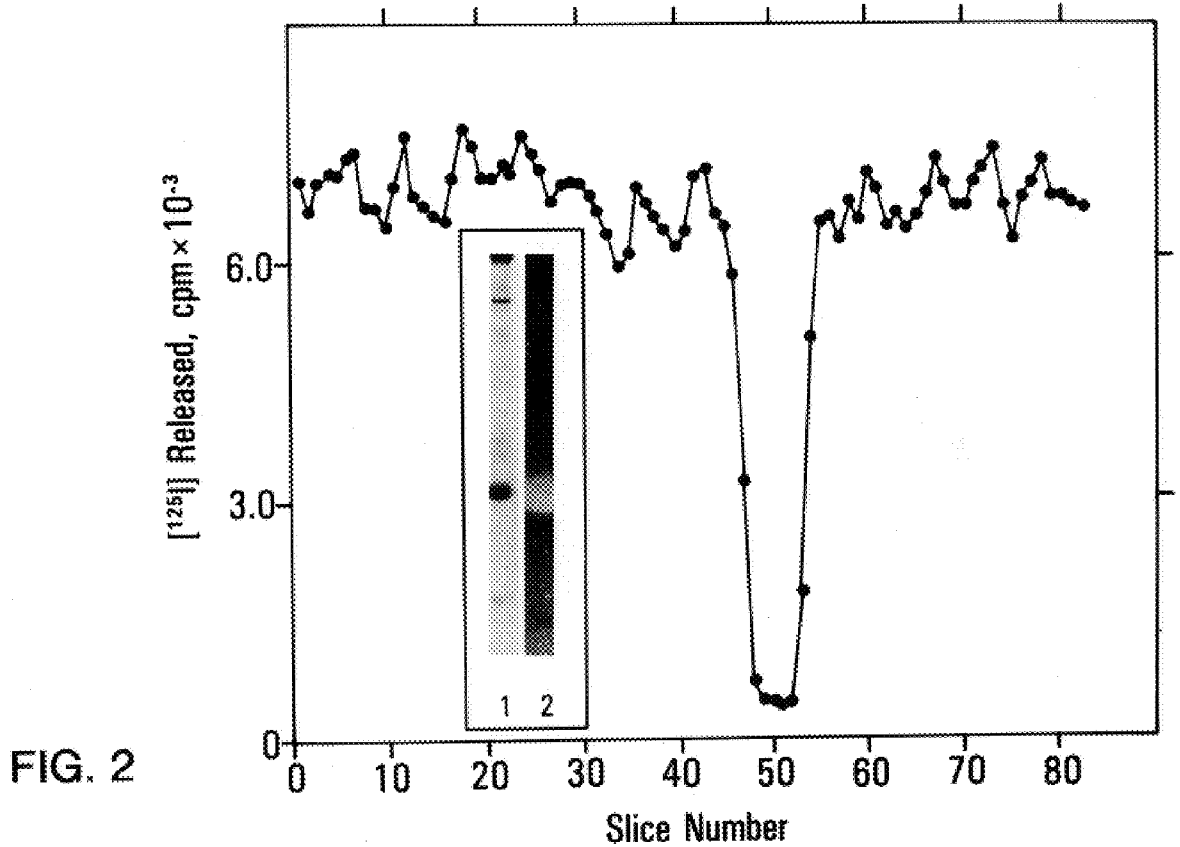
FIG. 2 is a graph illustrating the detection of inhibitor activity of concanavalin A fraction II (above) after SDS-PAGE. The concanavalin A peak II material (FIG. 1) was pooled and fractionated by SDS-PAGE in a tube gel as described in detail hereinafter. The gel was sliced, each slice was eluted into buffer, and then the eluants were tested for their ability to inhibit u-PA-mediated fibrinolytic activity as measured by the $^{125}$I-fibrin plate method (described hereinafter). The inset shows the protein profile (lane 1) and inhibitor activity (lane 2) of similar samples fractionated by SDS-PAGE on slab gels and analyzed by staining with Coomassie Brilliant Blue and by reverse fibrin autography, respectively.

The concanavalin A pool II also was analyzed by SDS-PAGE in tube gels and results are shown in FIG. 2. After electrophoresis, the gel was sliced and extracts of the slices tested for their ability to inhibit u-PA-mediated lysis of $^{125}$I-fibrin. Again, inhibitor activity was detected in a single region of the gel, and migrated with a relative mobility ($R_f$) that was indistinguishable from that of the lysis-resistant zone shown in the inset of FIG. 2 (i.e., $R_f$=0.6). Few other proteins were detected in this region of the gel, suggesting that the purification could be completed by extracting the inhibitor out of such gels.

Figure 3:
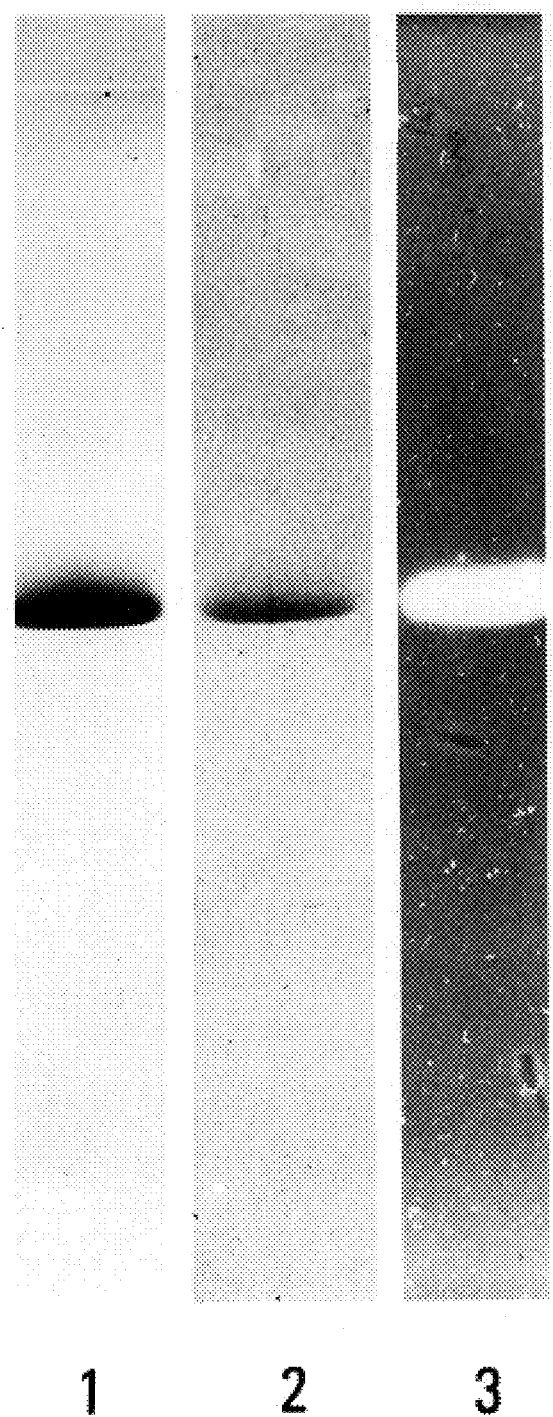
FIG. 3 is a photocopy of a reverse fibrin autogram showing an analysis of purified inhibitor by SDS-PAGE. The gel extracts containing the majority of the inhibitor activity (fractions 49–52 as shown in FIG. 2) were pooled and analyzed on a 7.5–20 percent gradient slab gel as described in detail hereinafter. After electrophoresis, the gel was stained with Coomassie Brilliant Blue (lane 1) and periodic acid-Schiff reagent (lane 2), or tested for inhibitor activity by reverse fibrin autography (lane 3).

The extracts with the highest inhibitor activity (FIG. 2, slices 49–52) were pooled and reanalyzed on 7.5–20 percent gradient gels and the results shown in FIG. 3. A single protein was detected when the gel was stained with Coomassie Brilliant Blue (FIG. 3, lane 1) or periodic acid-Schiff reagent (FIG. 3, lane 2), and it comigrated with the inhibitor as revealed by reverse fibrin autography (FIG. 3, lane 3). The amount of inhibitor antigen present in the starting CM and in the various pooled fractions was determined by the rocket technique of Laurell, Scand. J. Clin. Lab. Invest, 29, 21 (1977), using antisera developed to the purified inhibitor.

These screenings indicated that CM contained 0.6 micrograms/ml (ug/ml) of inhibitor, that 600 micrograms of inhibitor were applied to the concanavalin A column (FIG. 1), and that 90 microgams were recovered from the final gel extracts (FIGS. 2 and 3). Thus, this purification protocol yielded a recovery of approximately 15 percent of the starting antigen. The purified inhibitor had an apparent relative molecular mass ($M_r$) of about 50,000±2,500 daltons under both reducing and non-reducing conditions when compared directly to $M_r$ standards.

B. Preliminary Characterization of the Purified Inhibitor

Figure 4:
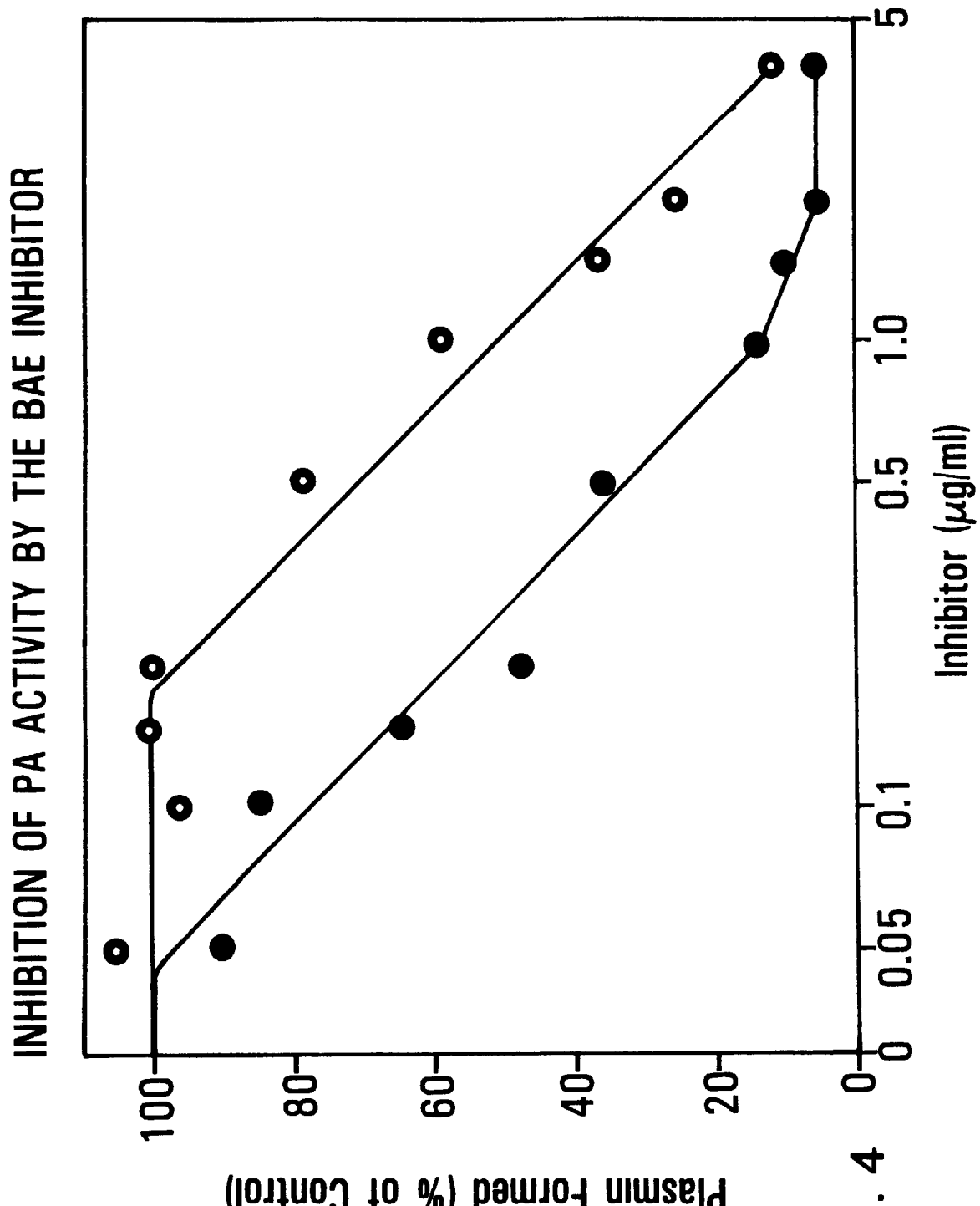
FIG. 4 is a graph illustrating the inhibition of PA activity by the BAE inhibitor. Increasing amounts of the purified inhibitor were preincubated for 5 minutes at 37° C. with 2.5 units/ml of either human u-PA (O) or t-PA (●). $^{125}$I-plasminogen was added, and the incubation continued for another 60 minutes. The reaction was stopped by heating the samples at 100° C. for 3 minutes in the presence of 3 percent SDS and 5 percent 2-mercaptoethanol. The ability of the various samples to cleave the $^{125}$I-plasminogen into its characteristic heavy and light chains was assessed by SDS-PAGE and autoradiography as in Mussoni et al., *Thromb. Res.*, 34, 241 (1984). Quantitation was achieved by excising the $^{125}$I-labeled plasminogen and plasmin chains from the dried gel, and counting them in a gamma counter. The data are expressed as a percentage of plasminogen cleavage observed in the absence of inhibitor.
Figure 5:
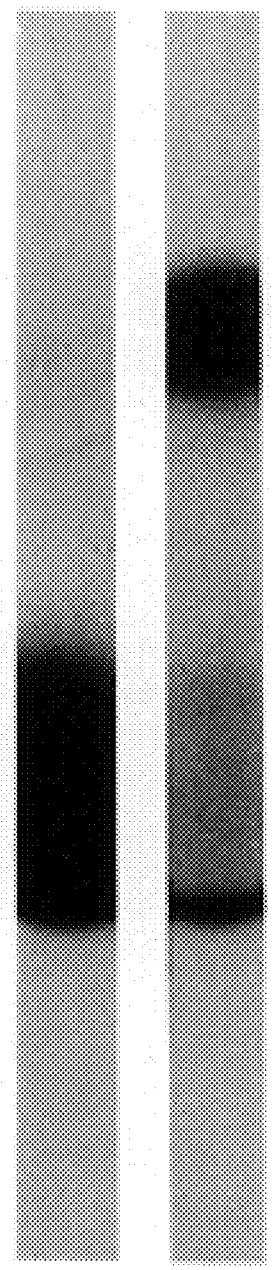
FIG. 5 is a photocopy of an autoradiogram showing the binding of $^{125}$I-labeled t-PA to the BAE inhibitor. $^{125}$I-labeled t-PA was incubated for 30 minutes at 37° C. in the absence (lane 1) or presence (lane 2) of the purified inhibitor (1 microgram/ml). The reaction was stopped by the addition of sample buffer, and the samples were then analyzed by SDS-PAGE and autoradiography.

PAs convert single chain plasminogen into two-chain plasmin by cleavage of a single arginine-valine bond, Summaria et al., J. Biol. Chem., 242, 4279 (1967). This process can be monitored by SDS-PAGE in the presence of reducing agents, Mussoni et al., Thromb. Res., 34, 241 (1984); Summaria et al., J. Biol. Chem., 242, 4279 (1967); Dano et al., Biochim. Biophys. Acta, 566, 138 (1979). To determine whether the inhibitor was an anti-activator, its ability to inhibit this cleavage was assessed and the results shown in FIG. 4. The purified inhibitor blocked the ability of both u-PA and t-PA to cleave $^{125}$I-plasminogen into its characteristic heavy and light chains, and did so in a dose-dependent manner. Inhibition of t-PA was associated with the formation of an enzyme-inhibitor complex that was still apparent after SDS-PAGE as shown in FIG. 5.

Figure 6:
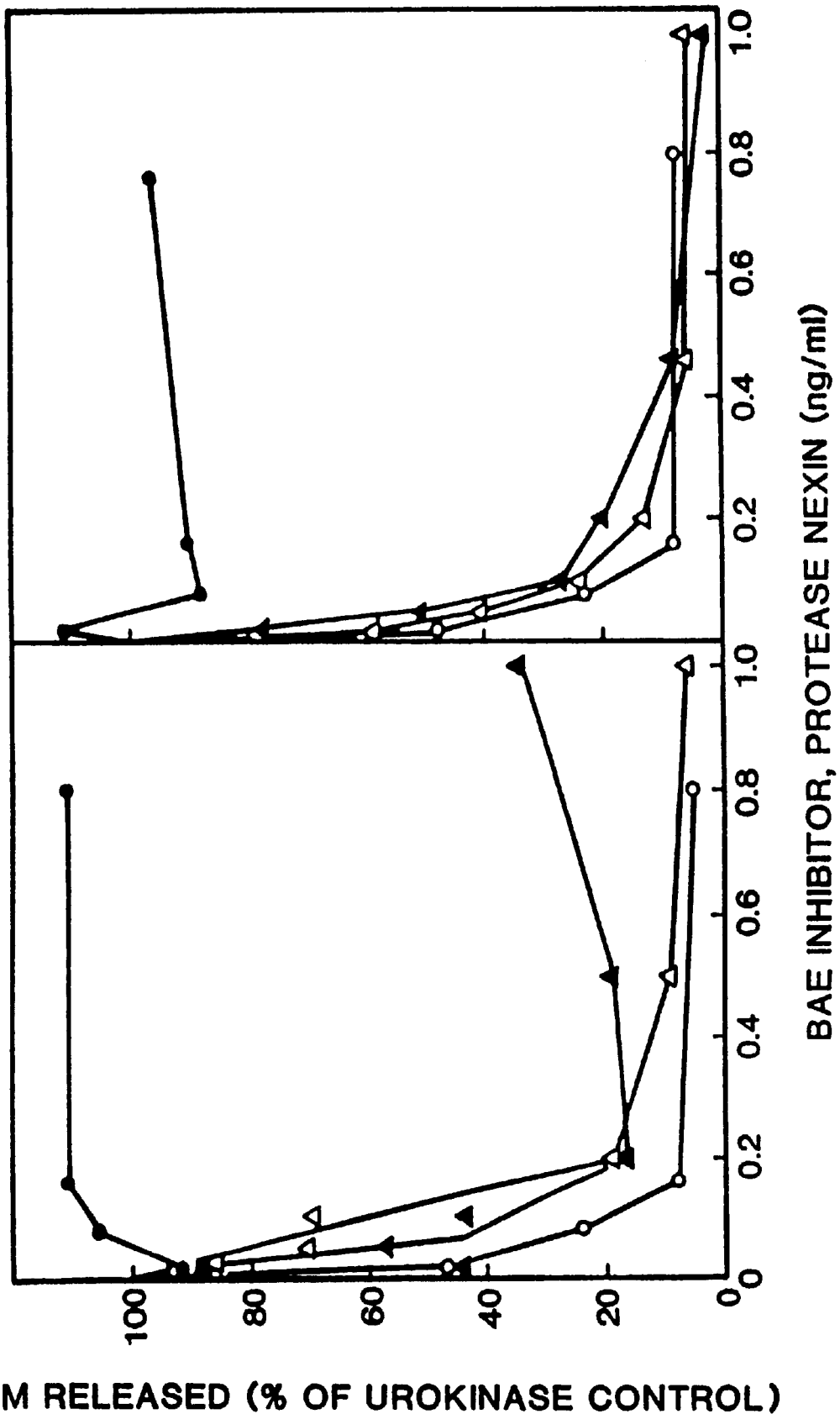
FIG. 6 is a graph illustrating the relative stabilities of the BAE inhibitor and protease nexin. Purified inhibitor (20 micrograms/ml) and purified protease nexin (160 micrograms/ml) were incubated for 60 minutes at 37° C. at pH 2.7 (A) or in the presence of 0.025 percent SDS (B) as described in detail hereinafter. The samples were neutralized by the addition of three volumes of assay buffer, diluted into assay buffer, and tested for residual inhibitor activity by the $^{125}$I-fibrin plate assay (described hereinafter). In control experiments, PBS was substituted for glycine and SDS, respectively. The data are expressed as the percentage of u-PA controls lacking inhibitor. The samples tested included untreated (O) and treated (●protease nexin, and untreated (Δ) and treated (▲) BAE inhibitor.

The inhibitor activity of the purified molecule, like that detected in CM collected from confluent BAEs, Loskutoff et al., Proc. Natl. Acad. Sci. (USA), 80, 2956 (1983), was not destroyed upon incubation at pH 2.7 for 60 minutes at 37° C., or upon exposure to SDS as shown in FIG. 6. In contrast, the inhibitor activity of purified protease nexin was abolished by these same treatments. The inhibitor activity of these proteins was not affected by incubation for 30 minutes at 37° C. in the presence of 5 percent 2-mercaptoethanol.

Figure 7:
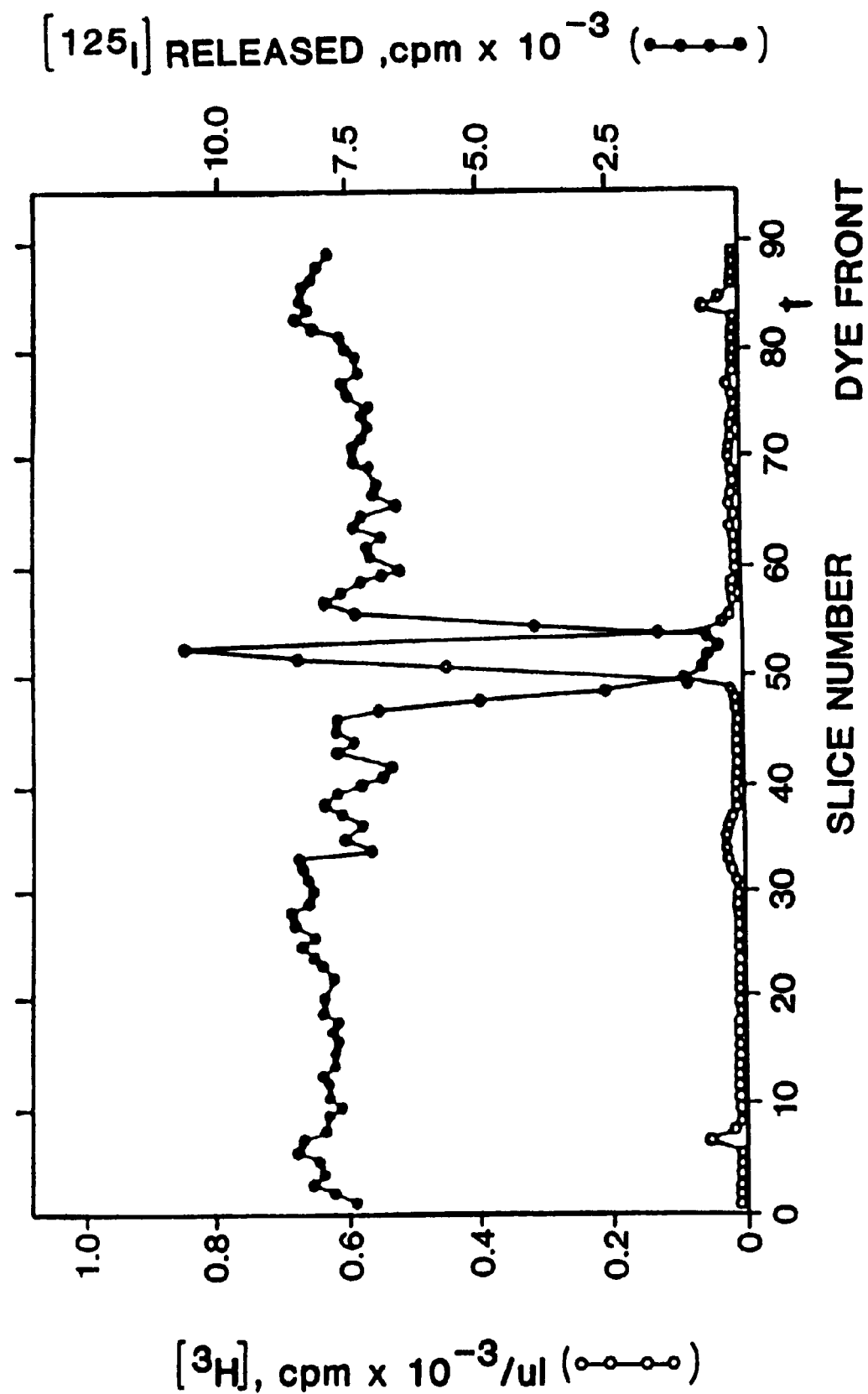
FIG. 7 is a graph illustrating SDS-PAGE of L[3,4,5-$^3$H] leucine labeled concanavalin A fraction II. An aliquot (225 microliters) of the concanavalin A peak II sample was subjected to SDS-PAGE in tube gels. After electrophoresis, the gel was sliced and each of the slices was extracted into buffer as described in detail hereinafter. The resulting gel extracts were tested for inhibitor activity by the $^{125}$I-fibrin plate method (● and for radioactivity by scintillation counting (O) as described hereinafter.
Figure 8:
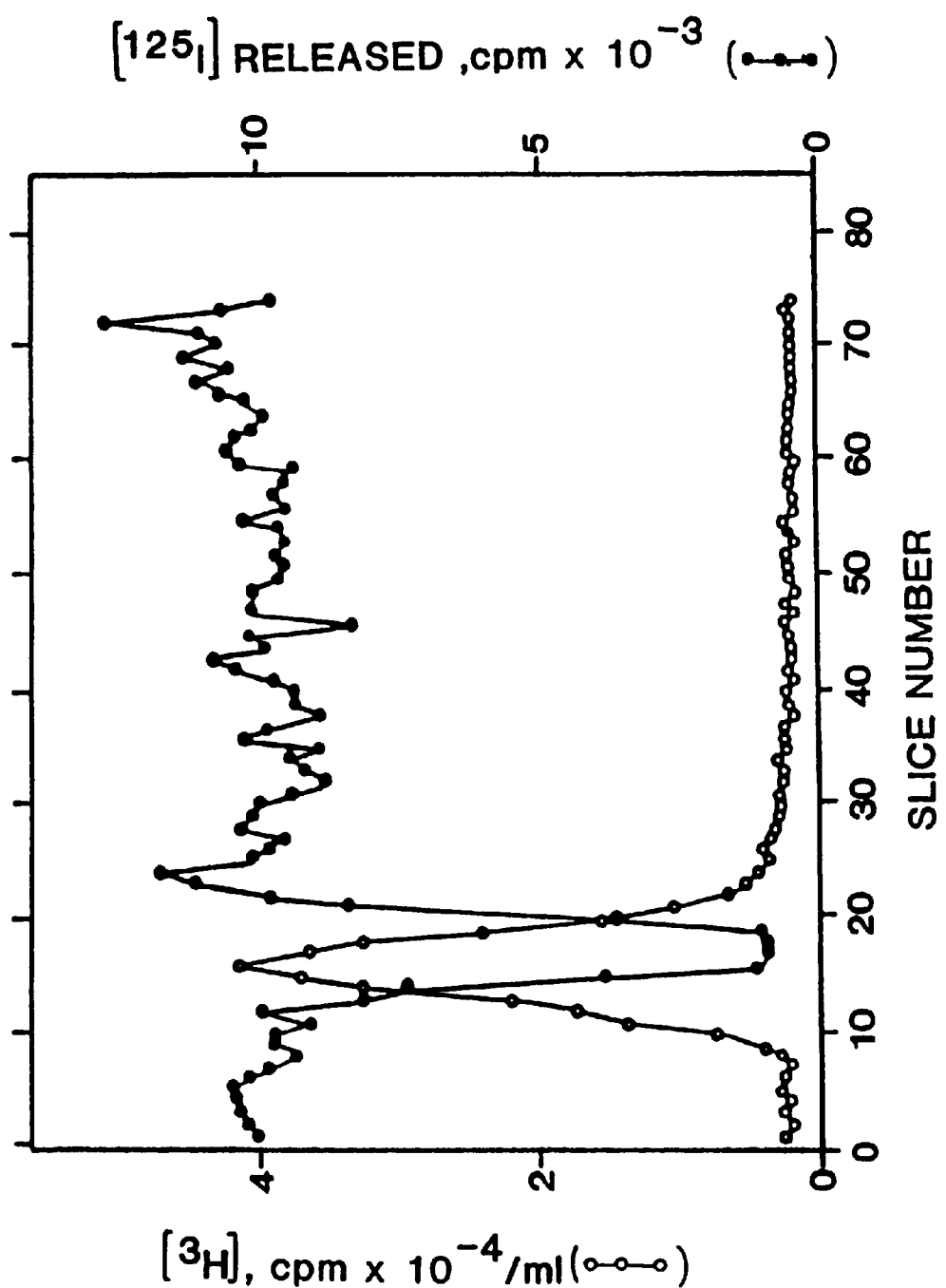
FIG. 8 is a graph illustrating alkaline PAGE of L[3,4,5-$^3$H] leucine labeled inhibitor extracted from SDS gels. The inhibitor fractions after SDS-PAGE (slice extracts 51–54, as shown in FIG. 7) were pooled, combined with albumin to a final concentration of 100 micrograms/ml, and dialyzed against PBS containing 0.5 percent Triton X-100. The sample was then fractionated by alkaline PAGE in tube gels and processed for the determination of radioactivity (O) and inhibitor activity (● as described above for FIG. 7.

C. Purification of the Inhibitor from BAEs Cultured in the Presence of L[3,4,5-$^3$H] Leucine Both plasma and serum contain inhibitors of fibrinolysis, Loskutoff, J. Cell Physiol., 96, 361 (1978); Mullertz, in Progress in Chemical Fibrinolysis and Thrombolysis, Davidson et al. eds., vol. 3, pp. 213–237, Raven Press, New York (1978); Collen, Thromb. Haemostas., 43, 77 (1980). Cultured endothelial cells may internalize or bind these serum proteins and subsequently release them back to the serum-free medium, Cohen, J. Clin. Invest., 52, 2793 (1973); Pastan et al., Cell, 12, 609 (1977); Rohrlich et al.,J. Cell Physiol., 109, 1 (1981); McPherson et al., J. Biol. Chem., 256, 11330 (1981), during the preparation of CM. To determine whether the inhibitor actually was synthesized by BAEs, or was simply a contaminating serum inhibitor, the inhibitor was purified from the CM of cells cultured in the presence of L[3,4,5-$^3$H] leucine, employing the same protocol as that developed for the purification of the inhibitor from unlabeled CM. Two peaks of radiolabeled proteins were recovered when the concanavalin A-Sepharose column was eluted with alpha-methyl mannoside in the presence of low and high salt. The peak II fractions containing inhibitor were pooled and subjected to further analysis by SDS-PAGE and the results shown in FIG. 7. Both inhibitor activity and the majority of the radioactivity were recovered in the same fractions. These two activities also comigrated when the peak inhibitor fractions (fractions 52, 53 in FIG. 7) were pooled, dialyzed, and subjected to subsequent analysis by alkaline PAGE (FIG. 8). Taken together, these data indicated that the inhibitor was a biosynthetic product of the cells, and not a contaminating serum protein.

Figure 9:
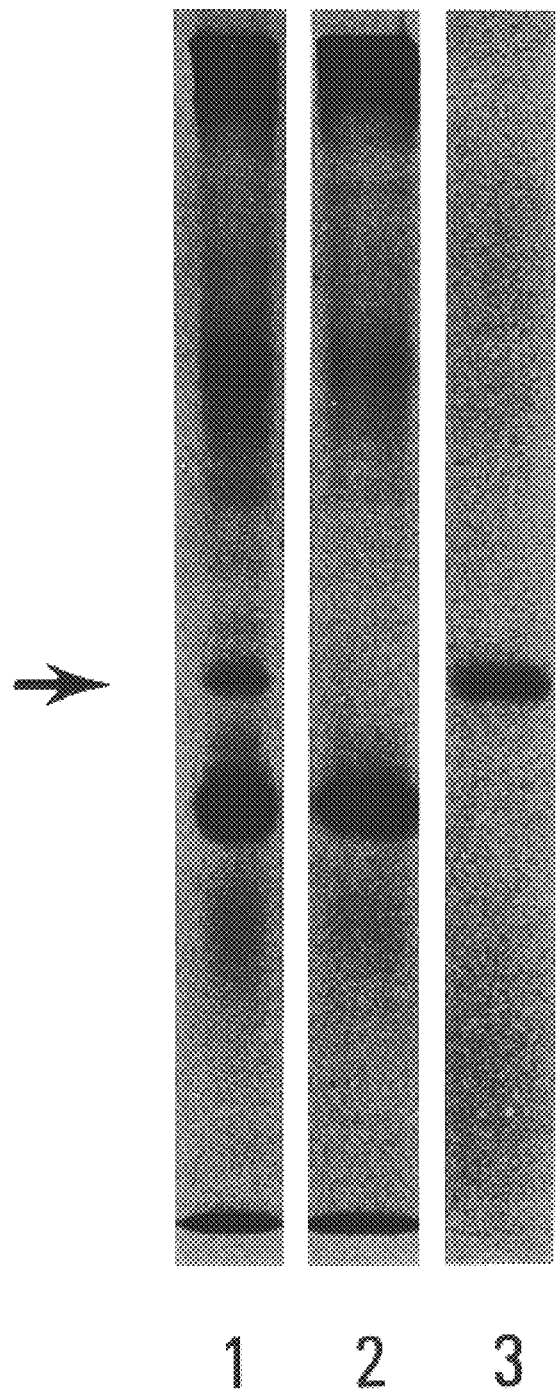
FIG. 9 is a photocopy of an autoradiogram showing immunoprecipitation of inhibitor from CM. L[3,4,5-$^3$H] leucine labeled CM from cloned BAEs was incubated with Protein A-Sepharose beads containing antiserum to purified inhibitor as described in detail hereinafter. The immobilized complexes were extracted from the beads by incubation for 1 hour at 37° C. with 0.25M Tris, 2.2 percent SDS, 2.5 percent (v/v) 2-mercaptoethanol, and 20 percent glycerol (pH 6.5). The extracts were fractionated by SDS-PAGE on slab gels and examined by autoradiography. Lane 1 shows starting material. (CM); lane 2 shows immunosupernatant; lane 3 shows immunoprecipitate. The arrow indicates the position of inhibitor activity as revealed by reverse fibrin autography.

Immunoprecipitation screenings were performed both to confirm the above results and to quantitate inhibitor synthesis by cloned BAEs. The results are shown in FIG. 9 and in Table I below.

TABLE I

Inhibitor Synthesis by BAEs

| Cell Isolated[b] | CPM Recovered[a] | | | |
|---|---|---|---|---|
| | CM | Pool II | Gel Extract | Immunoprecipitate |
| BAE$_{26}$ | 9.3 × 10$^6$ (100%) | 2.9 × 10$^6$ (30%) | 1.2 × 10$^6$ (12%) | — |
| Clone A | 3.2 × 10$^7$ (100%) | — | — | 8.2 × 10$^5$ (2.5%) |
| Clone B | 4.5 × 10$^7$ (100%) | — | — | 1.5 × 10$^6$ (3.4%) |

[a]The total, TCA-precipitate radioactivity in the various fractions and in the immunoprecipitates was determined by standard procedures well known in the art. The data are normalized to the percent (shown in the parenthesis) of the cpm in the starting material (CM) recovered at each step.
[b]In each case, approximately 1.5 × 10$^7$ cells were labeled with L[3,4,5-$^3$H] leucine (20 Ci/ml) for 24 hours as described in Section III hereinafter. The serum-free CM (15 ml) was collected and fractionated as indicated.

In these immunological screenings, radiolabeled CM collected from cloned BAEs was incubated (maintained under biological assay conditions) with admixed antibody to the purified inhibitor. The bound material was extracted from the antibody protein A-Sepharose beads, fractionated by SDS-PAGE, and analyzed by autoradiography (FIG. 9). A single radiolabeled polypeptide of an approximate $M_r$ of 50,000 daltons was revealed, and it had inhibitor activity when analyzed by reverse fibrin autography. This protein did not adsorb to protein A-Sepharose beads prepared with preimmune serum. The total radioactivity recovered from the various CMs analyzed in these immunoprecipitation screenings, and the recovery of radiolabeled protein at each step of the purification (FIGS. 7–8; Table I), indicates that the inhibitor accounts for between 2.5–12 percent of the total protein synthesized and secreted by the cells in a 24 hour period (Table I).

D. Development and Evaluation of a Functional Assay for Inhibitor (Inhibitor Binding Assay)

Figure 10:
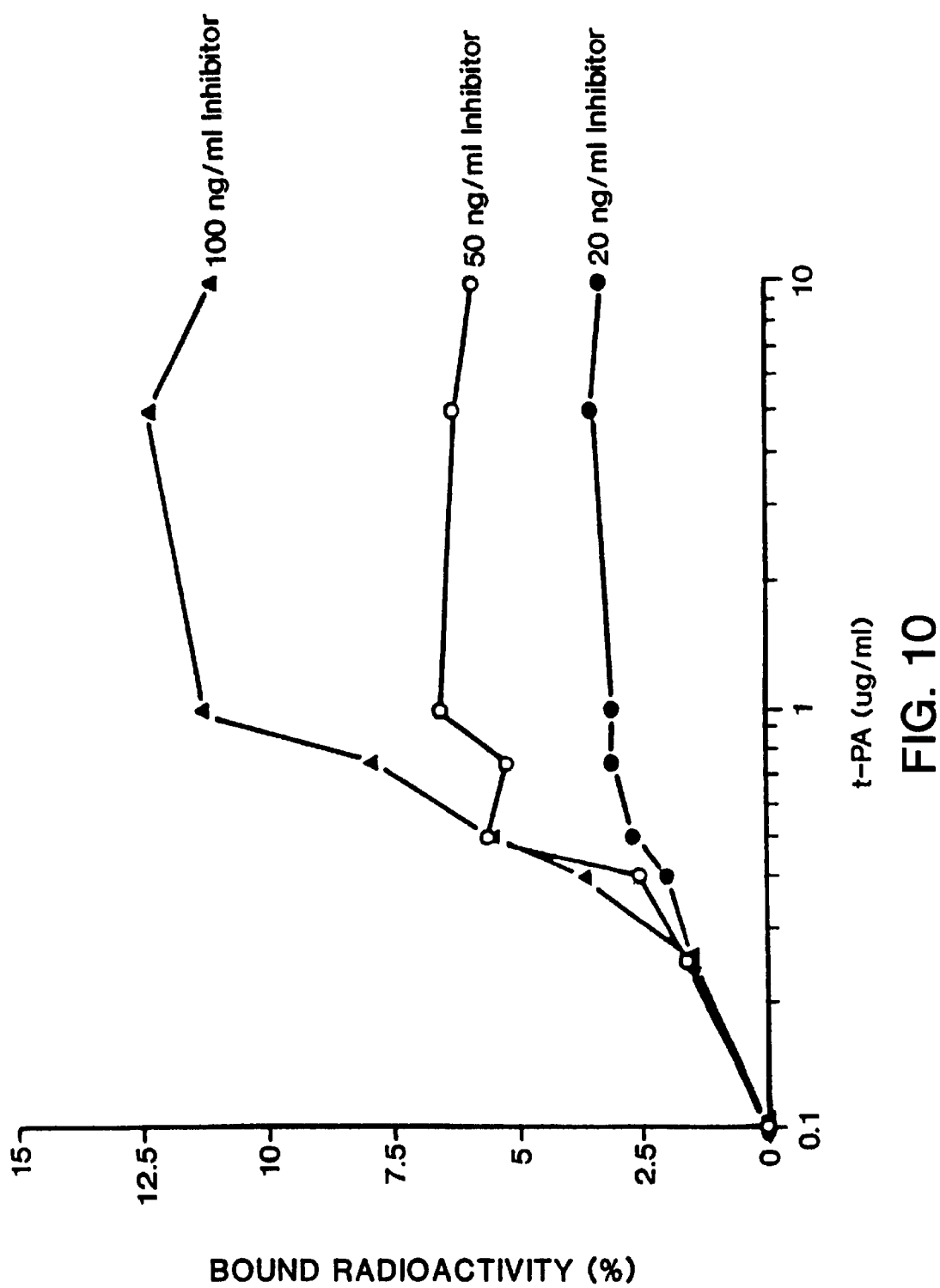
FIG. 10 is a graph illustrating the binding of purified inhibitor to microtiter wells coated with varying concentrations of t-PA. Polyvinyl chloride (PVC) plastic wells were incubated for about 18 hours at 4° C. with t-PA in phosphate-buffered saline (PBS) (50 microliters/well) at the indicated concentrations in units of micrograms/milliliter (ug/ml). The wells were washed, blocked with bovine serum albumin (BSA), and incubated for 2 hours with purified inhibitor in dilution buffer: 20 nanograms (ng)/ml, ●--●50 ng/ml, O-----O; 100 ng/ml, Δ------Δ. After washing the wells, the bound inhibitor was detected by incubation for 2 hours at 37° C. with rabbit anti-inhibitor receptor (1:100 dilution), followed by a 2 hour incubation at 37° C. with $^{125}$I-goat anti-rabbit IgG (1.5×10$^5$ cpm/well). The bound radioactivity in each of the individual wells was determined in a gamma counter and is shown as a percentage of that offered for binding.

Polyvinyl chloride (PVC) plastic wells were coated overnight at 4° C. with varying concentrations of t-PA to affix the t-PA to the polyvinyl chloride solid matrix, and to determine the optimal concentrations of t-PA for the assay of the present invention as shown in FIG. 10. The wells were washed, blocked with BSA to remove non-specific protein binding sites, and maintained (incubated) for 2 hours at 37° C. with three different concentrations of purified inhibitor (20, 50 and 100 ng/ml) to form complexes. After washing, the extent of binding was quantified by incubating (maintaining under biological assay conditions) the complexes so formed first with admixed rabbit anti-inhibitor receptor (diluted 1:100) followed by admixed $^{125}$I-goat anti-rabbit IgG (1.5×10$^5$ cpm/well). As the t-PA concentration used to coat the PVC wells was increased from 0.1 to 1.0 microgram/ml, the detection of bound inhibitor increased at all three concentrations (FIG. 10). Increasing the t-PA coating concentration above 1 microgram/ml did not increase the detection of bound inhibitor. Thus, subsequent screenings employed a t-PA concentration of 1 microgram/ml for coating the PVC wells to affix the t-PA thereto.

Figure 11:
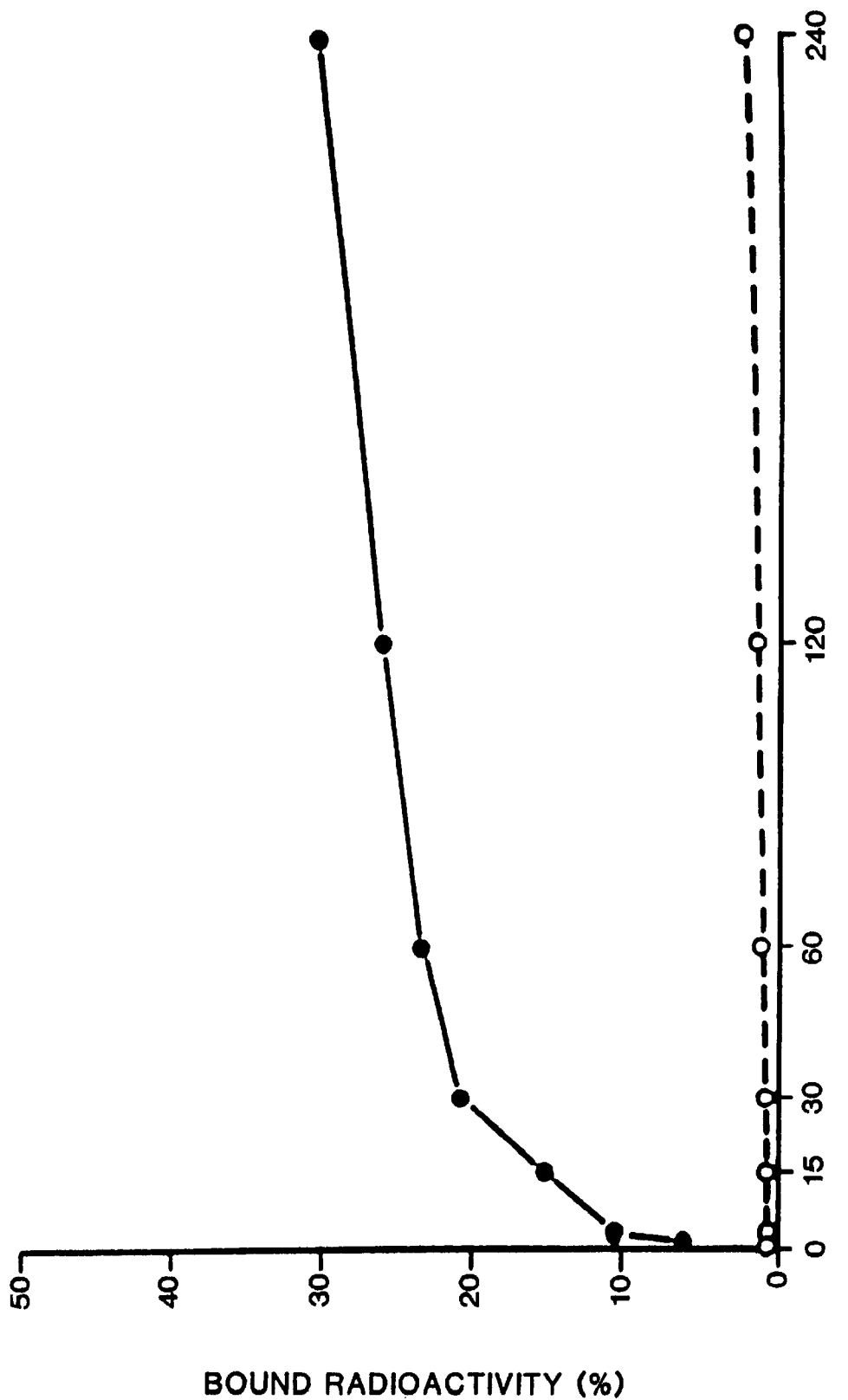
FIG. 11 is a graph illustrating the kinetics of inhibitor binding to t-PA coated wells. PVC plastic wells were incubated overnight at 4° C. with 50 microliters of either t-PA (1 ng/ml in PBS, ●---●or BSA (1 ng/ml in PBS, O-----O). The wells were washed, blocked with BSA, and incubated at 37° C. for the indicated times with purified inhibitor (100 ng/ml) in dilution buffer. After washing the wells, the bound inhibitor was detected as indicated for FIG. 10.

The kinetics of the interaction of the inhibitor with immobilized t-PA were determined in order to optimize the maintenance (incubation) period for inhibitor-containing solutions. Purified inhibitor (100 ng/ml) was incubated at 37° C. for various times on either t-PA or BSA coated wells. The bound inhibitor was then quantified with the rabbit anti-inhibitor receptor (1:100) followed by $^{125}$I-goat anti-rabbit IgG ($1.5 \times 10^5$ cpm/well). The reaction between the inhibitor and immobilized t-PA was a fast reaction with over 75 percent binding occurring within 30 minutes (FIG. 11). During this period, the inhibitor did not bind to control, BSA coated wells. For convenience, a 1 hour incubation time for inhibitor-containing solutions was used in subsequent screenings.

Figure 12:
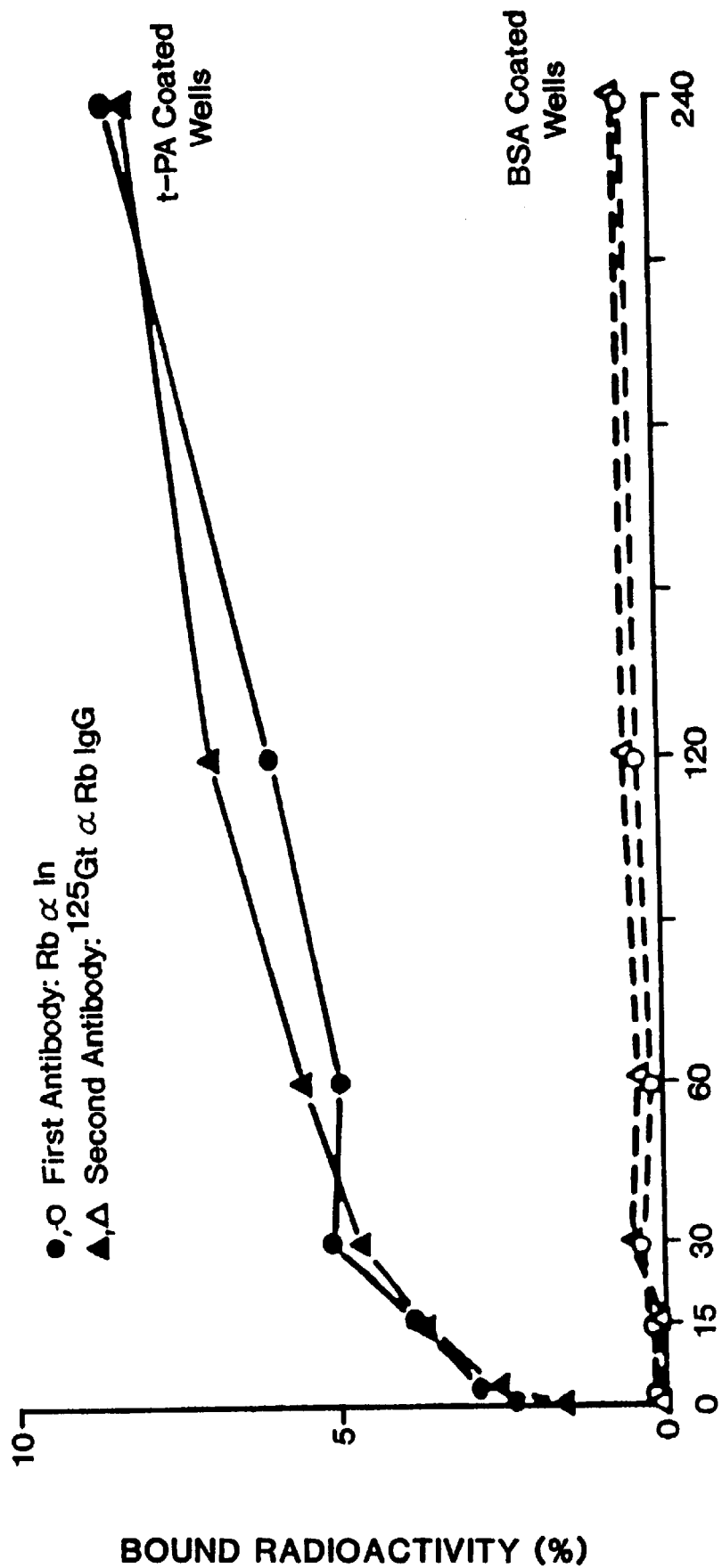
FIG. 12 is a graph illustrating the effect of incubation time of either first or second antibody on the detection of purified inhibitor PVC plastic wells were coated with t-PA (closed figures) or BSA (open figures), washed, blocked and incubated for 1 hour with the purified inhibitor (50 ng/ml) as described for FIG. 10. The wells were incubated with rabbit anti-inhibitor receptor (Rb αIn) (1:100 dilution, O, ● for the indicated times followed by a 2 hour incubation with $^{125}$I-goat anti-rabbit IgG ($^{125}$Gt αRb IgG) (1.5×10$^5$ cpm/well). Alternatively, the wells were incubated for 2 hours with rabbit anti-inhibitor receptor and the incubation time of $^{125}$I-goat anti-rabbit IgG (Δ, ■) was varied.

The maintenance (incubation) time for the polyclonal receptor and indicating means binding times were similarly optimized. t-PA- or BSA-coated wells were incubated for 1 hour at 37° C. with the inhibitor (50 ng/ml) and then incubated with the rabbit anti-inhibitor receptor for various periods of time. Bound receptor was detected by a 2 hour incubation with the indicator ($^{125}$I-goat anti-rabbit IgG). Alternatively, the wells were incubated for 2 hours with the receptor and the incubation time for the indicator was varied. Both the receptor and indicator associated rapidly with their respective antigen in the assay with over 80 percent binding occurring after 1.5–2 hours (FIG. 12). Therefore, subsequent screenings employed a 2 hour incubation period for both the receptor and indicator.

Figure 13:
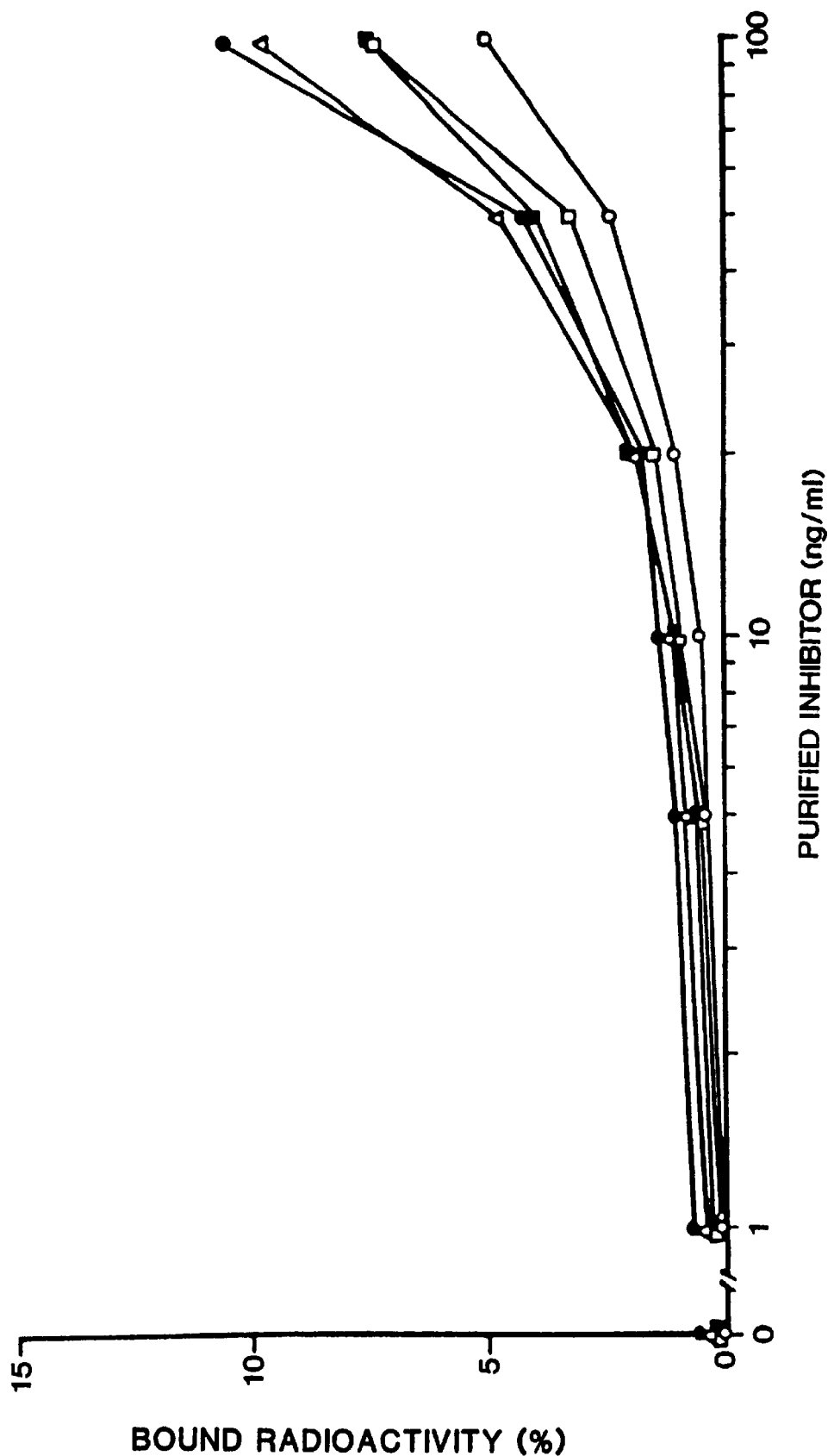
FIG. 13 is a graph illustrating the effect of varying amounts of rabbit anti-inhibitor receptor on the detection of purified inhibitor. PVC plastic wells were coated with t-PA, washed, blocked, and incubated with the inhibitor (50 ng/ml) in the amounts shown as described for FIG. 10. The wells then were incubated for 2 hours at 37° C. with rabbit anti-inhibitor receptor at various dilutions (1:50, ● 1:75, Δ; 1:100, ■; 1:200, ☐; 1:500, O ). The bound antibody-inhibitor-t-PA complex was detected as described for FIG. 10.
Figure 14:
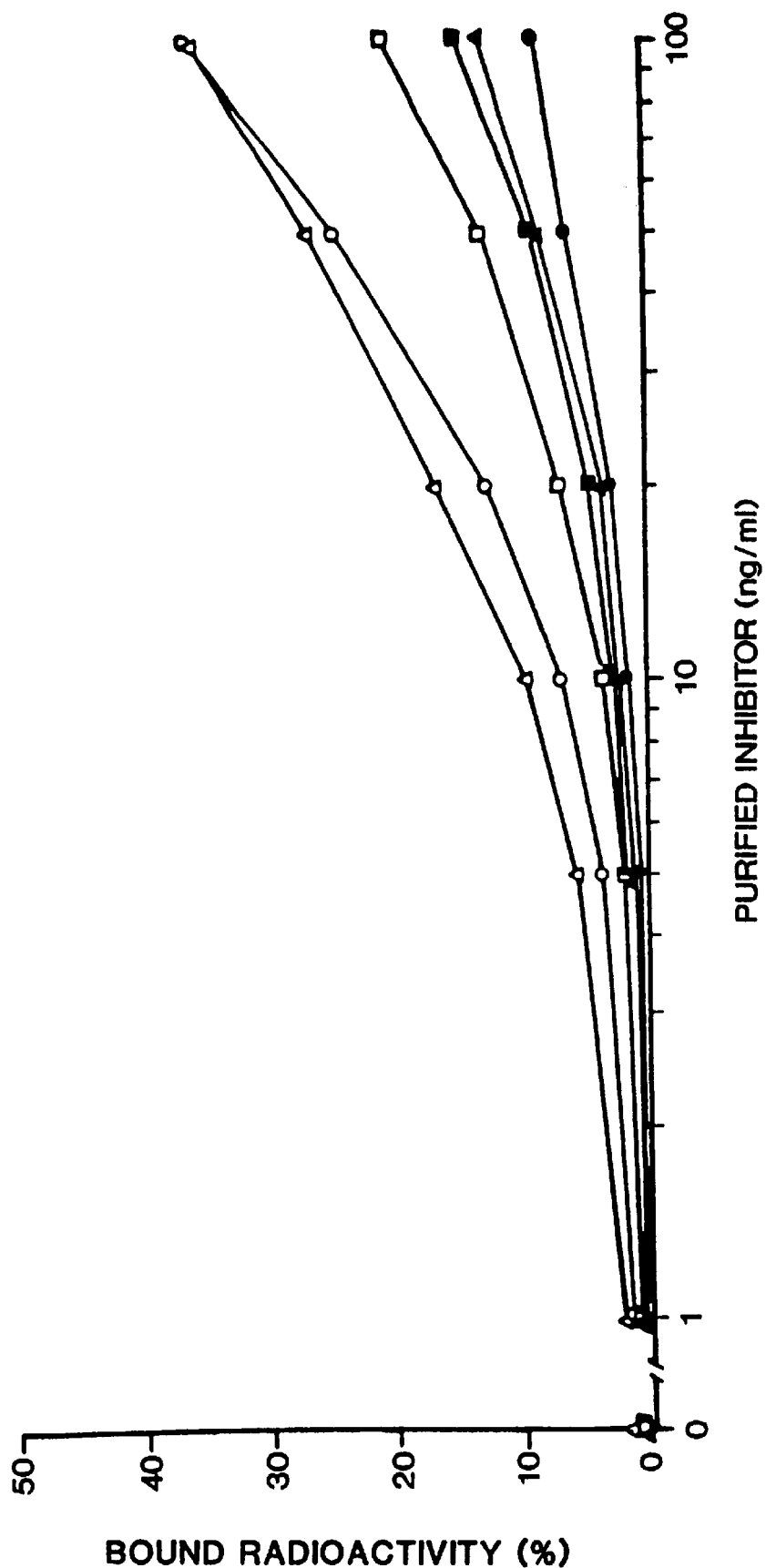
FIG. 14 is a graph illustrating the effect of varying amounts of $^{125}$I-goat anti-rabbit IgG on the detection of purified inhibitor. PVC plastic wells were coated with t-PA, washed, blocked and incubated with the inhibitor (50 ng/ml) as described for FIG. 10. The wells were incubated for 2 hours at 37° C. with the rabbit anti-inhibitor receptor (1:75). After washing, the wells were incubated for 2 hours at 37° C. with 2.5×10$^4$ (Δ), 5×10$^4$ (O), 1×10$^5$ (☐) , 1.5×10$^5$ (■) , 2×10$^5$ (▲), 3×10$^5$ (● cpm of $^{125}$I-goat anti-rabbit IgG.

The effect of varying dilutions of rabbit anti-inhibitor receptor on the detection of inhibitor was determined to optimize the assay's sensitivity. t-PA-coated wells were incubated for 1 hour at 37° C. with various concentrations of inhibitor (1–100 ng/ml). After washing, the wells were incubated with various dilutions of rabbit anti-inhibitor receptor (1;50–1:500) and the bound antibody was detected with $^{125}$I-goat anti-rabbit IgG (a$1.5 \times 10^5$ cpm/ml). Optimal detection of inhibitor occurred at a 1:50–1.75 dilution of the antisera (FIG. 13). Subsequent screenings employed a 1:75 dilution of the antisera. The effect of varying-concentrations of $^{125}$I-goat anti-rabbit IgG ($2.5 \times 10^{4-3 \times 10^5}$ cpm/well) was similarly screened to optimize the assays's sensitivity. Optimal detection-of inhibitor occurred at $2.5–5 \times 10^4$ cpm/well of $^{125}$I-goat anti-rabbit IgG (FIG. 14).

Figure 15:
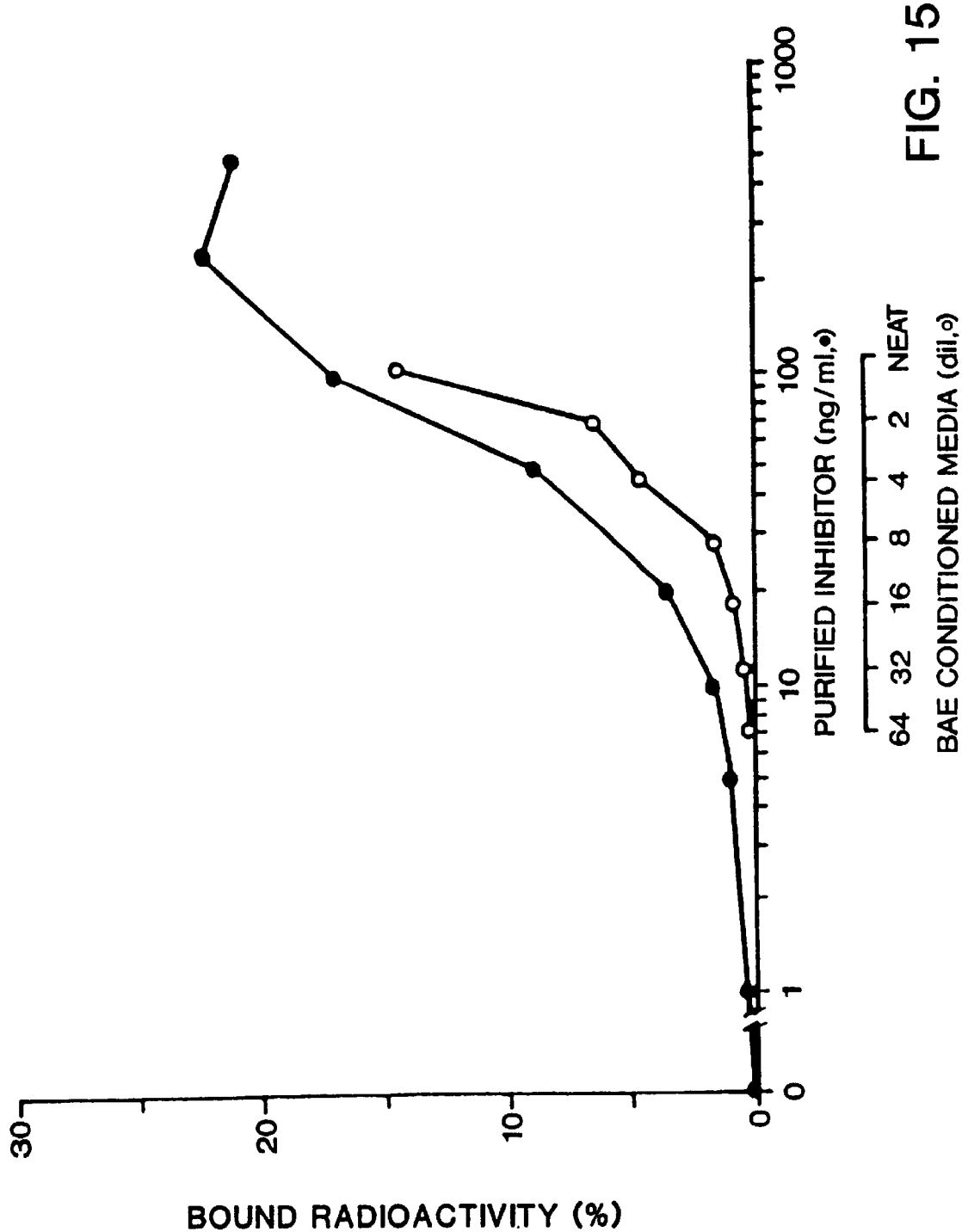
FIG. 15 is a graph illustrating the dose-response curve for the detection of purified inhibitor and inhibitor present in BAE conditioned media, employing the inhibitor binding assay under the particularly preferred conditions established by FIGS. 10–14. t-PA coated wells were incubated for 1 hour at 37° C. with the indicated concentrations of either purified inhibitor (■) or sequential dilutions of bovine aortic endothelial cell (BAE) conditioned media (O). The bound inhibitor was quantified with rabbit anti-inhibitor receptor (1:75) followed by $^{125}$I-goat anti-rabbit IgG (2.5×10$^4$ cpm) as described for FIG. 10.
Figure 16:
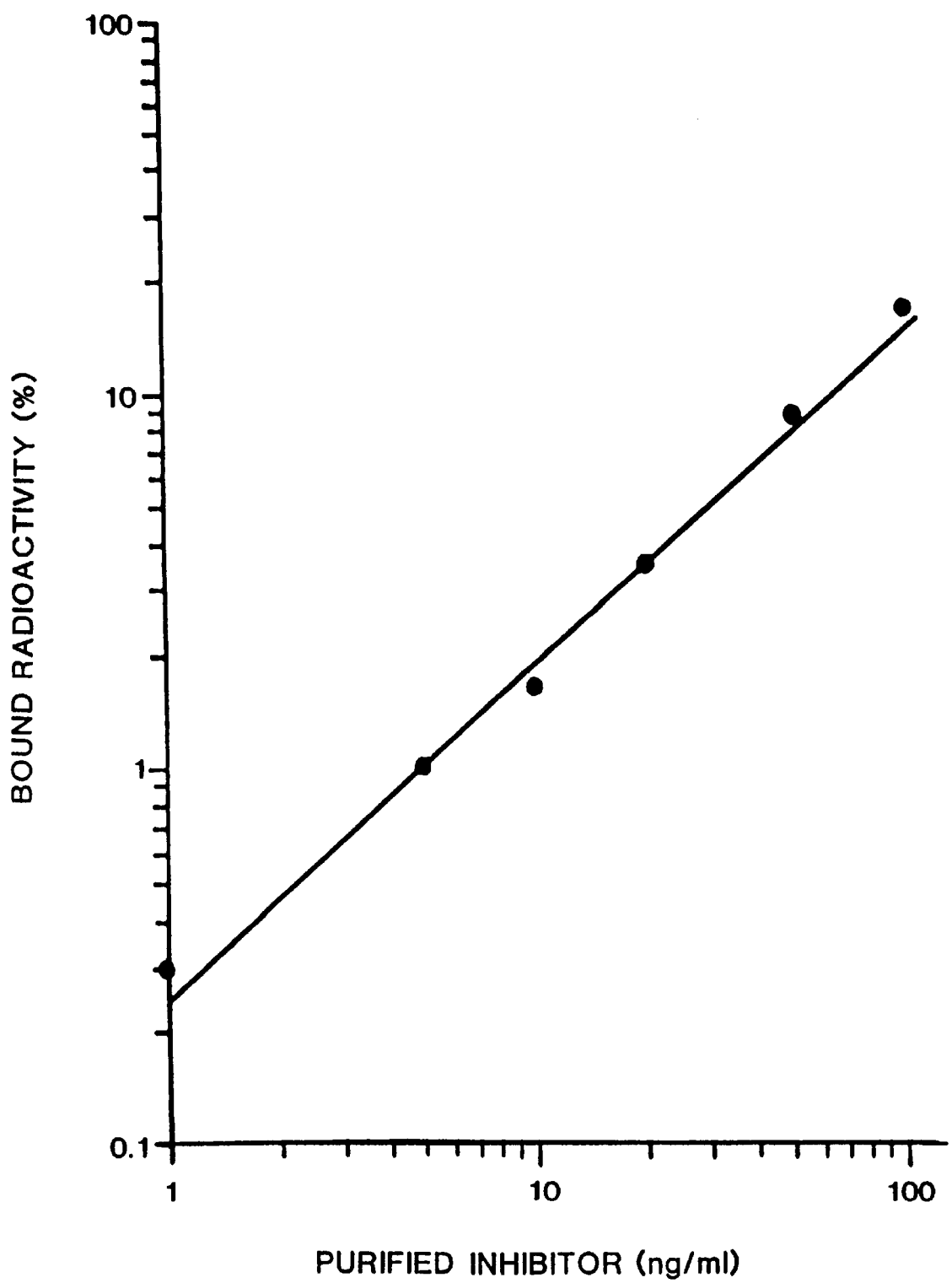
FIG. 16 is a graph illustrating the standard dose-response curve to purified inhibitor of FIG. 15 as represented on a log versus log plot. The binding data for the purified inhibitor shown in FIG. 15 were used.

A typical standard dose-response curve of purified inhibitor as detected in this assay is shown in FIG. 15. The assay was sensitive to 1 ng/ml, demonstrated a linear response to inhibitor between 10 and 100 ng/ml and saturated at inhibitor concentrations above 250 ng/ml. A dose-response using bovine aortic endothelial cell conditioned media (CM) is also shown in FIG. 15. Comparison of this curve with the standard curve indicates that this CM sample contained approximately 100 ng/ml of functionally active inhibitor. For convenience, the standard curve was routinely plotted on a log vs. log plot for the purpose of calculating inhibitor concentrations in unknown samples (FIG. 16). It can be seen that plotting in this way gave a straight line.

E. Comparison of the Inhibitor Binding Assay to Reverse Fibrin Autography

Figure 17:
FIG. 17 is a copy of an autogram showing the dose-response curve of inhibitor as detected by reverse fibrin autography. Various concentrations of purified inhibitor were analyzed by SDS-PAGE and reverse fibrin autography as described in detail hereinafter. Lane 1, 0.5 ng; lane 2, 1 ng; lane 3, 2.5 ng; lane 4, 5 ng; lane 5, 10 ng. Molecular weight markers are indicated.

The sensitivity of the functional assay (inhibitor binding assay) of the present invention was compared with the sensitivity of another assay, reverse fibrin autography, commonly used for the detection and quantitation of PA inhibitor. Various concentrations of inhibitor (0.5 ng–10 ng/lane) were fractionated by SDS-PAGE and then analyzed by reverse fibrin autography. The results are shown in FIG. 17. In this technique, the washed polyacrylamide gel was layed on an indicator gel containing fibrin, plasminogen and a PA. Plasmin was slowly formed, resulting in the general lysis of the gel except in areas where inhibitors were present in the corresponding polyacrylamide gel. The sensitivity of reverse fibrin autography was 2.5 ng/lane (FIG. 17) and since 0.1 ml was applied to each lane, its sensitivity was 25 ng/ml, or 25 times less sensitive than the inhibitor binding assay.

F. Applications of the Inhibitor Binding Assay

Figure 18:
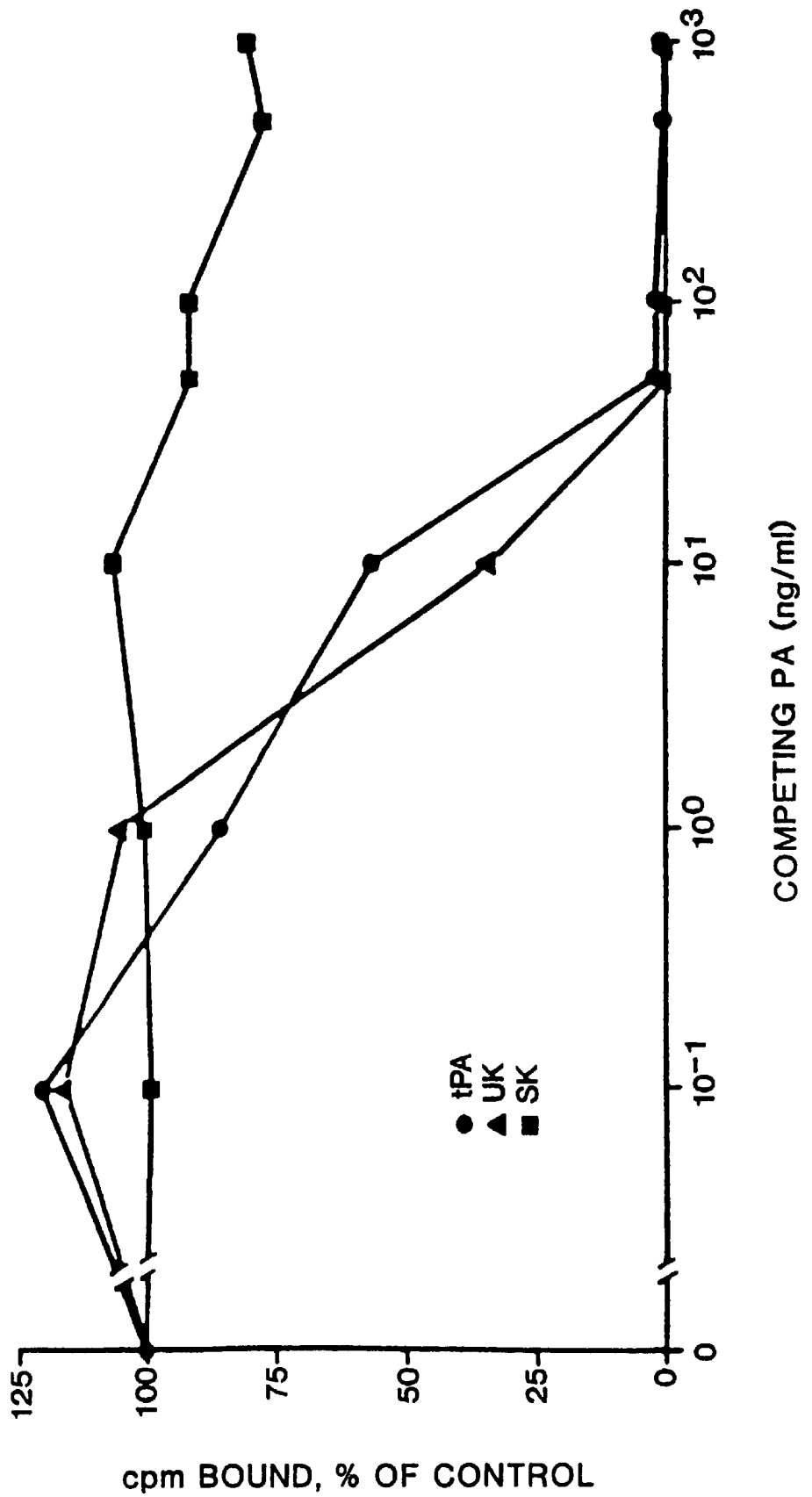
FIG. 18 is a graph illustrating the effect of exogenous PA on the binding of inhibitor to immobilized t-PA. Purified inhibitor (50 ng/ml) was incubated for 1 hour at 37° C. with the indicated concentrations of t-PA (●, u-PA (UK, ▲) or streptokinase (SK, ■). The binding of inhibitor to t-PA was quantified in the inhibitor binding assay described in detail hereinafter.

The inhibitor binding assay of the present invention was used to study the interaction of purified enzymes with the inhibitor. Three purified PAs (t-PA, u-PA and streptokinase) were preincubated for 1 hour at 37° C. with the purified inhibitor (50 ng/ml) and the ability of the inhibitor to subsequently bind to t-PA was quantitated in the inhibitor binding assay. Exogenously added t-PA and u-PA were found to compete with the immobilized t-PA for binding to the inhibitor, with a 50 percent reduction in binding obtained at 12 ng/ml of t-PA and 6 ng/ml of u-PA, as shown in FIG. 18. Neither streptokinase, nor DFP-inactivated t-PA (data not shown) affected the binding of the inhibitor to immobilized t-PA.

Figure 19:
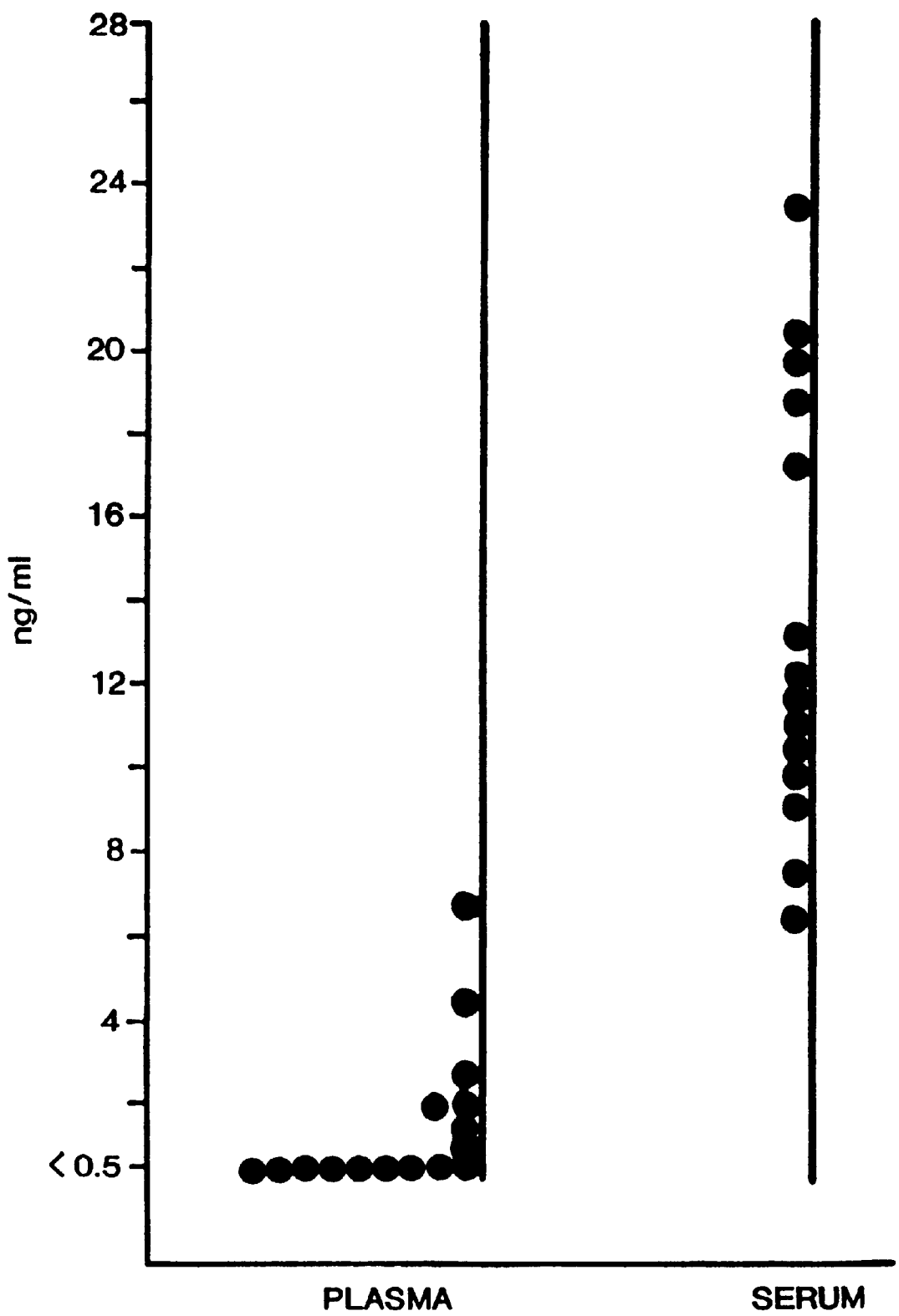
FIG. 19 is a graph illustrating the inhibitor activity in ng/ml of normal human plasma and serum. Blood samples collected by venipuncture from healthy donors were placed into acid-citrated dextrose (ACD). Plasma and serum were prepared from each blood sample, and the inhibitor activity was measured in the inhibitor binding assay described in detail hereinafter.

The inhibitor binding assay of the invention was also used to detect inhibitor in human plasma and serum. Plasma aid serum were prepared from blood collected from 16 healthy human donors and the inhibitor activity in each sample measured in the inhibitor binding assay. Normal human plasma contained low or undetectable levels of inhibitor, as shown in FIG. 19. In contrast, serum from these donors contained high levels of inhibitor activity, as also shown in FIG. 19.

Finally, the assay was employed to determine and compare inhibitor levels in plasma from normal donors and donors with suspected abnormalities in their hemostatic system. The results are shown below in Table II.

TABLE II

Detection of Inhibitor in Normal and Patient Plasma

| Sample | Dilution | cpm Bound | Inhibitor (ng/ml) |
|---|---|---|---|
| Normal plasma | 1:5 | 1500 | N.D.[1] |
|  | 1:10 | 700 | N.D. |
| Patient Plasma | 1:5 | 4700 | 25 |
|  | 1:10 | 2300 | 25 |

[1]"N.D." indicates no inhibitor detected (less than 2 ng/ml).

These samples were kindly provided by Dr. B. Wiman. It can be seen from this screening that no inhibitor was detected in normal plasma, while the patient plasma had approximately 25 ng/ml. This same patient was shown to have elevated inhibitor when studied with a different assay in Wiman, *Thrombosis Research,* 31, 427 (1983).

G. Identification of endothelial cell type beta-PAI activity in placenta

Two inhibitor zones having an $M_r$ of about 50–55 kilodaltons (kda) were revealed when 20 microliters (ul) of a crude human placental extract were analyzed for PAI activity by SDS-PAGE [Laemmli, (1970) *Nature* (London), 227, 680–685] and reverse fibrin autography (RFA) [Erickson et al., (1984) *Analytical Biochemistry* 137, 454–463]. Immunoprecipitation studies demonstrated that the two inhibitor zones resulted from the presence of both the placental-type PAI [Astedt et al., (1985) *Thromb. Haemostasis.* 53, 122–125] and the endothelial cell-type PAI [Loskutoff et al., (1983) *Proc. Nat. Acad. Sci. U.S.A.,* 80:2956–2960; Emeis et al., (1983) *Biochem. Biophys. Res. Commun.* 110:392–398;

Thorsen et al. (1984) *Biochim. Biophys. Acta* 802, 111–118; van Mourik et al., (1984) *J. Biol. Chem.* 259, 14914–14921]. Quantitation using a radioimmune assay [Schleef et al. (1985) *J. Lab. Clin. Med.* 106, 408–415] indicated that the extract contained 270 nanograms per milliliter (ng/ml) of endothelial (beta-) PAI.

Since the placental tissue had been extensively washed prior to extraction, this beta-PAI was most likely synthesized by cells contained in placenta and not a serum contaminant. Placenta was therefore employed as a source for the isolation of a cDNA for beta-PAI.

H. Isolation of Human Beta-PAI cDNA

Approximately $7 \times 10^5$ recombinant phages from a $\lambda gt_{11}$ expression library containing cDNA inserts prepared from human placental mRNA were obtained from Dr. Jose Millan of Cancer Research Center, La Jolla Cancer Research Foundation, La Jolla, Calif. That expression library is disclosed in Millan, (1986) *J. Biol. Chem.* 261, 3112–3115 whose disclosures are incorporated herein by reference, as containing $1 \times 10^6$ independent recombinant phages.

Cytoplasmic-extracts from the phage-infected *E. coli* were screened immunologically to identify those phages containing cloned cDNAs that expressed the beta-PAI or a fusion polypeptide including that PAI fused at its amino-terminus to a portion of the beta-galactosidase molecule encoded by the $\lambda gt_{11}$ vector. Thirty-four positive clones were obtained, half of which continued to be positive through a second screening. Three positive clones were randomly selected and plaque purified, and phage DNA was prepared.

The phage DNA from the three clones denominated $\lambda 1.2$, $\lambda 3$ and $\lambda 9.2$ was digested with EcoRI and the cDNA inserts were determined to be 1.9, 3.0 and 1.9 kilobase pairs (kb) in length, respectively. The EcoRI 3.0 kb cDNA insert from $\lambda 3$ was subcloned into a pBR322-derived plasmid vector, pGEM-3, to form the recombinant plasmid pPAI$_3$ using *E. coli* MC1061 as a unicellular replication/expression medium as described by Bolivar et al., (1977) *Gene* 2, 95–113. The subcloned cDNA insert was excised with EcoRI, and purified using an agarose gel. The cDNA insert was nick-translated and shown to hybridize with $\lambda$ 1.2 and $\lambda$ 9.2 DNAs at high stringency, indicating that the DNA inserts in the three clones were related.

Three lines of evidence support the conclusion that the three isolated clones code for a proteinaceous material that is or includes the human endothelial cell type, (beta-migrating) PAI.

Figure 20:
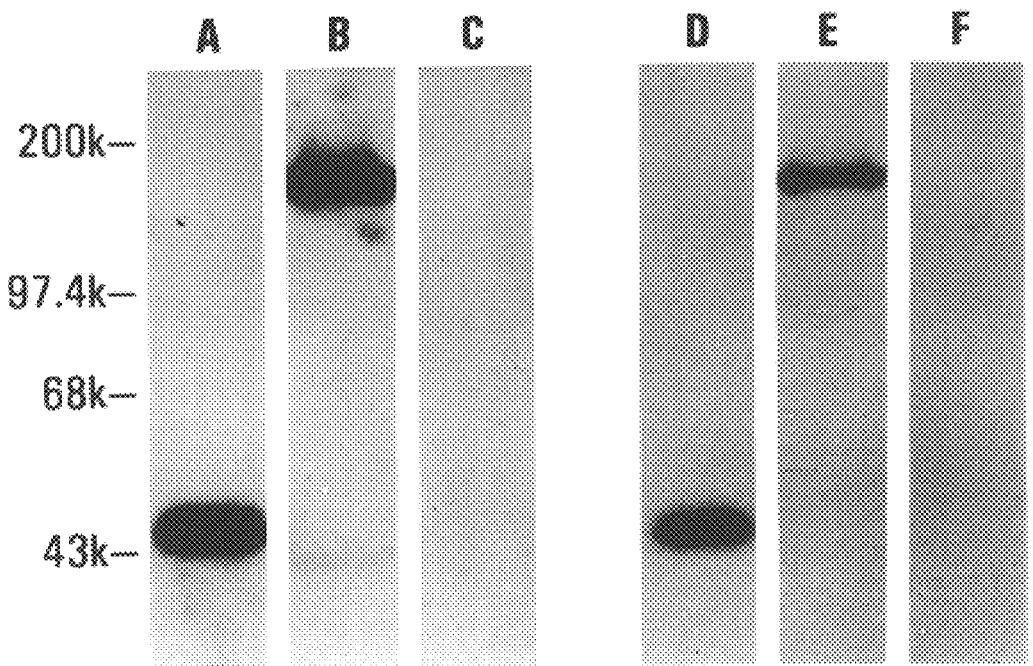
FIG. 20 is a photograph of a Western blot analysis of E. coli crude extracts. Extracts prepared from induced lysogenic E. coli strains were fractionated by SDS-PAGE and analyzed by Western blotting as described hereinafter. Lanes A, D and F contain 300 nanograms (ng) of purified bovine aortic endothelial cell (BAE) beta-PAI. Lanes B and E contain 50 microliters (ul) of extract from E. coli strain Y1089 lysogenized with λ 9.2, a recombinant lambda (λ) phage with the human endothelial cell type PAI cDNA sequence inserted. Lane C contains 50 ul of extract from strain Y1089 lysogenized with the vector λ gt$_{11}$ lacking the insert. For the Western blotting experiments shown in lanes A–C, affinity-purified IgG against the BAE beta-PAI was used as primary antibody. For Western blotting of lanes D–F, the antiserum used was affinity-purified on various proteins bound to nitrocellulose paper. For lane D, antiserum affinity-purified on the fusion polypeptide from λ9.2 was used; lane E, antiserum affinity purified on the BAE beta-PAI; and lane F, antiserum affinity purified on proteins M$_r$ 150–200 kilo-dalton (kda) from the λgt$_{11}$ lysogen. The autoradiograms were exposed for 16 hours.

(i) Induction of an *E. coli* lysogenic strain prepared by infecting a high frequency of lysogeny strain (Y1089; ATCC 37196) with $\lambda 9.2$ resulted in the expression of a recombinant fusion polypeptide having an apparent relative mass of about 180,000 daltons ($M_r$=180 kda) that was recognized by an affinity-purified IgG from antisera raised against the purified BAE beta-PAI (FIG. 20, lane B). An *E. coli* strain lysogenic for $\lambda gt_{11}$, and thus lacking the cDNA insert, did not produce such an immunoreactive protein (FIG. 20, lane C).

(ii) The 180 kda recombinant fusion polypeptide and the BAE beta-PAI share antigenic epitopes, since affinity purification of the antiserum to BAE beta-PAI on the recombinant fusion polypeptide yielded antibodies that recognized the purified BAE beta-PAI in Western blots (FIG. 20, lane D).

Figure 21:
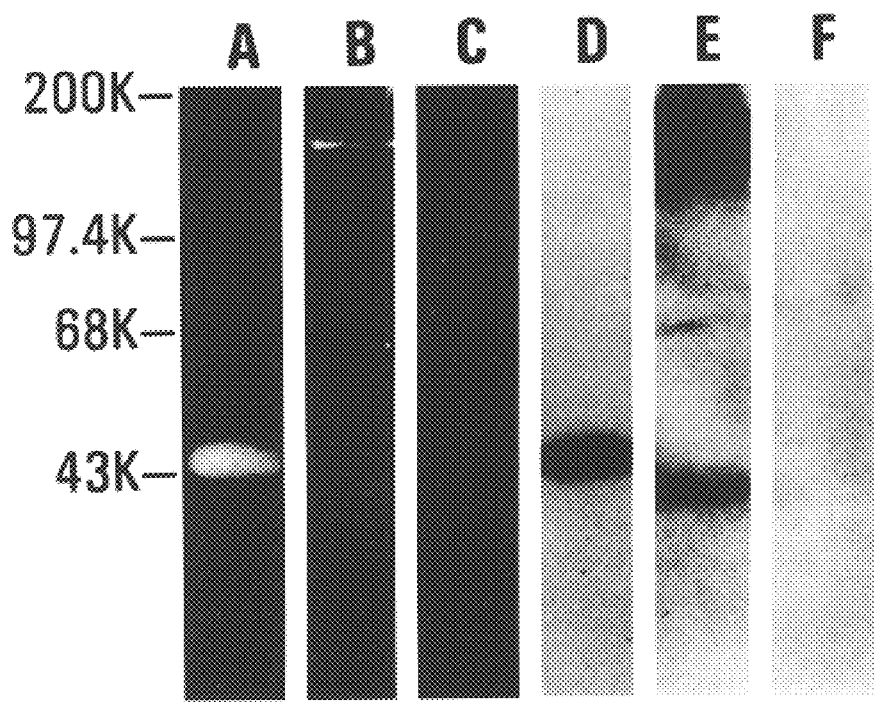
FIG. 21 is a photograph showing the analysis of inhibitor activity in extracts from induced E. coli lysogens. Extracts from lysogenic E. coli strains were fractionated by SDS-PAGE and then analyzed by reverse fibrin autography (RFA) using u-PA (lanes A–C) and Western blotting followed by autoradiography (lanes D–F). Lanes A and D contain 300 ng of purified bovine beta-PAI. Lanes B and E contain 50 ul of extract from the strain lysogenic for λ9.2. Lanes C and F contain 50 ul of extract from the strain lysogenic for λgt$_{11}$. The autoradiogram for lane D was exposed for 16 hours, while those for lanes E and F were exposed for 2 weeks.

(iii) Analysis of *E. coli* extracts by SDS-PAGE followed by RFA revealed that the A9.2 lysogen containing the 1.9 kb insert, but not the $\lambda gt_{11}$ lysogen, expresses PAI activity (FIG. 21, lane B).

Surprisingly, two recombinant proteinaceous PAIs with $M_r$s of 180 kda and 40 kda, respectively, were present in the $\lambda 9.2$ extracts. To investigate the relationship of these PAIs, proteins from the lysogens were fractionated by SDS-PAGE, and were again analyzed by Western blotting but this time the autoradiograms were developed after a longer exposure (FIG. 21, lanes E and F). Two polypeptides were detected, and these co-migrated with the inhibitor activities (compare lanes B and E). The great majority of the beta-PAI antigen produced by the A9.2 lysogen was detected at an $M_r$ of approximately 180 kda; however, a small amount of antigen was also detected at $M_r$ 40 kda (FIG. 21, lane E). Since the two PAIs share immunologic and biological properties the smaller is most likely derived from the larger through proteolytic processing of the beta-galactosidase-PAI fusion polypeptide. The specific activity of the released 40 kda protein may be higher than that of the larger fusion protein because it is no longer sterically hindered by a fused polypeptide fragment. However, even though of lower specificity activity, possibly caused by steric hinderance, the 180 kda fusion polypeptide did exhibit plasminogen activator inhibitory activity and was shown to be immunologically related (similar) to BAE PAI.

The observed biological activity (binding to and inhibiting of) t-PA activity was surprising inasmuch as the replication/expression medium was a procaryotic cell and the proteinaceous molecule is native to mammals. In addition, the native molecule is glycosylated while the expressed fusion polypepide and smaller 40 Kda protein were substantially free of glycosylation. Thus, although the expressed proteinaceous molecules could be expected to be folded differently from the native molecule and were free of glycosylation while the native moleacule is glycosylated, the expressed proteinaceous molecules exhibited the biologic activity of the native, mammalian protein.

Recombinant plasmid pPAI$_3$ contained in host *E. coli* strain MC1061 was deposited at the American Type Culture Collection 12301 Parklawn Drive, Rockville, Md.20852. It was received on Aug. 19, 1986, and was given the designation ATCC 67188.

The present deposit was made in compliance with the Budapest Treaty requirements that the duration of the deposit should be for 30 years from the date of deposit for 5 years after the last request for the deposit at the depository or for the enforceable life of a U.S. patent that matures from this application, whichever is longer. The recombinant plasmid-containing cells will be replenished should they become non-viable at the depository.

I. Nucleotide Sequence of DNA Coding for Human Beta-PAI and Assignment of Protein Sequence The DNA sequence from both strands of the 3.0 kb cDNA insert of clone $\lambda$ 3 was established by sequencing deletion subclones constructed by the method of Dale et al. (1985) *Plasmid* 13, 31–40. FIG. 22 shows the DNA sequence along with the inferred amino acid residue sequence. This is not a full-length cDNA since the untranslated region, the initiation codon, and most of the signal peptide are missing from the 5'-terminus end of the molecule.

In order to identify the codon coding for the amino-terminus of the mature protein, the deduced amino acid residue sequence was aligned with that of partially sequenced bovine beta-PAI and partially sequenced human endothelial PAI isolated by other means in our laboratory. The amino-terminal residue of mature human endothelial cell type PAI was determined to be valine (Val; V). Based on that alignment the valine designated number 1 in FIG. 22 is the amino-terminal residue of the human endothelial (beta-) PAI.

Two originally obtained clones contained different codons at the −4 amino acid residue position. One of those codons codes for a serine (Ser; S) residue (λ3) while the other (λ9.2) codes for a glutamic acid residue (Glu; E). Glutamic acid has been found to be the correct residue at that position and is so shown in FIG. 22.

The naturally occurring human beta-PAI is secreted and is therefore likely to contain a signal peptide [Blobel et al., (1975) *J. Cell Biol.* 67, 852–862]. The signal peptidase normally cleaves to the carboxyl side of residues with small neutral side chains such as glycine, alanine and serine [von Heijne, (1984) *J. Mol. Biol.* 173, 243–251]. Thus, the alanine (ala) at the amino-terminal side of the valine (val) designated number 1 may represent the terminal residue of the signal peptide.

The reading frame shown in FIG. 22 is the only one without multiple termination codons, and codes for 383 residues followed by a TGA stop codon. Removal of the putative signal peptide by cleavage between alanine at position −1 and the valine designated as number 1 results in a mature beta-PAI that is 379 residues long and has a calculated molecular weight for the carbohydrate-free molecule of 42,770 daltons. This calculation agrees well with the molecular weight of the unglycosylated form of the BAE beta-PAI as determined by in vitro translation of its mRNA [Sawdey et al. (1986) *Thromb. Res.* 41, 151–160]. Human beta-PAI is glycosylated [van Mourik et al., (1984) *J. Biol. Chem.* 259, 14914–14921] and the amino acid residue sequence in FIG. 22 contains 3 putative glycosylation sites conforming to the canonical asn-x-ser/thr sequence [Marshall (1974) Biochem. Soc. Symp. 40, 17–26] at positions 209–211, 265–267, and 329–331.

The 3'-untranslated region of the 3.0 kb cDNA is 1788 base pairs (bp), excluding the poly (A) tract. The consensus polyadenylation sequence AATAAA is found sixteen bp upstream from the poly (A) attachment site, which is in agreement with previous reports that this sequence is generally located 15–25 nucleotides upstream from the polyadenylation site [Proudfoot, (1976) *Nature (London)* 263, 211–214].

The two clones carrying cDNA inserts of 1.9 kb were partially sequenced and appear to be identical. These clones are also identical to the 3.0 kb cDNA except that they are truncated and lack much of the 3'-untranslated region (i.e., they lack the region 3' from nucleotide 1960).

Figure 23:
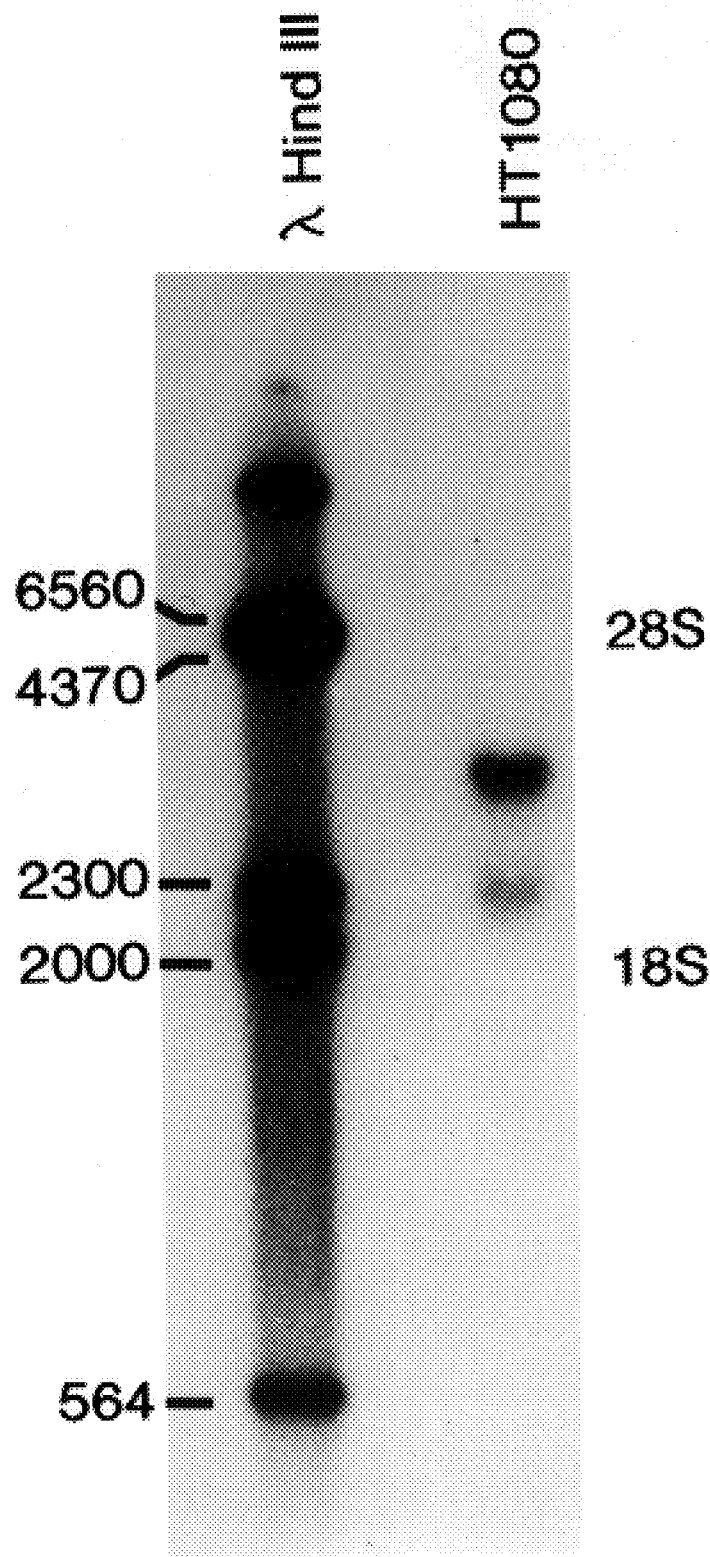
FIG. 23 is a photograph of an autoradiograph that illustrates detection of beta-PAI mRNA. Total RNA from the fibrosarcoma cell line HT 1080 was isolated, subjected to agarose gel electrophoresis in the presence of formaldehyde, and after blotting to nitrocellulose, was hybridized to $^{32}$P-labeled λ 3 cDNA. As markers on the left side, Hind III-digested λ DNA was used. The relative mobilities of the eukaryotic 28S and 18S ribosomal RNA are indicated.

Northern blot analysis of total RNA prepared from the human fibrosarcoma cell line HT 1080 (ATCC CCL 121), using the 3.0 kb cDNA as probe, indicated the presence of two distinct transcripts, 3.0 and 2.2 kilobases in length (FIG. 23). This observation suggests that the 1.9 kb cDNAs may have been copied from the shorter RNA transcript. A similar size heterogeneity at the 3'-termini of mRNAs has been observed in other systems. It may result from expression of more than one gene, from alternative splicing events, or from the use of multiple polyadenylation signals [Crabtree et al., (1982) *Cell* 31, 159–166; King et al., (1983) *Cell* 32, 707–712; Hickok et al., (1986) *Proc. Natl. Acad. Sci. USA.*, 83, 594–598]. The mechanism in this case is not clear.

Although the only polyadenylation consensus signal (AATAAA) found in this cDNA sequence is at the 3'-terminus of the 3.0 kb cDNA (FIG. 22), a similar but slightly modified sequence (AATAAT) was found at nucleotide positions 1998–2003. If this sequence were used as a signal for poly (A) addition it could explain the presence of the shorter transcript. In other systems, polyadenylation has been found to take place in the absence of the AATAAA sequence [Ohkubo et al., (1983) *Proc. Natl. Acad. Sci. USA.*, 80, 2196–2200].

Comparison of the deduced amino acid sequence with other proteins using the Fast Protein Analysis homology program [Lipman et al. (1985) *Science* 227, 1435–1441] revealed that the beta-PAI was 25–30% homologous with antithrombin III (AT III), alpha$_1$-antitrypsin (alpha$_1$AT), alpha$_1$-antichymotrypsinogen and ovalbumin, and therefore is a member of the serine proteinase inhibitor super family of proteins (serpins). The serpins have diverged from an ancestral molecule over a 500 million year period [Carrell et al., (1985) *Trends Biochem. Sci.* 10, 20–24] and now represent a diverse group of related proteins that control the major proteolytic cascades of the body (e.g., the coagulation, complement, fibrinolytic, and inflammatory cascades).

The inhibitory specificity of the serpins appears to be defined primarily by a single amino acid residue in the reactive center, the so-called P$_1$ residue [Carrell et al., (1985) *Trends Biochem. Sci.* 10, 20–24]. In general, this amino acid residue reflects the known specificity of the target proteinase. The reactive center of the serpins is located near the carboxyl-terminus, and because it appears to protrude from the rest of the molecule [Carrell et al. (1985) *Trends Biochem. Sci.* 10, 20–24], may represent the ideal substrate or "bait" for the protease.

Protease inhibition is associated with the formation of 1:1 complexes between inhibitor and enzyme. The amino acid residue sequences of the reactive centers of beta-PAI, alpha$_1$AT and AT III are aligned in FIG. 24, using single letter amino acid residue designations.

In this alignment, the R (arg) residue at position 346 is the P$_1$ residue of the PAI. Plasminogen activators convert plasminogen into plasmin by cleavage of a single arg-val bond [Collen, (1980) *Thromb. Haemostasis* 43, 77–89]. Thus, this alignment is consistent with the known arg-specificity of PAs. The finding that the P$_{17}$ residue is glutamic acid (E) also supports this alignment, since this glutamic acid acts as the 'hinge' in serpins and is conserved in all serpins sequenced to date [Carrell et al., (1985) *Trends Biochem. Sci.* 10, 20–24].

Human beta-PAI is unusually sensitive to oxidants and rapidly loses its activity in the presence of low concentrations of chloramine T. Since there are no cysteines in the deduced protein sequence (FIG. 22), and since the activity of the oxidatively inactivated beta-PAI can be restored by treatment with methionine sulfoxide peptide reductase, the loss of activity appears to reflect the oxidation of a critical methionine. The methionine in the reactive center of beta-PAI (i.e., at position 347, the inferred P$_1$' position) is a likely candidate, since alpha$_1$AT also is sensitive to oxidation and its loss of activity has been related to the oxidation of the P$_1$ methionine [Carrell et al., (1985) *Trends Biochem. Sci.* 10, 20–24]. In both cases, the resulting methionine sulphoxide is a bulkier residue and may not readily fit into the pocket of its substrate proteinase.

It has been suggested that the ability to selectively inactivate alpha$_1$AT by oxidation of its active site methionine is an important and unique regulatory feature of this system. Activated neutrophils may neutralize the inhibitor by the secretion of oxygen free radicals [Carrell et al., (1985) *Trends Biochem. Sci.* 10, 20–24] at inflammatory sites. This additional level of regulation may provide the means by which essential tissue breakdown can take place, even in the presence of inhibitors which normally inhibit neutrophil elastase. Elevated PA activity has been correlated with tissue destruction, tissue remodelling, and with the formation of new organs [for review, Dano et al., (1985) *Adv. Cancer Res.* 44, 139–266]. The ability to oxidatively inactivate the beta-PAI present in these tissues may also be an important regulatory feature of these systems, enabling PAs to function in the presence of their inhibitor. Thus, the local generation of oxidants may inactivate both alpha $_1$AT and beta-PAI, and in the process unleash a cascade of proteolytic enzymes including elastase, plasmin, and collagenase [Moscatelli et al., (1980) in Proteases and Tumor Invasion, ed. P. Struli (Raven Press, New York) pp. 143–152].

III. MATERIALS AND METHODS

A. Assay-Related

1. Plasminogen Activator

Tissue-type plasminogen activator (t-PA) was isolated from human melanoma cell conditioned media as described in Rijken et al., *J. Biol. Chem.,* 256, 7035 (1981). Briefly, human melanoma cells were grown to confluent monolayers in plastic tissue culture flasks (Falcon, Oxnard, Calif.) at 37° C. in atmospheric air supplemented with 6 percent of $CO_2$. The growth medium consisted of 100 ml of modified Eagle's essential medium supplemented with sodium bicarbonate (16 ml of a 7.5 percent solution per liter of medium), L-glutamine (10 ml of a 200 mM solution per liter of medium), and heat-inactivated newborn calf serum (final concentration, 10 percent). The cells were washed with medium without calf serum and incubated with 25 ml of serum-free medium. The-resulting conditioned medium (CM) was harvested and replaced on 3 consecutive days, centrifuged at 7000×g for 30 minutes and stored at −20° C. until use. When indicated, Aprotinin (Calbiochem-Behring, La Jolla, Calif.) was added, both to the serum-containing and to the serum free medium (20 KIU/ml, final concentration).

Commercially available urokinase ($5 \times 10^5$ CTA units of WINKINASE, Sterling-Winthrop, Rensselaer, N.Y.) was purified further by affinity chromatography as described in Holmberg et al., *Biochim. Biophys. Acta,* 445, 215 (1976).

2. Plasminogen Activator Inhibitor

Bovine aortic endothelial cells (BAEs) employed for the purification of the inhibitor were isolated from the aorta of cows by the method of Booyse et al., *Thromb. Diathes. Haemorrh.,* 34, 825 (1975), whose teachings are incorporated herein by reference, and cultured in 150 cm² flasks (Falcon Plastics, Oxnard, Calif.) in 15 ml of modified Eagle's medium supplemented with 10 percent fetal calf serum (Irvine Scientific, Santa Ana, Calif.) as described in Levin et al., *Thromb. Res.,* 15, 869 (1979). The cells for the screenings had been passaged 16–22 times at a 1:5 ratio, and in general had been confluent for at least one week prior to the preparation of conditioned media (CM) as described below.

Cloned BAEs were employed for some of the metabolic labeling screenings. These clones were developed from single cells that grew out of a primary cell preparation. Briefly, freshly isolated cells were seeded into 60 mm dishes and allowed to attach overnight. The cells were washed with pre-warmed medium, released from the culture dish with trypsin (GIBCO, Long Island, N.Y.), dispersed gently with a pipette, and diluted to approximately 20 cells per ml in growth medium. Four to five aliquots (50 microliters each) of the diluted cells were then placed on the inverted sterile underside of Cooper dish lids (Falcon Plastics, Oxnard, Calif.) and incubated for 60 minutes at room temperature to allow cell attachment.

After the position of each of the cellular droplets was marked with a pen, the lids were inverted back onto Cooper dish bottoms containing confluent BAEs in 6.7 ml of growth medium. The confluent BAEs had been maintained in this medium for 24 hours, presumably elaborating growth factors, Gajdusek et al., *J. Cell Biol.,* 85, 467 (1980). The marked areas were examined in the microscope, and those areas containing single cells were monitored on consecutive days for cell growth. When these clones had grown to a few thousand cells, the cells were removed by ring cloning in the presence of trypsin, distributed into 0.5 cm microtiter wells (Falcon) containing 100 microliters of growth medium, and allowed to grow to confluency. Empty lids also were inverted onto Cooper dish bottoms containing confluent BAEs, and served as controls for this method. These lids remained free of cells throughout the incubation period indicating that cells from bottoms did not detach and reattach on the lids. The clones developed by this procedure were positive for Factor VIII-related antigen indicating that they consisted of endothelial cells, Jaffe et al., *J. Clin. Invest.,* 52, 2757 (1973).

Confluent monolayers were then washed twice with 15 ml of PBS and subsequently incubated with 15 ml of serum-free medium. After 24 hours, the resulting CM was collected, pooled, centrifuged for 5 minutes at 400×g and, after adding $NaN_3$ and Tween 80 (Sigma Chemicals, St. Louis, Mo.) to concentrations of 0.02 percent and 0.01 percent respectively, stored at −30° C. until further use. Approximately 1 liter of CM was passed over a 10 ml concanavalin A-Sepharose (Sigma Chemicals, St. Louis, Mo.) column (1.5×5 cm) previously equilibrated with phosphate-buffered saline (PBS) containing 0.02 percent $NaN_3$ and 0.01 percent Tween 80 [polyoxyethylene (80) sorbitan monooleate], at a speed of 10 ml/h at 4° C.

After collecting the flow-through material, the column was washed with at least 10 column volumes of PBS containing 1M NaCl, 0.01 percent Tween 80 and 0.02 percent $NaN_3$ (pH 7.4) to remove non-specifically adsorbed proteins. The column was washed with approximately the same volume of this buffer but without the added NaCl, and then eluted in 2 steps. In the first, protein was eluted with 0.01M sodium phosphate, pH 7.2, containing 0.5M alpha-methyl-D-mannoside (Sigma Chemicals, St. Louis, Mo.), 0.02 percent $NaN_3$ and 0.01 percent Tween-80, at a speed of 2.5 ml/h. The column was eluted a second time with the same buffer but containing 1M NaCl.

The second step in the purification involved preparative SDS-PAGE. The inhibitor-containing fractions (identified by slab gel electrophoresis and reverse fibrin autography) were pooled and aliquots (225 microliters) were subjected to SDS-PAGE in tube gels. When the tracking dye reached the bottom of the gel, the gels were frozen and cut into 1 mm slices. Every two slices were combined and extracted for 24 hours at 4° C. with 0.2 ml of PBS containing 0.01 percent Tween. Each extract was then tested for inhibitor activity by the $^{125}$I-fibrin plate assay (described below). The fractions containing the peak of inhibitor activity were pooled and stored at −70° C. until further use.

The inhibitor also was purified from CM collected from cells cultured in the presence of L-[3,4,5-$^3$H] leucine. In this case, the cultures were washed twice with 15 ml of leucine-free MEM (GIBCO, Long Island, N.Y.) and then were incubated in the presence of 15 ml of leucine-free MEM containing 20 microCi/ml of L-[3,4,5-$^3$H] leucine (158 Ci/mmol; New England Nuclear, Boston, Mass.). After 24 hours, the media were collected as described above, combined with 55 ml of unlabeled CM, and passed over a 1 ml concanavalin A-Sepharose column (0.6×3.5 cm) at a speed of 4 ml/h. The column was washed and eluted a. 1 ml/h.

Again, the inhibitor-containing fractions were pooled and subjected to preparative tube gel electrophoresis. The resulting inhibitor containing gel extracts were stored at −70° C. until further use.

Polyclonal receptors to the purified inhibitor were raised in rabbits as described in detail hereinafter. Protein A-Sepharose CL-4B (Pharmacia Fine Chemicals, Piscataway, N.J.) was rehydrated in PBS containing 0.02 percent $NaN_3$, 0.05 percent Tween 20 [polyoxyethylene (20) sorbitan monolaurate] and 0.1 percent bovine serum albumin, and washed 3 times with a ten-fold excess of this buffer. The IgG fraction of the antisera was coupled to the washed beads as specified by the manufacturer at a ratio of approximately 80 micrograms protein A-Sepharose per 40 microliters of either anti-inhibitor reagent or pre-immune serum. The IgG-coated beads were added to 1 ml of CM collected from cloned BAEs cultured in the presence of [3,4,5-$^3$H] leucine. The samples were incubated for 1 hour at room temperature, the beads were washed by centrifugation (3 times with 1 ml of PBS-Tween buffer) and extracted for 1 hour at 37° C. with 0.25M Tris-HCl (pH 6.8) containing 2.2 percent SDS, 20 percent glycerol, 0.025 percent bromophenol blue and 2.5 percent (v/v) 2-mercaptoethanol. The resulting supernatant was analyzed by SDS-PAGE in slab gels or by liquid scintillation counting.

SDS-PAGE in slab (15×10×0.15 cm) and tube (10×0.5 cm) gels was then performed according to Laemmli, *Nature* (Lond.), 227, 680 (1970), whose illustrative teachings are incorporated herein by reference. The stacking gel consisted of 4 percent polyacrylamide and the separation gel of 9 percent polyacrylamide (both gels had a cross linkage of 3 percent). Slab gels consisting of a 7.5–20 percent gradient of polyacrylamide in the separation gel also were prepared. After electrophoresis, the gels were fixed and stained either with 50 percent tricholoracetic acid containing 1 percent Coomassie Brilliant Blue (BioRad, Richmond, Calif.), or with periodic acid Schiff reagent, as in Ginsburg et al, in *Methods in Hematology*, Harker et al. eds., vol. 8, pp. 158–176, Churchill Livingstone, New York (1983).

Molecular weight standards employed to determine the apparent molecular weight of the purified inhibitor included phosphorylase B (92,500), human plasminogen (90,000), transferrin (77,000), bovine serum albumin (66,200), human serum albumin (66,000), ovalbumin (43,500), carbonic anhydrase (31,000), soybean trypsin inhibitor (21,500), lysozyme (14,400) and the 66,000, 52,300, and 46,500 subunits of human fibrinogen.

To localize radiolabeled proteins, the stained slab gels were dried and processed for autoradiography as described in Bonner et al., *Eur. J. Biochem.*, 46, 83 (1974). The positions of the radiolabeled protein in tube gels was determined by slicing the gels into 1 mm pieces, extracting each gel slice into buffer as described above, and determining the radioactivity in each fraction.

Alkaline (SDS-free) continuous PAGE was performed as in Hjerten et al., *Anal. Biochem.*, 11, 219 (1965), using 0.37M Tris-glycine (pH 9.5) as both gel- and running buffer. Tube gels were 10 percent polyacrylamide with a cross linkage of 2.5 percent. Samples were brought to 40 percent sucrose, applied to the gel, and subjected to electrophoresis, first for 0.5 hours at 2.5 mA/cm$^2$ and then for 1–1.5 hours at 5 mA/cm$^2$.

Isoelectric focusing gels were prepared in glass tubes (2.5 mm) as in O'Farrell, *J. Biol. Chem.*, 250, 4007 (1975). The resulting pH gradient was determined by cutting the gels into 1 mm slices. Every two slices were combined and extracted into 0.2 ml $H_2O$ for 18 hours at 4° C., and the pH and radioactivity in each of these extracts was determined. Slices from parallel gels also were extracted into 0.2 ml PBS/Tween and assayed for inhibitor activity and radioactivity.

Inhibitor activity in polyacrylamide gels was localized either by direct measurement of the ability of the gel extracts to inhibit u-PA-mediated lysis of $^{125}$I-fibrin [fibrin-plate method of Loskutoff et al., *Proc. Natl. Acad. Sci.* (*USA*), 74, 3903 (1977)], or by reverse fibrin autography, as in Erickson et al., *Anal. Biochem.*, 137, 454 (1984). In the latter technique, the white lysis-resistant zones in the indicator film resulted from the presence of inhibitors in the slab gel.

To determine the stability of the inhibitor under denaturing conditions, the purified molecule (20 micrograms/ml) was incubated for 1 hour at 37° C. in 0.02M glycine, pH 2.7, containing 25 micrograms/ml of human serum albumin. The sample was neutralized by the addition of three volumes of assay buffer (pH 8.1) and subsequently tested at various dilutions made in assay buffer for residual activity by the $^{125}$I-fibrin plate assay. Inhibitor (20 micrograms/ml) also was incubated for 1 hour at 37° C. in PBS containing 0.025 percent SDS and albumin (25 micrograms/ml). The SDS was neutralized by the addition of three volumes of assay buffer containing 0.18 percent Triton X-100 [polyoxyethylene (9) octyl phenyl ether], and residual inhibitor activity was measured. Samples treated with PBS instead of glycine and SDS served as controls for these screenings. The effect of acid glycine and SDS on the inhibitor activity of purified protease nexin (160 micrograms/ml) was determined in a similar manner.

3. Formation of Polyclonal Receptors

Antisera to the inhibitor were raised in New Zealand rabbits by subcutaneous injections of 20 micrograms of purified inhibitor dissolved in 1 ml of saline and emulsified with 1 ml of Freund's complete adjuvant (Miles Laboratories, Naperville, Ill.). Booster injections employing 10 micrograms of purified inhibitor in 0.5 ml of saline and emulsified with an equal quantity of incomplete Freund's adjuvant (Miles Laboratories, Naperville, Ill.) were administered at 2 week intervals. Serum containing polyclonal receptors to the inhibitor was collected 10 days after the third and fourth immunizations and pooled.

4. Inhibitor Binding to t-PA Assay

Purified t-PA (50 microliters/well, 1 microgram/ml) in phosphate-buffered saline (PBS) was incubated overnight at 4° C. in U-bottom microtiter plates (PVC plastic, Falcon 3911, Microtest III, Falcon, Oxnard, Calif.). At this and every subsequent step, the plates were washed with SPRIA buffer (PBS supplemented with 0.1 percent BSA, 0.05 percent $NaN_3$ and 0.05 percent Tween 20). To "block" any remaining sites on the plastic, 3 percent BSA (200 microliters/well) was incubated in the wells for 1 hour at 37° C. Test samples and standard curves of purified inhibitor were prepared in dilution buffer (PBS supplemented with 3 percent BSA, 5mM EDTA, 0.1 percent Tween 80, and 0.02 percent $NaN_3$) and 50 microliters/well were incubated for 1 hour at 37° C. Bound inhibitor was detected by incubation for 2 hours at 37° C. with rabbit anti-inhibitor receptor (1:75 dilution in dilution buffer, 50 microliters/well). The bound antibody-inhibitor-t-PA complex then was quantitated by incubation for 2 hours at 37° C. with $^{125}$I-labeled goat anti-rabbit IgG (5×10$^4$ cpm/well, Cappel Laboratories, Cochranville, Pa.). The wells were cut individually and the radioactivity in each well determined in a gamma counter (CT (80-800) CT/T, General Electric, Milwaukee, Wis.).

5. Miscellaneous

Plasminogen was purified from outdated human plasma by affinity chromatography on lysine-Sepharose as described in Deutsch et al., *Science*, 170, 1095 (1970). Protein was determined by the method of Bradford, *Anal. Biochem.*, 12; 248 (1976), using bovine serum albumin as the standard. PA activity was assayed on $^{125}$I-fibrin coated multiwell tissue culture dishes as described by Loskutoff et al., *Proc. Nat. Acad. Sci. (USA)*, 74, 3903 (1977). Proteins were enzymatically labeled with $^{125}$I using solid-state lactoperoxidase/glucose oxidase reagents (Bio-Rad Laboratories, Richmond, Calif.) and carrier-free Na $^{125}$I (Amersham, Arlington Heights, Ill.), or, alternatively by the Iodo-gen procedure of Fraker et al., *Biochem. Biophys. Res. Commun.*, 80, 849 (1978), modified so that the labeling interval was only 5 minutes and the temperature was 4° C. A typical specific activity of the final product was $1-4\times10^6$ cpm/microgram protein. Bovine fibrinogen (fraction II, Calbiochem-Behring, La Jolla, Calif.) was purified as suggested in Mosesson, *Biochim. Biophys. Acta*, 57, 204 (1962) to remove plasminogen. Protease nexin was purified from cultured human fibroblasts as in Scott et al., *J. Biol. Chem.*, 258, 10439 (1983) and kindly provided by Dr. J. Baker, University of Kansas, Lawrence, Kans. The $^{125}$I-plasminogen cleavage assay was performed as described in Loskutoff et al., *J. Biol. Chem.*, 256, 4142 (1981) and Mussoni et al., *Thromb. Res.*, 34, 241 (1984).

B. Beta-PAI-Related

1. Reagents

Restriction enzymes, alkaline phosphatase, T4 DNA ligase, *E. coli* DNA polymerase I, Klenow fragent of DNA polymerase I, and T4 DNA polymerase were purchased from Boehringer Mannheim GmbH. Alpha-$^{32}$p dGTP (3000 Ci/mmol) and $^{35}$SdATP-alpha-S (600 ci/mmole; 1 Ci=37 GBq) were purchased from Amersham. Human alpha-thrombin was a generous gift of J. Fenton (Albany, New York, N.Y.), while fibrinogen was purchased from Calbiochem-Behring, La Jolla, Calif. The purified human urokinase [W.H.O. Urokinase Standard (preparation 66-46)] was obtained from the National Institute for Biological Standards and Control, Hollyhill, Hampstead, London, Great Britain. Human plasminogen was obtained and purified, according to the procedures of Deutsch et al., (1970) *Science*, 170, 1095–1096. The purification of BAE beta-PAI and the development of antibodies to it were as described by van Mourik et al., (1984) *J. Biol. Chem.*, 259, 14914–14921. Antiserum to the placental PAI was a gift from Dr. James Wun of The Rockerfeller University, New York, N.Y. Phage X $gt_{11}$ is available from the ATCC as ATCC 37194.

2. Preparation and analysis of crude placental extract

Frozen human placenta (3.5 g) was washed with PBS and extracted, into 15 ml of PBS containing 0.5% Triton X-100 [polyoxyethylene (9) octyl phenyl ether] at 4° C. The tissue was homogenized using a Dounce homogenizer, and cellular debris was removed by centrifugation at 10,000×g for 10 minutes. The extracts were analyzed for inhibitor activity by reverse fibin autography [Erickson et al., (1984) Analytical Biochemistry, 137, 454–463]. Monospecific antisera against human placental-type PAI and bovine beta-PAI were coupled to protein A Sepharose (Pharmacia, Uppsala, Sweden) and employed as described [van Mourik et al., (1984) *J. Biol. Chem.*, 259, 14914–14921; Sawdey et al. (1986) *Thromb. Res.*, 41, 151–160] to immunoprecipitate the PAIs present in the extract.

3. Immunological Screening of a $\lambda gt_{11}$ cDNA library

A human $\lambda gt_{11}$ cDNA library derived from a premature (34 week old) human placenta and consisting of $1\times10^6$ independent recombinant phages [Millan, (1986) *J. Biol. Chem.* 261, 3112–3115] was screened immunologically [Young et al., (1983) *Proc. Natl. Acad. Sci. USA*, 80, 1194–1198; Young et al., (1983) *Science*, 222, 778–782; Huynh et al., (1984) in DNA Cloning Techniques: A Practical Approach, ed. Glover, D. (IRL Press, Oxford)] for beta-PAI, using the affinity purified IgG fraction [Cuatrecasas (1969) *Biochem. Biophys. Res. Commun.* 35, 531–537] of antibodies to the purified BAE beta-PAI as antibody probe [van Mourik et al., (1984) *J. Biol. Chem.* 259, 14914–14921]. To visualize antibody binding, $^{125}$I-labeled protein A [55 milliCuries per milligram (mCi/mg)] was employed. Autoradiography was performed by exposing the filters to Kodak XAR5 film with an intensifying screen at –80° C.

4. Western blot analysis of *E. coli* lysates

Lambda $\lambda t_{11}$ and recombinant lysogens were induced and crude extracts of infected *E. coli* were prepared as described [Huynh et al., (1984) in DNA Cloning Techniques: A Practical Approach, ed. Glover, D. (IRL Press, Oxford)]. For Western blot analysis of the expressed PAI, 50 microliters (ul) of crude extract were fractionated by SDS-PAGE [Laemmli, (1970) *Nature (London)* 227, 680–685]. The proteins were electrophoretically transferred to nitrocellulose paper and immunoblotted as described [Lammle et al., (1986) *Thromb. Res.* 41, 747–759; Johnson et al., (1984) *Gene Anal. Techn.* 1, 3–8], using the immunoglobulin fraction of antiserum purified on either beta-PAI affinity columns (above) or on the isolated substantially pure fusion polypeptide.

For the affinity purification of antisera on the isolated, substantially pure fusion polypeptide, 900 ul of crude extract from induced *E. coli* lysogens [Huynh et al., (1984) in DNA Cloning Techniques: A Practical Approach, ed. Glover, D. (IRL Press, Oxford)] were fractionated by SDS-PAGE and transferred to nitrocellulose paper. Strips containing proteinaceous materials of $M_r$ 150–200 kilodaltons (kda) were excised from the nitrocellulose sheets and used for the affinity purification of antisera. Blocking of the nitrocellulose filter strips, binding of specific antibodies, and washings were performed as described for the screening of $\lambda gt_{11}$ libraries with antibody probes [Huynh et al. (1984) in *DNA Cloning Techniques: A Practical Approach*, ed. Glover, D. (IRL Press, Oxford)]. To elute bound antibody, the filter strips were incubated twice with 200 ul 0.1M glycine-HCl buffer, pH 2.5, containing 0.02% fetal calf serum for 3 minutes. The eluted material was neutralized by the addition of 140 ul 0.5 M Tris-HCl, pH 8.0, dialyzed overnight, and used as the primary antibody in Western blotting analysis.

5. Nucleic acid methods (a) Cloning and Sequencing of PAI Genes

Phage particles prepared by the plate-lysate method and purified by CsCl equilibrium centrifugation were used for the purification of phage DNA [Maniatis et al., (1982) in *Molecular Cloning:A Laboratory Manual*, Cold Spring Harbor Laboratory, Cold Spring Harbor, N.Y.]. Plasmid DNA was isolated by the method of Birnboim et al., (1979) *Nucleic Acids Res.* 7, 1513–1522, followed by two consecutive ethidium bromide/CsCl equilibrium centrifugations. Enzyme reactions were carried out according to the conditions suggested by the suppliers. Total RNA was prepared by the method of Berger et al., (1979) *Biochemistry* 18, 5143–5149 from cultured HT 1080 cells (ATCC CCL 121), fractionated by agarose gel electrophoresis in the presence of formaldehyde [Fellous et al., (1982) *Proc. Natl. Acad. Sci. USA.,* 79, 3082–3086], and subjected to Northern blot analysis [Thomas, (1980) *Proc. Natl. Acad. Sci. USA.,* 77,5201–5205].

DNA from 2 $\lambda t_{11}$ clones was digested with EcoRI endonuclease and the excised cDNA insert was subcloned into bacteriophage M13 cloning vector mp9 [Messing, (1982) *Gene* 19, 269–276] or plasmid vector pGEM-3 (Promega Biotec, Madison, Wis.). M13 clones containing the cDNA insert in both orientations were isolated and deletion libraries of both strands were constructed using the single-stranded M13 method of Dale et al., (1985) *Plasmid* 13, 31–40. Before sequencing, the size of the M13 templates was determined by electrophoresis on 0.7% agarose gels, and selected templates were sequenced by the dideoxy-chain-termination method [Sanger et al., (1977) *Proc. Natl. Acad. Sci. USA.,* 74, 5463–5487]. Both DNA strands were sequenced, and over 80% of each strand was sequenced two or more times.

Processing of DNA sequence data was accomplished using the Staden program [Staden, (1982) *Nucl. Acid. Res.* 10, 4731–4751]. Homology searches were done utilizing the Pearson Fast Protein homology program [Lipman et al., (1985) *Science* 227, 1435–1441].

(b) Expression in Eukaryotes (i) Production of PAI by Recombinant DNA Expression in Mammalian Cells A recombinant DNA vector capable of expressing the PAI gene in mammalian Chinese hamster ovary (CHO) cells is constructed in the following manner using procedures that are well known in the art and are described in more detail in Maniatis et al., *Molecular Cloning: A Laboratory Manual,* Cold Springs Harbor Laboratories (1982).

Lambda 3 clone DNA or plasmid $pPAI_3$ DNA is first subjected to restriction endonuclease digestion with restriction endonuclease EcoRI, and the resulting 3 kilobase pair (kb) fragment is purified by size fractionation. The 3'-recessed termini of the 3 kb restriction endonuclease digested DNA are filled in using the Klenow fragment of DNA Polymerase I. A synthetic oligonucleotide fragment having the sequence:

GCATCGGATCCGATGC is produced according to the methods of Caruthers et al., *J. Am. Chem. Soc.,* 103:3185 (1981), and Gait et al., *Cold Spring Harbor Symp. Quant. Biol.,* 47:393 (1983) and is blunt-end ligated to the filled in 3 kb fragment using T4 DNA ligase. The resulting ligated fragment comprising the 3 kb fragment and the synthetic oligonucleotide is further subjected to BamHI restriction endonuclease digestion.

The simian virus (SV40) based expression vector, pKSV-10 (Pharmacia Fine Chemicals, Piscataway, N.J.), is subjected to BglII restriction endonuclease digestion. The above prepared BamHI digested fragment containing PAI coding sequences is combined with the BglII digested vector and ligated using T4 DNA ligase which results in the formation of a circular recombinant expression plasmid denominated pSV-PAI.

The expression plasmid pSV-PAI contains an intact *E. coli* ampicillin resistance gene. *E. coli* RR101 (Bethesda Research Laboratories, Gaithersburg, Md.) when transformed with pSV-PAI can thus be selected on the basis of ampicillin resistance for those bacteria containing the plasmid. Plasmid-containing bacteria are then cloned and the clones are subsequently screened for the proper orientation of the inserted PAI coding gene into the expression vector.

Screening for orientation is accomplished by taking into account the location of PstI restriction endonuclease sites on both the inserted gene and the expression vector. In pSV-PAI, PstI digestion generates fragments of about 3.9, 3.1, 3.0 and 0.5 kb if the PAI-containing insert is 3' to the SV40 transcriptional promoter when read from left to right as shown in FIG. 22, and generates fragments of about 3.9, 3.5, 2.6 and 0.5 kb when the insert is in the reverse orientation. Therefore, identification of pSV-PAI constructs with the proper orientation requires size analysis of the fragments generated after PstI restriction endonuclease digestion, and the selection of those wherein the fragments are about 3.9, 3.1, 3.0 and 0.5 kb. The construct with the insert in the appropriate beforementioned orientation is selected for further use in expression, and is referred to hereinafter as pSV-PAI.

The above obtained plasmid, pSV-PAI, containing the gene that encodes PAI is propagated by culturing *E. coli* containing the plasmid. The plasmid DNA is isolated from *E. coli* cultures using the alkaline lysis method described in Maniatis et al., *Molecular Cloning: A Laboratory Manual,* Cold Spring Harbor Laboratories (1982).

Expression of PAI is accomplished by the introduction of pSV-PAI into the mammalian cell line, CHO, using the calcium phosphate-mediated transfection method of Graham et al., *Virol.,* 52:456 (1973). To ensure maximal efficiency in the introduction of pSV-PAI into all CHO cells in culture, the transfection is carried out in the presence of a second plasmid, pSV2NEO (ATCC #37149) and the cytotoxic drug G418 (GIBCO Laboratories, Grand Island, N.Y.) as described by Southern et al., *J. Mol. Appl. Genet.,* 1:327 (1982). Those CHO cells that are resistant to G418 are cultured and have acquired therein both plasmids, pSV2NEO and pSV-PAI, and are designated CHO/pSV-PAI cells. By virtue of the genetic architecture of the pSV-PAI expression vector, PAI is expressed in the resulting CHO/pSV-PAI cells and can be detected in and purified from the cytoplasm of these cells.

Expressed PAI is conveniently detected by the reverse fibrin autography (RFA) assay described before. To that end, CHO/pSV-PAI cells are cultured and subsequently lysed in SDS-PAGE sample buffer as described by Laemmli, *Nature,* 227:680 (1970). The resulting solution containing cellular protein is centrifuged at 15,000 rpm for 10 minutes and the supernatants collected therefrom. The resulting supernate is subjected to SDS-polyacrylamide gel electrophoresis and biologically active PAI is analysed by RFA.

(ii) Production of PAI by Recombinant DNA Expression in Yeast

The recombinant vector capable of expressing the PAI gene in the yeast *Saccharomyces cerevisiae* (*S. cerevisiae*) is constructed in the following manner using procedures referred to in Section III B5 (b) (i). Many of the steps are identical to those used above except as is necessary to accomodate insertion of the PAI gene into a yeast-compatible expression vector and the manipulation of yeast cells.

After isolation of the 3 kb fragment from the $\lambda$ 3 clone or $pPAI_3$ and the filling in of the 3'-recessed termini, a similarly prepared synthetic oligonucleotide having the sequence:

GCATCGATGC, is blunt-end ligated thereonto the resulting fragment. The yeast expression vector, pTDT1 (ATCC # 31255), and the oligonucleotide ligated fragment are both ClaI restriction endonuclease digested, combined and further ligated together using T4 DNA ligase to form a circular recombinant expression plasmid denominated pY-PAI. Following transformation of E. coli with the plasmid so prepared, the selection of ampicillin resistant, plasmid containing bacteria follows as above relying upon the ampicillin resistance gene present on pY-PAI.

Plasmid-containing bacteria are cloned and screened for the proper orientation of the inserted PAI gene by essentially following the method above. In pY-PAI, BamHI restriction endonuclease digestion generates fragments of about 7.4 and 3.3 kb if the PAI-containing insert is 3' to the TRP1 yeast promoter of pTDT1 when read from left to right as shown in FIG. 22. The construct with the insert in the beforementioned appropriate orientation is selected for further use in expression, and is referred to hereinafter as pY-PAI.

Expression of PAI in yeast is accomplished by transformation of strain SHY3 *S. cerevisiae* (ATCC # 44771) using pY-PAI plasmid DNA propagated and purified as described before. After transformation by the spheroplast procedure of Hinnen et al., *Proc. Natl. Acad. Sci. U.S.A.,* 75:1929 (1978), SHYU3 cells are cultivated in nutrient selection medium comprising 0.67 percent yeast nitrogen base without amino acids (Difco Laboratories, Detroit, Mich.), 2 percent glucose and 50 micrograms per milliliter each of adenine, leucine and uracil as described by Miyajima et al., *Mol. Cell Biol.,* 4:407 (1984). By virtue of the genetic architecture of the pY-PAI expression vector, PAI is expressed in the resulting pY-PAI transformed SHY3 cells, hereinafter SHY3/pY-PAI cells, and can be detected in and purified from the cytoplasm of these cells.

Expressed PAI is conveniently detected by the RFA assay as described before. To that end, SHY3/pY-PAI cells are exponentially grown to a density wherein the optical density at 600 nanometers (nm) (OD600) is equal to 1, and then the yeast cells are washed with water and suspended in three volumes of a solution containing 50 mM potassium phosphate (pH 7.0), 1 mM ethylenediamine tetra-acetic acid (EDTA), 5 mM 2-mercaptoethanol, 0.5 mM phenylmethylsulfonylflouride and 1 microgram each per milliliter of leupeptin and pepstatin. Yeast cells are then disrupted by manual shaking with glass beads and centrifuged at 12,000 rpm for 30 minutes in a Sorval SS34 rotor. The supernatant from centrifugation is diluted 1:1 with a twice-concentrated yeast cellular proteins also containing the SDS-PAGE sample buffer described before. This solution is centrifuged and analysed by RFA after SDS-PAGE as also described.

In each of the above illustrations, the resulting expressed PAI contains the entire arino acid residue sequence and further includes the sequence as follows located at the amino-terminal end of the mature PAI:

Met-Gln-Phe-Gly-Glu-Gly-Ser-Ala.

The foregoing is intended as illustrative of the present invention but not limiting. Numerous variations and modifications can be effected without departing from the true spirit and scope of the invention.

What is claimed is:

1. An isolated antibody that binds to an endothelial cell plasminogen activator inhibitor, wherein said inhibitor is human or bovine beta-PAI.

2. The antibody of claim 1 wherein said inhibitor is human.

3. The antibody of claim 1 wherein said inhibitor is bovine.

4. The antibody of claim 1 that is a polyclonal antibody.

5. The antibody of claim 1 that is a monoclonal antibody.

6. The antibody of claim 1 that is an idiotype-containing polypeptide portion of an antibody.

7. The antibody of claim 1 that is a Fab, Fab' or F(ab')$_2$ portion of an antibody.

8. The antibody of claim 1 that is a mammalian anti-inhibitor antibody.

9. The antibody of claim 1 that is a rabbit anti-inhibitor antibody.

10. The antibody of claim 1 that is an antibody produced by immunization of an animal with purified human or bovine endothelial cell plasminogen activator inhibitor.

11. The antibody of claim 10 wherein said purified inhibitor is bovine.

* * * * *